US009790197B2

(12) United States Patent
Jung et al.

(10) Patent No.: US 9,790,197 B2
(45) Date of Patent: Oct. 17, 2017

(54) COMPOUND, PHARMACEUTICALLY ACCEPTABLE SALT OR OPTICAL ISOMER THEREOF, METHOD FOR PREPARING THE SAME, AND PHARMACEUTICAL COMPOSITION FOR PREVENTION OR TREATMENT OF VIRAL DISEASES CONTAINING SAME AS ACTIVE INGREDIENT

(71) Applicants: KOREA RESEARCH INSTITUTE OF CHEMICAL TECHNOLOGY, Yooseong-gu, Daejeon (KR); KATHOLIEKE UNIVERSITEIT LEUVEN K.U. LEUVEN R & D, Leuven (BE)

(72) Inventors: Young Sik Jung, Daejeon-si (KR); Soo Bong Han, Daejeon-si (KR); Chong-Kyo Lee, Daejeon-si (KR); Hae Soo Kim, Daejeon-si (KR); Jin Soo Shin, Chungcheongnam-do (KR); Johan Neyts, Kessel-Lo (BE); Hendrik Jan Thibaut, Bierbeek (BE); Yashwardhan Radhamohan Malpani, Daejeon-si (KR)

(73) Assignees: KATHOLIEKE UNIVERSITEIT LEUVEN K.U. LEUVEN R & D, Belgium (BE); KOREA RESEARCH INSTITUTE OF CHEMICAL TECHNOLOGY, Daejeon-si (KR)

( * ) Notice: Subject to any disclaimer, the term of this patent is extended or adjusted under 35 U.S.C. 154(b) by 0 days.

(21) Appl. No.: 14/651,656

(22) PCT Filed: Dec. 16, 2013

(86) PCT No.: PCT/KR2013/011668
§ 371 (c)(1),
(2) Date: Jun. 11, 2015

(87) PCT Pub. No.: WO2014/092514
PCT Pub. Date: Jun. 19, 2014

(65) Prior Publication Data
US 2015/0336920 A1 Nov. 26, 2015

(30) Foreign Application Priority Data

Dec. 14, 2012 (KR) .................. 10-2012-0146081
Dec. 16, 2013 (KR) .................. 10-2013-0156409

(51) Int. Cl.
*C07D 307/93* (2006.01)
*C07D 407/12* (2006.01)
*C07D 405/12* (2006.01)
*C07D 409/12* (2006.01)
*C07D 413/12* (2006.01)
*C07D 417/12* (2006.01)

(52) U.S. Cl.
CPC ......... *C07D 307/93* (2013.01); *C07D 405/12* (2013.01); *C07D 407/12* (2013.01); *C07D 409/12* (2013.01); *C07D 413/12* (2013.01); *C07D 417/12* (2013.01)

(58) Field of Classification Search
CPC .................................... C07D 307/93
See application file for complete search history.

(56) References Cited

U.S. PATENT DOCUMENTS

| 3,892,807 A | 7/1975 | Sahm |
| 3,984,552 A | 10/1976 | Cragoe, Jr. et al. |
| 4,569,945 A | 2/1986 | Campbell |
| 2002/0091261 A1 | 7/2002 | Bold et al. |
| 2010/0261706 A1 | 10/2010 | Jagtap et al. |

FOREIGN PATENT DOCUMENTS

| EP | 409410 A1 | 1/1991 |
| EP | 0481708 A1 | 4/1992 |
| EP | 1081138 A1 | 3/2001 |
| EP | 2324820 | 6/2011 |
| FR | 2392951 | 1/1976 |
| GB | 1 425 295 | 2/1976 |

(Continued)

OTHER PUBLICATIONS

Aleman, J. et al., "Organocatalytic Highly Enantioselective α-Arylation of β-Ketoesters", *Angewandte Chemie International Edition*, 2007, vol. 46, pp. 5515-5519.
Almog, Joseph et al., "The reaction between phloroglucinol and vic polycarbonyl compounds: extension and mechanistic elucidation of Kim's synthesis for bipolarofacial bowl-shaped compounds", *Tetrahedron* 65, (2009), pp. 7954-7962.
Benders, J. et al., "Esr spectra of semidiones derived from indandione-1,3," *Journal of Molecular Structure*, vol. 19, (Dec. 1, 1973), pp. 431-440.
Black, D.S.C., et al., "Reactions of Ninhydrin with Activated Anilines: Formation of Indole Derivatives", *Tetrahedron*, (1994), vol. 50, No. 37, pp. 10983-10994.
Bullington, J.L. et al., "Synthesis of Spiro[2H-indole]-3,3'-diones and Spiro[benzofuran-2,1'-isobenzofuran]-3,3'-diones via Transannular Reactions of Eight Membered Ring Intermediates", *Journal of Heterocyclic Chemistry*, vol. 35 (Mar.-Apr. 1998), pp. 397-403.
Bullngton, James L., et al., "Synthesis of tetrahydroineno[1,2-b] indol-10-ones and Their rearrangement to [2] Benzopyrano[4,3-b]indol-5-ones", *Journal of Organic Chemistry*, vol. 58, No. 18, (1993), pp. 4833-4836.

(Continued)

*Primary Examiner* — Golam M M Shameem
(74) *Attorney, Agent, or Firm* — Brinks Gilson & Lione

(57) ABSTRACT

The present invention relates to a novel compound, to a pharmaceutically acceptable salt or optical isomer thereof, to a method for preparing same, and to a pharmaceutical composition for the prevention or treatment of viral diseases containing same as an active ingredient. The novel compound according to the present invention not only has low cytotoxicity but also has excellent antiviral activity against picornavirus such as coxsackievirus, enterovirus, echovirus, poliovirus and rhinovirus, and thus can be effectively used as a pharmaceutical composition for the prevention or treatment of viral diseases such as infantile paralysis, acute hemorrhagic conjunctivitis, viral meningitis, hand-foot-and-mouth disease, vesicular disease, hepatitis A, myitis, myocarditis, pancreatitis, diabetes, epidemic myalgia, encephalitis, cold, herpangina, foot-and-mouth disease, asthma, chronic obstructive pulmonary disease, pneumonia, sinus infection, or otitis media.

4 Claims, No Drawings

(56) References Cited

FOREIGN PATENT DOCUMENTS

| | | |
|---|---|---|
| GB | 1533388 | 11/1978 |
| JP | 60-109541 A | 6/1985 |
| JP | 2001 089455 | 4/2001 |
| RU | 2207132 | 6/2003 |
| SU | 725559 | 3/1980 |
| UA | 79834 | 7/2007 |
| WO | WO 03/032265 A2 | 10/2003 |
| WO | WO 2004/041201 A2 | 5/2004 |
| WO | WO 2004/041812 A2 | 5/2004 |
| WO | WO 2004/087153 A2 | 10/2004 |
| WO | WO 2010/003023 A2 | 1/2010 |

OTHER PUBLICATIONS

Butera, John A., "Synthesis and Potassium Channel Opening Activity of Substituted 10H-Benzo[4,5]furo[3,2-b]indole- and 5,10-Dihydro-indeno[1,2-b]indole-1-carboxylic Acids", Bioorganic & Medicinal Chemistry Letters, 2001, vol. 11, pp. 2093-2094.

Courant, J. et al., "1,3-Indandiones VIII. 2-Hydroxy-2-indolyl-1,3-indandiones, 2-(indol-3-ylmethylene indandione and derivatives: search for anti-inflammatory activity," European Journal of Medicinal Chemistry, Editions Scientifique Elsevier, Paris, FR., vol. 24, No. 2, (Mar. 1, 1989), pp. 145-154.

Das, S. et al., "A Facile Synthesis of Benzofuroisocoumarins from C-2 Arylated 1,3-Indanediones", Synlett, 2006, vol. 2, pp. 207-210.

Das, Suven et al., "A simple synthesis of 4-substituted 2,3-benzoxazinones from C-2 arylated 1,3-indanediones", Tetrahedron Letters, vol. 52, No. 25, (Apr. 27, 2011) pp. 3243-3246.

Extended European Search Report for EP 12799827.6, mailed Nov. 19, 2014.

Extended European Search Report for EP 12800577.4, mailed Mar. 24, 2015.

Hark, Richard R. et al. "Synthetic studies of novel ninhydrin analogs", Can. J. Chem., vol. 79, (2001): pp. 1632-1654.

Hashimoto, Suzumi et al., "Dynamic behavior of cyclic hemiacetals of 2-Hydroxy-2-(2-hydroxyphenyl)-1,3-indandione derivatives", Chemistry Letters. vol. 37, No. 7, (2008), pp. 696-697.

Heffner, Robert J., Joullie, Madeleine, "A Synthesis of Two Novel Benzo[f]Ninhydrin Analogs: 6-Methoxybenzo[f]Ninhydrin and Thieno[f]Ninhydrin", Synthetic Communications, 21(8&9), (1991), pp. 1055-1069.

Heffner, Robert J., Joullie, Madeleine, "Synthetic Routes to Ninhydrines, Preparation of Ninhydrin, 5-Methoxyninhydrin, and 5-(Methylthio)Ninhydrin.", Synthetic Communications, 21(21); (1991); pp. 2231-2256.

International Search Report and Written Opinion of the International Searching Authority for PCT/KR2012/004804, mailed Dec. 28, 2012.

International Search Report for Application No. PCT/KR2013/011668, dated Mar. 31, 2014.

Jeyachandran, Malaichamy et al., "Synthesis, Antimicrobial, and Anticoagulant Activities of 2-(Arysulfonyl) indane-1,3-diones", Organic Chemistry International, vol. 2, No. 4, (Jan. 1, 2011) pp. 175-179.

Kapoor, Mona et al., "Stereoselective Synthesis of Z-3-alkoxy-2-[(4'-methoxyphenyl)methylidene]-1(3H)-isobenzofuranones", Tetrahedron Letters, vol. 59, No. 27, pp. 5027-5031, (Jun. 30, 2003).

Kundu, Sandip Kumar et al., "Theoretical studies of the acid-catalyzed condensation of ninhydrin with aromatic compounds", Indian Journal of Chemistry; Section B: Organic Chemistry, vol. 43B, No. 10, (2004), pp. 2212-2216.

Kundu, Sandip Kumar et al., "6-(α-Hydroxy-α-aryl/naphthyl)methyl-3,4-dihydro-2,5-benzodiazocin-1(2H)-ones and diphenylmethanes from C-2 arylated 1,3-indanediones", Journal of Chemical Research. vol. 11, (2004). pp. 781-783.

Letcher, Roy M., "First Synthesis of Spiro[benzofuran-2,1'-isobenzofuran]-3,3'-dione and its X-Ray Crystal Structure", J.Chem.Soc.Perkin Trans.1, 1992, pp. 1769-1771.

Leuchs, Hermann, Wulkow, Gerhard, and Gerland, Heinz, "Indolenines V. Addition of Acid Halides to Indolenines", Caplus, (1932), vol. 151, pp. 1586-1592.

Liu, Yaya et al., "Investigating the Origin of the Slow-Binding Inhibition of HCV NS3 Serine Protease by a Novel Substrate Based inhibitor", BioChemistry, vol. 42, No. 29, (Jul. 1, 2003). pp. 8862-8869.

Lombardino, J.G. et al., "Anti inflammatory 2-Aryl-1,3-indandiones", Journal of Medicinal Chemistry, (1968), vol. 11, No. 6, pp. 342-347.

Mehdi, Sayed Hansan, "Synthesis. characterization, antimicrobial and enzymatic activity of 4b,9b-dihydroxy-7,8-dihydro-4bH-indeno[1,2-b]benzofuran-9,10(6H,9bH)-dione", Journal of Molecular Structure, 2011, vol. 1006, pp. 318-323.

Mosher, William A. et al., "Reactions of some methylene ketones with dimethyl phthalate. New route to 2-substituted 1,3-indandiones", The Journal of Organic Chemistry, vol. 36, No. 11, (Jun. 1, 1971), pp. 1561-1563.

Mudiganti, N.V.S., et al., "Ytterbium triflate-catalyzed conjugate addition of β-ketoesters to activated 1,4-naphthoquinones", Tetrahedron Letters, vol. 65, (2009), pp. 1716-1723.

Na, J. E. et al., "Serendipitous one-pot synthesis of brand-new, bowl-shaped molecular architecture from phloroglucinol and ninhydrin", Tetrahedron Letters, vol. 46, No. 26, (Jun. 27, 2005), pp. 4505-4508.

Na, Jeong Eun et al., "Selective methylation of the Ninhydrin-phenol adducts with I2 in MeOH", Bulletin of the Korean Society, vol. 25, No. 4, (2004), pp. 569-572.

Na, Jeong Eun et al., "Synthesis of benzo[b]indeno [2,1-d]furanone skeleton from ninhydrin and cyclohexane-1, 3-dione derivatives", Bulletin of the Korean Chemical Society, vol. 24, No. 12, (2003), pp. 1725-1726.

Neiland, L.E. et al., "2-Aryl-4-azaindain-1, 3-diones", Chemistry of Heterocyclic Compounds, vol. 3, No. 1, (Jan. 1, 1969), pp. 81-83.

Ooyama, Yousuke. "Molecular design of novel non-planar heteropolycyclic fluorophores with bulky substituents: convenient synthesis and solid-state fluorescence characterization", Organic & Biomolecular Chemistry, 2006, vol. 4. pp. 3406-3409.

Ozola, A. Ya et al., "4-Azaindane-1, 3-dione derivatives. III. Reactivities and prototropic transformations of new 4-azaindane-1,3-diones", Chemistry of Heterocyclic Compounds, vol. 12, No. 2, (Feb. 1, 1976), pp. 220-226.

Ozola, A. Ya et al., "A new method of synthesizing 4-azaidan-1, 3-dione derivatives", Chemistry of Heterocyclic Compounds, vol. 9, No. 8, (Aug. 1, 1973), pp. 1062-1082.

Patick, A.K. et al., "In Vitro Antiviral Activity of AG7088, a Potent Inhibitor of Human Rhinovirus 3C Protease", Antimicrobial Agents and Chemotherapy, (Oct. 1999), vol. 43. No. 10. pp. 2444-2450.

Pevear, Daniel C. et al., "Activity of Pieconaril against Enterviruses", Antimocrobial Agents and Chemotherapy, (Sep. 1999), vol. 43, No. 9, pp. 2109-2115.

Poupelin, J.P. et al., "Dervies de 1 'hydroxy-2 indanedione-1, 3.II. Produits de condensation de la ninhydrine avec les polyphenols et leurs derives 0-methyles//2-hydroxy-1,3-indanedione derivatives. II. (Condensation of ninhydrin with polyphenols and their 3-methylated derivatives)", European Journal of Medicinal Chemistry, Editions Scientifique, vol. 15, No. 3, (Jan. 1, 1980), pp. 253-262.

Poupelin, Jean Pierre et al., "Synthese Et Proprietes Pharmalogiques De Derives De L'Hydroxy-2 Indanedione-1,3; I. Produits De Condensation De La Ninhydrine Avec Les Phenols C-Alkyles", Eur. J. Med. Chem.—Chimica Therapeutique, Mar.-Apr. vol. 14, No. 2, (Jan. 1, 1979), pp. 171-179 (including English abstract).

Prabhakar, et al., "Identification and evaluation of antioxidant, analgesic/anti-inflammatory acitvity of the most active ninhydrin-phenol adducts synthesized", Bioorganic & Medicinal Chemistry, vol. 14, No. 21, (Nov. 1, 2006). pp. 7113-7120.

Registry 908828-65-9 (Sep. 27, 2006); 907954-66-9 (Sep. 20, 2006); 408315-53-7 (Apr. 26, 2002).

Roth, H.J., et al., "Reaktionen mit Dimethoxyanilinen und reaktiven Aromaten", Archiv der Pharmazie, (1976), vol. 82, pp. 81-91.

Sastry Mudiganti, N. V. et al., "Ytterbium triflate-catalyzed conjugate addition of beta-ketoesters to activated 1, 4-naphthoquinones", Tetrahedron. (Feb. 21, 2009), vol. 65, No. 8. pp. 1716-1723.

(56) References Cited

OTHER PUBLICATIONS

Schmitt, Gerard et al., "A New and Mild Synthesis of Substituted Salicylic Acids", *Synthesis*, vol. 1984, No. 09 (Jan. 1, 1984), pp. 758-760.
Solomek, T., et al., "Photoenolization-Induced Oxirane Ring Opening in 2,5-Dimethylbenzoyl Oxiranes to Form Pharmaceutically Promising Indanone Derivatives", *J. Org. Chem.* Vo. 75, No. 21, 2010, pp. 7300-7309.
Song, H.N. et al., "Formation of Benzo[b]Indeno [2,1-d]Furanone Ring System During Alkylation of 2-(2-Hydroxyaryl)-2-Hydroxy-1,3-Indanedione Derivatives", *Synthetic Communications*, (1999), vol. 29, No. 16, pp. 2759-2767.
Song, Hyun Nam et al., "The Reaction of Ninhydrin with Polymethylbenzenes in the Presence of Acid Catalyst: Formation of 2-aryl-1,3-indanedione and indenoindanone Derivatives", *Bull. Korean Chem. Soc.*, vol. 20, No. 10, pp. 1229-1231, (Oct. 20, 1999).
Song, Hyun Nam et al., "Friedel-Crafts Type Reactions of Some Activated Cyclic Ketones with Phenol Derivatives", *Synthetic Communications*, 29(19), pp. 3303-3311, (1999).
Song, Hyun Nam et al., "A Study on the Friedel-Crafts Type Reaction of Hinhydrin with Arenes". *Synthetic Communications*, 28(10), pp. 1865-1870, (1998).
Song, Hyun Nam et al., "The Reaction of Ninhydrink with Trimethylbenzenes Under Friedel-Crafts Reaction Conditions", *Synthetic Communications*, 30(6), pp. 1057-1066, (2000).
Song, Hyun Nam et al., "Difference in Reactivity during Alkylation of 2-(2-Hydroxyaryl)-1,3-indanedione and N-(2-Hydroxyphenyl)phthalimide", *Bull. Korean Chem. Soc.*, (1999): vol. 20, No. 6, pp. 631-632.
Stadlbauer, W. et al. DN, "Thermal Cyclization of 3-Azido-2-phenyl-indan-1-one to 5H-Indenol[1,2-b]indol-10-one", *Journal of Heterocyclic Chemistry*, (2002) 39(1), pp. 131-135 (Abstract).
Suzuki, Masaya et al., "Photorearrangements in spiro-conjoined cyclohexa-2,5-dien-1-one", *Tetrahedron Letters*, vol. 67, pp. 5500-5506, Available online (May 14, 2011).
Thibaut et al., "A novel class of highly potent small molecule inhibitors of entero/rhinovirus replication with an excellent safety and pharmacokinetic profile are highly effective against enterovirus infections in mice.", Poster presented at 26th International Conference on Antiviral Research. San Francisco, CA, (May 11-15, 2013).
Thibaut et al., "A novel class of highly potent small molecule inhibitors of entero/rhinovirus replication that target the non-structural protein 2C", Poster presented at 26th International Conference on Antiviral Research, San Francisco, CA (May 11-15, 2013).
The Merck Index, 2001, Thirteenth Edition, p. 674, 1380, 2432, 7314.
Yin-Murphy, Marguerite and Almond, Jeffrey W., "Chapter 53Picomaviruses", *Medical Microbiology*, 4th Ed., Galveston (TX): Univ. of Texas Medical Branch at Galveston, (1996), pp. 1-18.
Diana, Guy D. "Inhibitors of Picornavirus Replication", *Current Medicinal Chemistry-Anti-Infective Agents*, vol. 2. No. 1. (Mar. 2003), pp. 1-12.
Groarke, James M. et al. "Attenuated Virulence of Pleconaril-Resistant Coxsackievirus B3 Variants", *The Journal of Infectious Diseases*, (Jun. 1999), vol. 179(6); pp. 1538-1541.
Heinz, Beverly A. et al., "The Antiviral Compound Enviroxime Targets the 3A Coding Region of Rhinovirus and Poliovirus", *Journal of Virology*, vol. 6, No. 7, (Jul. 1995), pp. 4189-4197.
Ledford, Rebecca M. et al., "VP1 Sequencing of All Human Rhinovirus Serotypes: Insights into Genus Phylogeny and Susceptibility to Antiviral Capsid-Binding Compounds", *Journal of Virology*, vol. 78, No. 7, (Apr. 2004), pp. 3663-3674.
McKinlay, Mark A. et al., "Treatment of the Picornavirus Common Cold by Inhibitors of Viral Uncoating and Attachment", *Annual Review of Microbiology*, (Oct. 1992), vol. 46. pp. 635-654.
Miller, F. Dewolfe et al., "Controlled Trial of Enviroxime Against Natural Rhinovirus Infections in a Community", *Antimicrobial Agents and Chemotherapy*, (Jan. 1985), vol. 27. No. 1, pp. 102-106.
Sun, Fang-Gang, et al., "N-Heterocyclic carbine-catalyzed [4 + 1] annulation of phthalaldehyde and imines," Organic & Biomolecular Chemistry, vol. 9, No. 10, May 21, 2011, pp. 3573-3635.
Arens, A., et al., "Amino derivatives of 2-piperonyl-1,3-idandione," Zhurnal Obshchei Khimii, 1964, vol. 34, No. 2, pp. 442-445.
Jasinskas, L., et al., "Synthesis of secondary amines of 4-methyl-2-phenylindandione," Lietuvos TSR Aukstuju Mokyklu Mokslo Darbai, Chem. Ir Chem. Technol., 1965, vol. 7, pp. 77-80.
Vasilev, G., et al., "Synthesis, chemical structure, and biological activity of certain N-substituted 2-ureido-or thioureido-2-phenyl-1,3-indandiones," Doklady Bolgarskoi Akademii Nauk, 1986, vol. 39, No. 2, pp. 93-96.
Grinsteins, V., et al., "Synthesis and study of thioureas. Infrared spectra of 2-aryl-2-thiocarbamido-1,3-indandiones," Latvijas PSR Zinatnu Akademijas Vestis, Kimijas Serija, 1972, vol. 4, pp. 441-444.
Bite, Dz., et al., "Substituted thiourea β-dicarbonyl compounds. IX. Spectroscopic study of 2-substituted N-[1, 3-indandion-2-yl] thiourea and 2-(2-iminothiazolidin-3-yl]-2-substituted 1, 3-indandiounes," Latvijas PSR Zinatnu Akademijas Vestis Kimijas Serija, 1969, vol. 1, pp. 109-112.
Arens, A., et al., "Isomerization of 2-amino-2-substituted 1,3-indandiones," Latvijas PSR Zinatnu Akademijas Vestis, Kimijas Serija, 1980, vol. 6, pp. 667-691.
Rotbergs, J., et al., "Condensation of dicarboxylic acid anhydrides with compounds containing active methylene groups. XXVII. 2-Aryl-1,3-indandiones containing methyl groups," Latvijas PSR Zinatnu Akademijas Vestis, Kimijas Serija, 1974, vol. 1, pp. 75-78.
Zalukaev, L.P., et al., "Synthesis of new α-nitro-α-arylmethylenephthal ides," Izvestiya Vysshikh Uchebnykh Zavedenii, Khimiya I Khimicheskaya Tekhnologiya, 1970, vol. 13, No. 10, pp. 1453-1456.
Arens, Augusts, et al., "Reduction of aminodicarboxylic compounds. III. 2-Alkylamino-2-phenyl-3-indanon-1-ol and 2-alkylamino-2-phenyl-1,3-indandiol," Journal of Organic Chemistry of the USSR, 1969, vol. 5, No. 9, pp. 2094-2097.
Zalukaev, L.P., et al., "Synthesis of α-nitromethylpyridine and its derivatives," Khimiya Geterotsiklicheskikh Soedinenii, 1967, vol. 3, pp. 515-517.
Briede, V., et al., "4,5-Dimethoxy-2-β-naphthyl-1,3-indandione," Latvijas PSR Zinatnu Akademijas Vestis, Kimijas Serija, 1967, vol. 3, pp. 329-333.
Arens, A., et al., "2-Amino derivatives of 4,5-and 5,6-dimethoxy-2-phenylindan-1,3-diones," Latvijas PSR Zinatnu Akademijas Vestis, Kimijas, 1966, vol. 3, pp. 342-346.
Eckstein, Zygmunt, et al., "Infrared absorption spectra of 2-nitroindandione derivatives," Bulletin de l'Academie Polonaise des Sciences, Serie des Sciences Chimiques, 1960, vol. 8, No. 10, pp. 579-586.
Zalukajevs, L., et al., "Nitration of phthalones," Zhurnal Obshchei Khimii, 1957, vol. 27, pp. 3278-3282.
Zalukaievs, L., et al., "Preparation of 2-nitromethylquinoline and its derivatives," Zhurnal Obshchei Khimii, 1956, vol. 26, pp. 2639-2642.
Vegnere, V., et al., "Adsorptive capacity of 2-amino-substituted indans on a mercury electrode," Latvijas PSR Zinatnu Akademijas Vestis, Kimijas Serija, 1973, vol. 4, pp. 446-451.
Arens, Augusts, et al., "2-Amino-2-halophenyl-1,3-indandiones," Latvijas PSR Zinatnu Akademijas Vestis, Kimijas Serija, 1969, vol. 4, pp. 446-451.
Gudriniece, E., et al., "2-Azido-2-substituted indan-1,3-dione," Doklady Akademii Nauk SSSR, 1966, vol. 171, No. 4, pp. 869-871.

COMPOUND, PHARMACEUTICALLY ACCEPTABLE SALT OR OPTICAL ISOMER THEREOF, METHOD FOR PREPARING THE SAME, AND PHARMACEUTICAL COMPOSITION FOR PREVENTION OR TREATMENT OF VIRAL DISEASES CONTAINING SAME AS ACTIVE INGREDIENT

TECHNICAL FIELD

The present invention relates to novel compounds, pharmaceutically acceptable salts or optical isomers thereof, methods for preparing the same, and pharmaceutical compositions for prevention or treatment of viral diseases containing the same as active ingredients.

BACKGROUND TECHNOLOGY

Picornaviruses are non-enveloped, positive single-stranded RNA viruses with an RNA genome 7.2-8.5 Kb long. These viruses are very small and globular in shape with a size of about 22-30 nm, and were first identified a long time ago. Among the viruses belonging to the family Picornaviridae are enteroviruses including rhinovirus, poliovirus, coxsackie virus A, coxsackie virus B, and echovirus, and hepatitis A virus.

The diseases that picornaviruses, RNA viruses, cause are varied, ranging from respiratory diseases to digestive diseases, to circulatory diseases and to dermal diseases, examples of which include poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, and foot-and-mouth disease. However, there are no therapeutic agents for curing these diseases. Most of the drugs under development are uncoating inhibitors. Viruses belonging to the family Picornaviridae cause various diseases including the aforementioned respiratory diseases, which evoke hygienic, social and economic issues. Picornaviruses are the main causative agents of waterborne diseases. Being very stable and difficult to disinfect, they incessantly cause related viral diseases.

Human rhinoviruses (hRV) have been recently associated with the majority of asthma exacerbations, and are known to exist even in bronchial tissues of many stable asthma patients. Comparison of respective bronchial mucosa biopsy specimens taken from asthma and non-asthma patients showed significantly higher frequencies of detection of human rhinoviruses in the lower respiratory tract of asthma patients, compared to non-asthma patients. It has also been reported that there is correlation between the presence of rhinovirus and the clinical severity of asthma. In addition, human rhinoviruses cause chronic obstructive pulmonary disease, pneumonia, sinusitis, and otitis media as well as asthma Rhinoviruses are the main causative of the common cold while enterovirus-induced diseases include meningitis, respiratory tract infection, etc. Extensive effort to provide vaccination against poliovirus has significantly reduced the onset of poliomyelitis worldwide, but there are still reports of cases of the disease in Niger, Nigeria, Egypt, India, Pakistan, and Afghanistan. Hepatitis A is now possible to control to some degree thanks to vaccines for hepatitis A viruses. However, no vaccines for coxsackieviruses, echoviruses, or rhinoviruses have been developed, thus far.

Particularly, coxsackievirus B is a main cause of myocarditis, which may develop, in serious cases, into idiopathic dilated cardiomyopathy, which requires heart transplantation.

Enviroxime derivatives are considered the most promising candidate with a broad anti-enterovirus- and anti-rhinovirus activity. Enviroxime interferes with the synthesis of plus-strand RNA by binding to the virus protein 3A that is required for the formation of RNA intermediates in the virus reproduction (Heinz B A and Vance L M: J Virol, 1995, 69(7), 4189-97). In clinical studies, however, the compound was observed to have few or no therapeutic effects, with detection of insufficient pharmacokinetics and unwanted side effects (Miller F D et al.: Antimicrob Agents Chemother, 1985, 27(1), 102-6).

The protease inhibitor AG 7088 has been developed on the basis of the knowledge about the sophisticated structure and function of the viral protease 2C. In the cell culture in the nanomolar concentration range, AG 7088 has shown an effect against 48 rhinovirus types and coxsackievirus A21, B3, enterovirus 70 and echovirus 11 (Pattick A K et al.: Antimicrobila Agents Chemother, 1999, 43(10), 2444-50).

Thanks to the clarification of the molecular structure of the viral capsids, the preconditions for a purposeful design of capsid blockers, the "WIN substances", have been obtained (Diana G D: Curr Med Chem 2003, 2, 1-12). They inhibit the adsorption and/or the uncoating of rhinoviruses and enteroviruses. Some of the WIN substances have a highly specific effect only against individual genera or virus types of the picornaviruses. Other derivatives inhibit the replication both of rhinoviruses and enteroviruses. Arildone, disoxaril and pirodavir belong, for example, to the WIN substances. These compounds showed very good antiviral effects in the cell culture. However, a poor solubility (arildone), low bioavailability (arildone and disoxaril), a rapid metabolization and excretion (disoxaril and WIN 54954) as well as side effects, such as skin rash (WIN 54954), made a clinical application impossible.

Pleconaril, another kind of WIN substance, has a very good oral bioavailability and after its binding to the hydrophobe pocket in the viruscapsid, it inhibits the penetration of rhino-, echo- and coxsackieviruses (Pevear D C et al.: Antimicrob Agents Chemother 1999, 43(9), 2109-15; McKinlay M A et al.: Annu Rev Microbiol 1992, 46, 635-54). Therefore, pleconaril is potentially effective against a broad spectrum of virus diseases, ranging from the common cold to the viral meningitis or myocarditis. Resistances were observed for rhinoviruses, enterovirus 71 and coxsackievirus B3 (Ledford R M et al.: J Virol 2004, 78(7), 3663-74; Groarke J M et al.: J Infect Dis 1999, 179(6), 1538-41). However, the proven therapeutic effect was not sufficient for the registration of pleconaril (Picovir, Viropharma, USA) as an agent for the treatment of rhinovirus infections in the USA. In March 2002, a corresponding application was refused by the Food and Drug Administration (FDA) because therapy success was too low and side effects were observed.

BTA-798 was found to have higher antiviral activity than pleconaril, as evaluated in vitro and in vivo efficacy with rhinoviruses, and is now under clinical study (Ryan, J. et al. Antiviral Res [18th Intl Conf Antiviral Res (April 11-14, Barcelona) 2005] 2005, 65(3): Abst LB-11).

However, no antiviral drugs for use in the treatment of entero- or rhinoviruses have been developed that have gained approval yet.

Thus, while the present inventors were researching antiviral compounds against picornaviruses including coxsackcevirus, enterovirus, echo virus, polio virus and rhino virus, they synthesized the novel compounds expressed by Formula 1 of the present specification and verified that said compounds had excellent antiviral activities against picornaviruses including coxsackievirus, enterovirus, echo virus polio virus and rhino virus to complete the present invention.

DETAILED DESCRIPTION OF THE INVENTION

Technical Objectives

The objective of the present invention is to provide the compound expressed in Formula 1 or Formula 2 of the present specification, as pharmaceutically acceptable salt thereof or an optical isomer thereof.

Another objective of the present invention is to provide a method for preparing the compound expressed in Formula 1 or Formula 2 above.

Still another objective of the present invention is to provide a pharmaceutical composition for prevention or treatment of a viral disease comprised of the compound, the pharmaceutically acceptable salt thereof or the optical isomer thereof as an active ingredient.

Technical Solution

To achieve the above objectives, the present invention provides the compound expressed in Formula 1 or Formula 2 below, a pharmaceutically acceptable salt thereof or an optical isomer thereof.

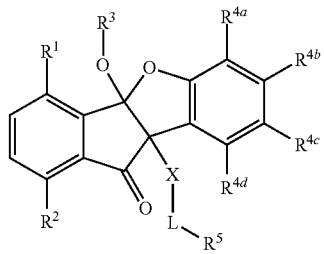

[Formula 1]

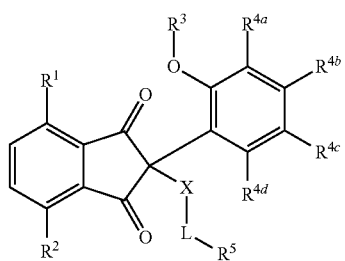

[Formula 2]

In Formulae 1 and 2 above, $R^1$, $R^2$, $R^3$, $R^{4a}$, $R^{4b}$, $R^{4c}$ and $R^{4d}$, X, L and $R^5$ are respectively as defined in the present specification, and the compounds expressed in Formula 1 and Formula 2 above exist in an equilibrium state with each other.

In addition, the present invention provides, as shown in Reaction Equation 1 below, a method for preparing the compound expressed in Formula 1 or Formula 2 above, comprising a step (step 1) in which the compound expressed in Formula 3 or Formula 4 and the compound expressed in Formula 5 are placed in a solvent with a reaction catalyst and then stirred.

[Reaction Equation 1]

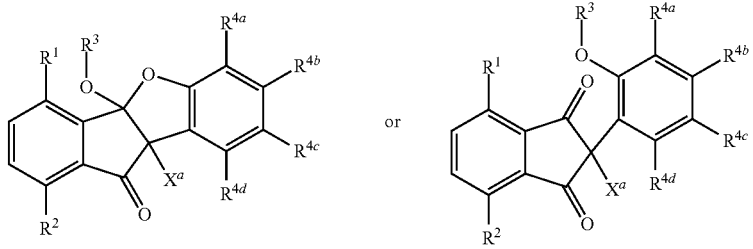

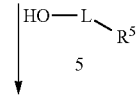

-continued

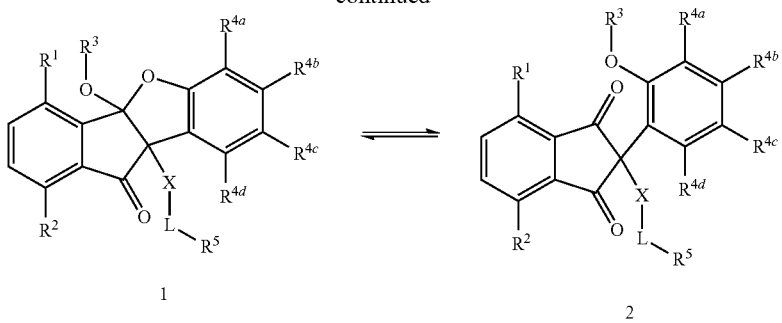

In Reaction Equation 1 above, $X^a$ is —OH or —NH$_2$, and $R^1$, $R^2$, $R^3$, $R^{4a}$, $R^{4b}$, $R^{4c}$ and $R^{4d}$, $R^5$, X and L are respectively as defined in Formulae 1 and 2 above.

Furthermore, the present invention provides a pharmaceutical composition for prevention or treatment of a viral disease containing the compound expressed in Formula 1 or Formula 2 above, the pharmaceutically acceptable salt thereof or the optical isomer thereof as an active ingredient.

Advantageous Effects

The compound expressed in Formula 1 or Formula 2 according to the present invention which is in an equilibrium state with each other has not only low cytotoxicity but also very excellent antiviral activities against picornaviruses including coxsackieviruses, enteroviruses, echoviruses, polioviruses, and rhinoviruses so may be usefully used as the pharmaceutical composition for prevention or treatment of viral diseases including poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

Best Mode for Implementing the Invention

In the following is described the present invention in detail.

The present invention provides the compound expressed in Formula 1 or Formula 2 below, the pharmaceutically acceptable salt thereof or the optical isomer thereof

[Formula 1]

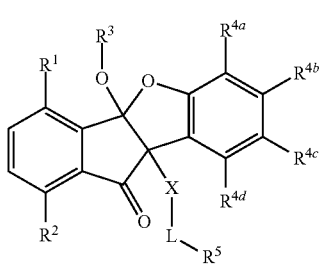

[Formula 2]

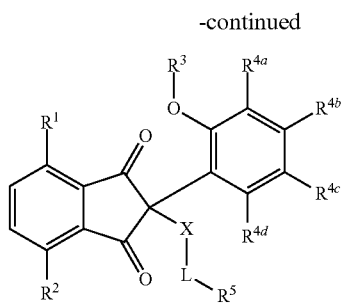

In Formulae 1 and 2 above, $R^1$ is —H, linear or branched $C_{1-6}$ alkyl or —NO$_2$;
$R^2$ is —H, linear or branched $C_{1-6}$ alkyl or —NH$_2$;
$R^3$ is —H, or linear or branched $C_{1-6}$ alkyl;
$R^{4a}$, $R^{4b}$, $R^{4c}$ and $R^{4d}$ are independently —H or linear or branched $C_{1-6}$ alkyl;
X is —O—, —NH— or —NR$^6$—, wherein the $R^6$ is linear or branched $C_{1-6}$ alkyl;
L is a single bond,

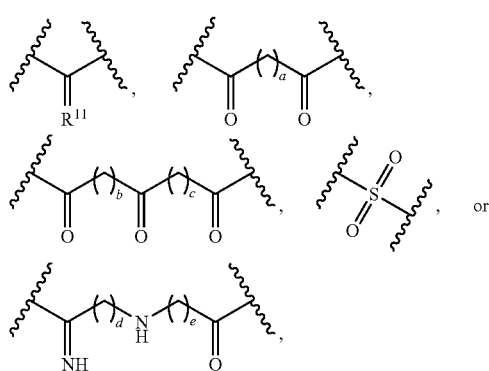

wherein $R^{11}$ is =O, =NH or =S, and a, b, c, d and e are independently integers of 0-5;

$R^5$ is —CN; linear or branched $C_{1-10}$ alkyl; linear or branched $C_{1-10}$ haloalkyl; phenyl; phenyl linear or branched $C_{1-6}$ alkyl; phenyl linear or branched $C_{1-6}$ alkenyl; 5-6 atom heteroaryl including one or more heteroatoms of one or more species selected from a group consisting of N, O and S; 5-8 atom hetero cycloalkyl including one or more heteroatoms of one or more species selected from a group consisting of N, O and S; 5-8 atom heterocycloalkenyl including one or more heteroatoms of one or more species selected from a group consisting of N, O and S;

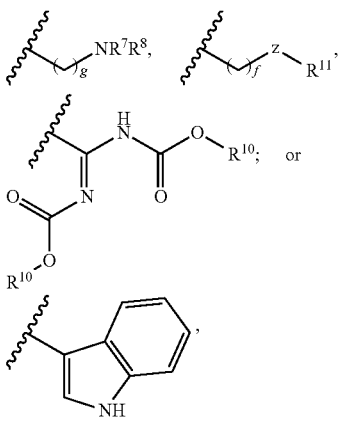

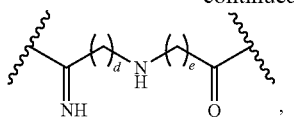

wherein $R^{11}$ is =O, =NH or =S, and wherein a, b, c, d and e are independently integers of 0-3;

$R^5$ is —CN; linear or branched $C_{1-8}$ alkyl; linear or branched $C_{1-8}$ haloalkyl; phenyl,; phenyl linear or branched $C_{1-3}$ alkyl; phenyl linear or branched $C_{1-3}$ alkenyl; 5-6 atom heteroaryl including one or more hetero atoms of one or more species selected from a group consisting of N, O and S; 5-6 atom heterocycloalkyl including one or more heteroatoms of one or more species selected from a group consisting of N, O and S; 5-6 atom heterocycloalkenyl including one or more heteroatoms selected from a group consisting of N, O and S;

wherein the phenyl group in the phenyl, phenyl linear or branched $C_{1-6}$ alkyl, and phenyl linear or branched $C_{1-6}$ alkenyl, may be substituted with one or more substituents of one or more species selected from a group consisting of —OH, halogen, linear or branched $C_{1-6}$ alkyl, linear or branched $C_{1-6}$ alkoxy, and —NO$_2$, wherein the heteroaryl, heterocycloalkyl, and heterocycloalkenyl, may be substituted with one or more substituents of one or more species selected from a group consisting of —OH, halogen and linear or branched $C_{1-6}$ alkyl, $R^7$ and $R^8$ are independently —H, linear or branched $C_{1-6}$ alkyl, non-substituted phenyl, phenyl substituted with one or more linear or branched $C_{1-6}$ alkyl,

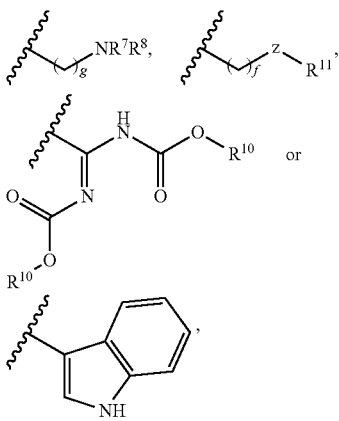

wherein the phenyl group in the phenyl, phenyl linear or branched $C_{1-3}$ alkyl, and phenyl linear or branched $C_{1-3}$ alkenyl, may be substituted with one or more substituents of one or more species selected from a group consisting of —OH, halogen, linear or branched $C_{1-3}$ alkyl, linear or branched $C_{1-3}$ alkoxy, and —NO$_2$, wherein the heteroaryl, heterocycloalkyl, and heterocycloalkenyl may be substituted with one or more substituents selected from a group consisting of —OH, halogen and linear or branched $C_{1-3}$ alkyl, the $R^7$ and $R^8$ are independently —H, linear or branched $C_{1-4}$ alkyl, phenyl that is non-substituted phenyl, phenyl substituted with one or more linear or branched $C_{1-3}$ alkyl,

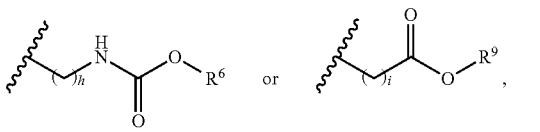

$R^9$, $R^{10}$ and $R^{11}$ are independently —H or linear or branched $C_{1-10}$ alkyl, Z is —O— or —S—, f, g, h and i are independently integers of 0-5; and the compound expressed in Formula 1 and the compound expressed in Formula 2 above exist in a state of equilibrium to each other.

Preferably, the $R^1$ is —H, linear or branched $C_{1-3}$ alkyl or —NO$_2$;

$R^2$ is —H, linear or branched $C_{1-3}$ alkyl or —NH$_2$;

$R^3$ is —H, or linear or branched $C_{1-3}$ alkyl;

$R^{4a}$, $R^{4b}$, $R^{4c}$ and $R^{4d}$ are independently —H or a linear or branched $C_{1-4}$ alkyl;

X is —O—, —NH— or —NR$^6$—, wherein the $R^6$ is a linear or branched $C_{1-3}$ alkyl;

L is a single bond,

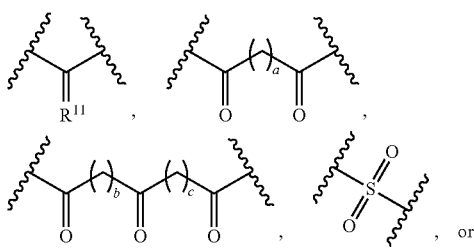

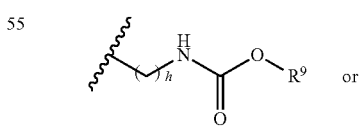

$R^9$, $R^{10}$ and $R^{11}$ are independently —H or linear or branched $C_{1-6}$ alkyl, Z is —O— or —S—, and f, g, h and i are independently integers of 0-3.

More preferably, $R^1$ is —H or —NO$_2$;

$R^2$ is —H or —NH$_2$;

$R^3$ is —H or methyl;

$R^{4a}$, $R^{4b}$, $R^{4c}$ and $R^{4d}$ are independently —H, methyl or isopropyl;

X is —O—, —NH—, or —N(CH$_3$)—;

L is a single bond,

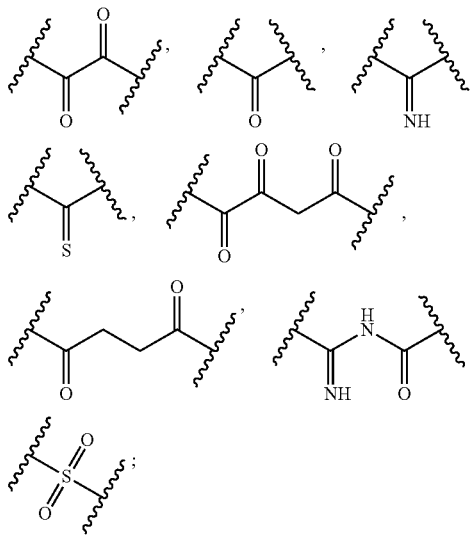

$R^5$ is —CN, linear or branched $C_{1-6}$ alkyl, linear halogen $C_{1-2}$ alkyl, phenyl, phenyl linear $C_{1-2}$ alkyl, phenyl linear $C_2$ alkenyl, 5-6 atom hetero aryl including one or more heteroatoms of one or more species selected from a group consisting of N, O and S, 6 atom heterocycloalkyl including one or more heteroatoms of one or more species selected from a group consisting of N, O and S, 5 atom heterocycloalkenyl including one or more heteroatoms of one or more species selected from a group consisting of N, O and S,

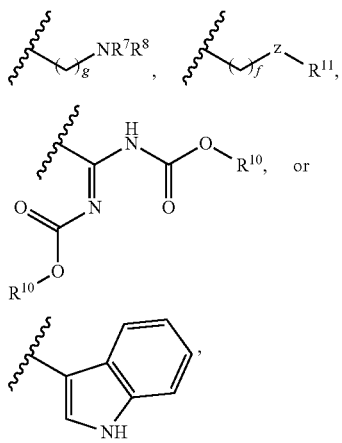

wherein the phenyl group in the phenyl, phenyl linear $C_{1-2}$ alkyl, and phenyl linear $C_2$ alkenyl, may be substituted with one or more substituents of one or more species selected from a group consisting of —OH, methyl, methoxy and —NO$_2$, wherein the heterocycloalkyl may be substituted with methyl, $R^7$ and $R^8$ are independently —H, methyl, ethyl, propyl, isopropyl, dimethyl phenyl,

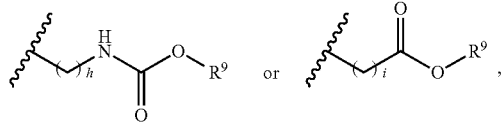

$R^9$, $R^{10}$, and $R^{11}$ are independently —H, methyl, ethyl or t-butyl,

Z is —O— or —S—, and f, g, h and i are independently integers of 0-2.

Examples of the compound expressed in Formula 1 above may include the following compounds:

1) N-(4b-hydroxy-7-isopropyl-10-oxo-9b,10-dihydro-4bH-benzo[d]indeno[1,2-b]furan-9b-yl)-2-(1H-indol-3-yl)-2-oxo acetamide;
2) N-(4b-hydroxy-7-isopropyl-10-oxo-9b,10-dihydro-4bH-indeno[1,2-b]benzofuran-9b-yl)-2-oxo-2-(thiopen-2-yl)acetamide;
3) N-(4b-hydroxy-7-isopropyl-10-oxo-9b,10-dihydro-4bH-indeno[1,2-b]benzofuran-9b-yl)-3-(2-nitro phenyl)-2-oxo propanamide;
4) N-(4b-hydroxy-7-isopropyl-10-oxo-9b,10-dihydro-4bH-indeno[1,2-b]benzofuran-9b-yl)-2-oxo propanamide;
5) N-(4b-hydroxy-7-isopropyl-10-oxo-9b,10-dihydro-4bH-indeno[1,2-b]benzofuran-9b-yl)-2-oxo pentanamide;
6) N-(4b-hydroxy-7-isopropyl-10-oxo-9b,10-dihydro-4bH-indeno[1,2-b]benzofuran-9b-yl)-2-oxo octanamide
7) 2-(furan-2-yl)-6)N-(4b-hydroxy-7-isopropyl-10-oxo-9b,10-dihydro-4bH-indeno[1,2-b]benzofuran-9b-yl)-2-oxo acetamide;
8) N-(4b-hydroxy-7-isopropyl-4-nitro-10-oxo-9b,10-dihydro-4bH-indeno[1,2-b]benzofuran-9b-yl)-2-(1H-indol-3-yl)-2-oxo acetamide;
9) N-(4b-hydroxy-7-isopropyl-10-oxo-9b,10-dihydro-4bH-indeno[1,2-b]benzofuran-9b-yl)-3-(4-hydroxy phenyl)-2-oxo propanamide;
10) N-(1-amino-4b-hydroxy-7-isopropyl-10-oxo-9b,10-dihydro-4bH-indeno[1,2-b]benzofuran-9b-yl)-2-(1H-indol-3-yl)-2-oxo acetamide;
11) N-(1-amino-4b-hydroxy-7-isopropyl-10-oxo-9b,10-dihydro-4bH-indeno[1,2-b]benzofuran-9b-yl)-2-oxo-2-phenyl acetamide;
12) N-(4b-hydroxy-7,8-dimethyl-10-oxo-9b,10-dihydro-4bH-indeno[1,2-b]benzofuran-9b-yl)-2-oxo-2-phenyl acetamide;
13) N-(4b-hydroxy-7,8-dimethyl-10-oxo-9b,10-dihydro-4bH-indeno[1,2-b]benzofuran-9b-yl)-(1H-indol-3-yl)-2-oxo acetamide;
14) N-(4b-hydroxy-7,8-dimethyl-10-oxo-9b,10-dihydro-4bH-indeno[1,2-b]benzofuran-9b-yl)-2-(1H-indol-3-yl)-2-oxo propanamide;
15) N-(4b-hydroxy-7-isopropyl-10-oxo-9b,10-dihydro-4bH-indeno[1,2-b]benzofuran-9b-yl)-2-oxo-2-phenyl acetamide;
16) N-(4b-hydroxy-7-isopropyl-4-nitro-10-oxo-9b,10-dihydro-4bH-indeno[1,2-b]benzofuran-9b-yl)-2-oxo-2-phenyl acetamide;

17) N-(4b-hydroxy-7-isopropyl-10-oxo-9b,10-dihydro-4bH-indeno[1,2-b]benzofuran-9b-yl)-4-(methyl thio)-2-oxo butanamide;
18) 4b-hydroxy-7-isopropyl-10-oxo-4b,10-dihydro-9bH-indeno[1,2-b]benzofuran-9b-ylpropyl carbamate;
19) N-(4b-hydroxy-7-isopropyl-4-nitro-10-oxo-4b,10-dihydro-9bH-indeno[1,2-b]benzofuran-9b-yl)-2-oxo propanamide;
20) N1-(2,6-dimethylphenyl)-N2-(4b-hydroxy-7-isopropyl-10-oxo-4b,10-dihydro-9bH-indeno[1,2-b]benzofuran-9b-yl)oxal amide;
21) N1-(4b-hydroxy-7-isopropyl-10-oxo-4b,10-dihydro-9bH-indeno[1,2-b]benzofuran-9b-yl)-N2,N2-dimethyl oxal amide;
22) N-(1-amino-4b-hydroxy-7-isopropyl-10-oxo-4b,10-dihydro-9bH-indeno[1,2-b]benzofuran-9b-yl)-2-oxo propanamide;
23) N-(4b-hydroxy-7-isopropyl-10-oxo-4b,10-dihydro-9bH-indeno[1,2-b]benzofuran-9b-yl)-2-oxo-2-(3,4,5-trimethoxyphenyl)acetamide;
24) (E)-4-(3,4-dimethoxyphenyl)-N-(4b-hydroxy-7-isopropyl-10-oxo-4b,10-dihydro-9bH-indeno[1,2-b]benzofuran-9b-yl)-2-oxobut-3-enamide;
25) N-(4b-hydroxy-7-isopropyl-4-nitro-10-oxo-4b,10-dihydro-9bH-indeno[1,2-b]benzofuran-9b-yl)-3-(2-nitrophenyl)-2-oxo propanamide;
26) N1-(2,6-dimethylphenyl)-N2-(4b-hydroxy-7-isopropyl-4-nitro-10-oxo-4b,10-dihydro-9bH-indeno[1,2-b] benzofuran-9b-yl) oxal amide;
27) N1-(4b-hydroxy-7-isopropyl-10-oxo-4b,10-dihydro-9bH-indeno[1,2-b]benzofuran-9b-yl)-N2-methyl oxal amide;
28) N-(4b-hydroxy-7-isopropyl-4-nitro-10-oxo-4b,10-dihydro-9bH-indeno[1,2-b]benzofuran-9b-yl)-3 methyl-2-oxo pentanamide;
29) N-(4b-hydroxy-7-isopryl-10-oxo-4b,10-dihydro-9bH-indeno[1,2-b]benzofuran-9b-yl)-3-methyl-2-oxo pentanamide;
30) N1-(4b-hydroxy-7-isopropyl-4-nitro-10-oxo-4b,10-dihydro-9bH-indeno[1,2-b]benzofuran-9b-yl)-N2-N2-dimethyl oxal amide;
31) N1-(1-amino-4b-hydroxy-7-isopropyl-10-oxo-4b,10-dihydro-9bH-indeno[1,2-b]benzofuran-9b-yl)-N2,N2-dimethyl oxal amide;
32) Ethyl 2-((4b-hydroxy-7-isopropyl-10-oxo-4b,10-dihydro-9bH-indeno[1,2-b]benzofuran-9b-yl) amino)-2-oxo acetate;
33) Ethyl 2-((4b-hydroxy-7-isopropyl-4-nitro-10-oxo-4b,10-dihydro-9bH-indeno[1,2-b]benzofuran-9b-yl) amino)-2-oxo acetate;
34) N-(4b-hydroxy-7-isopropyl-4-nitro-10-oxo-4b,10-dihydro-9bH-indeno[1,2-b]benzofuran-9b-yl)-2-oxo pentanamide;
35) N-(4b-hydroxy-7-isopropyl-4-nitro-10-oxo-4b,10-dihydro-9bH-indeno[1,2-b]benzofuran-9b-yl)-2-oxo octanamide;
36) Ethyl 2-((1-amino-4b-hydroxy-7-isopropyl-10-oxo-4b,10-dihydro-9bH-indeno[1,2-b]benzofuran-9b-yl) amino)-2-oxo acetate;
37) N-(4b-hydroxy-7-isopropyl-10-oxo-4b,10-dihydro-9bH-indeno[1,2-b]benzofuran-9b-yl)-3,3-dimethyl-2-oxo butanamide;
38) N-(4b hydroxyl-7-isopropyl-4-nitro-10-oxo-4b,10-dihydro-9bH-indeno[1,2-b]benzofuran-9b-yl)-4-methyl-2-oxo pentanamide;
39) N-(4b-hydroxy-7-isopropyl-10-oxo-4b,10-dihydro-9bH-indeno[1,2-b]benzofuran-9b-yl)-2-oxo-4-phenyl butanamide;
40) N-(1-amino-4b-hydroxy-7-isopropyl-10-oxo-4b,10-dihydro-9bH-indeno[1,2-b]benzofuran-9b-yl)-3-methyl-2-oxo pentanamide;
41) 3-bromo-N-(4b-hydroxy-7-isopropyl-10-oxo-4b,10-dihydro-9bH-indeno[1,2-b]benzofuran-9b-yl)-2-oxo propanamide;
42) N-(4b-hydroxy-7-isopropyl-10-oxo-4b,10-dihydro-9bH-indeno[1,2-b]benzofuran-9b-yl)-2,4-dioxo-4-(pyridyn-4-yl)butanamide;
43) 4-((4b-hydroxy-7-isopropyl-10-oxo-4b,10-dihydro-9bH-indeno[1,2-b]benzofuran-9b-yl)amino)-4-oxo butanoic acid;
44) N1-(4b-hydroxy-7-isopropyl-10-oxo-4b,10-dihydro-9bH-indeno[1,2-b]benzofuran-9b-yl)-N4,N4-dimethyl succinamide;
45) N1-(4b-hydroxy-7-isopropyl-10-oxo-4b,10-dihydro-9bH-indeno[1,2-b]benzofuran-9b-yl)-N4-isopropyl succinamide;
46) N-(4b-hydroxy-7-isopropyl-10-oxo-4b,10-dihydro-9bH-indeno[1,2-b]benzofuran-9b-yl)cyanamide;
47) N1-(4-amino-(4b-hydroxy-7-isopropyl-10-oxo-4b,10-dihydro-9bH-indeno[1,2-b]benzofuran-9b-yl)-N2-(2,6-dimethylphenyl)oxal amide;
48) N-(4b-hydroxy-7-isopropyl-10-oxo-4b,10-dihydro-9bH-indeno[1,2-b]benzofuran-9b-yl)-2-(4-methylpiperazin-1-yl)-2-oxo acetamide;
49) N-(1-amino-(4b-hydroxy-7-isopropyl-10-oxo-4b,10-dihydro-9bH-indeno[1,2-b]benzofuran-9b-yl)-4-methyl-2-oxo pentanamide;
50) N-(1-amino-4b-hydroxy-7-isopropyl-10-oxo-4b,10-dihydro-9bH-indeno[1,2-b]benzofuran-9b-yl)-2-oxo hexanamide;
51) N-(4b-hydroxy-7-isopropyl-1-nitro-10-oxo-4b,10-dihydro-9bH-indeno[1,2-b]benzofuran-9b-yl)-2mesityl-2-oxo acetamide;
52) N-(1-amino-(4b-hydroxy-7-isopropyl-10-oxo-4b,10-dihydro-9bH-indeno[1,2-b]benzofuran-9b-yl)-2-oxo pentanamide;
53) N-(4b-hydroxy-7-isopropyl-4-nitro-10-oxo-4b,10-dihydro-9bH-indeno[1,2-b]benzofuran-9b-yl)-2-oxo-4-phenyl butanamide;
54) N-(1-amino-4b-hydroxy-7-isopropyl-10-oxo-4b,10-dihydro-9bH-indeno[1,2-b]benzofuran-9b-yl)-2-mesityl-2-oxo acetamide;
55) N,N'-di-tert-butoxycarbonyl[1]-(4b-hydroxy-7-isopropyl-10-oxo-4b,10-dihydro-9bH-indeno[1,2-b]benzofuran-9b-yl)]guanidine;
56) Tert-butyl(4b-hydroxy-7-isopropyl-10-oxo-4b,10-dihydro-9bH-indeno[1,2-b]benzofuran-9b-yl)ethan-1,2-diyl dicarbamate;
57) 4-((4b-hydroxy-7-isopropyl-10-oxo-4b,10-dihydro-9bH-indeno[1,2-b]benzofuran-9b-yl)amino)-4-oxo butanoic acid;
58) N-(4b-hydroxy-7-isopropyl-4-nitro-10-oxo-4b,10-dihydro-9bH-indeno[1,2-b]benzofuran-9b-yl)2-oxo-2-(3,4,5-trimethoxyphenyl)acetamide;
59) N-(4b-hydroxy-7-isopropyl-4-nitro-10-oxo-4b,10-dihydro-9bH-indeno[1,2-b]benzofuran-9b-yl)-2-oxo-4-phenyl butanamide;

60) N-(4b-hydroxy-7-isopropyl-10-oxo-4b,10-dihydro-9bH-indeno[1,2-b]benzofuran-9b-yl)acetimide amide;

61) 1-(4b-hydroxy-7-isopropyl-10-oxo-4b,10-dihydro-9bH-indeno[1,2-b]benzofuran-9b-yl)thiourea;

62) 7-isopropyl-4b-methoxy-10-oxo-4b,10-dihydro-9bH-indeno[1,2-b]benzofuran-9b-ylethyl carbamate;

63) tert-butyl(2-((4b-hydroxy-7-isopropyl-10-oxo-4b,10-dihydro-9bH-indeno[1,2-b]benzofuran-9b-yl)amino)-2-oxoethyl)carbamate;

64) 2-amino-N-(4b-hydroxy-7-isopropyl-10-oxo-4b,10-dihydro-9bH-indeno[1,2-b]benzofuran-9b-yl)acetamide;

65) 4b-hydroxy-7,8-dimethyl-9b-(methylamino)-4b,9b-dihydro-10H-indeno[1,2-b]benzofuran-10-one;

66) N-tert butoxy carbonyl[N3-(4b-hydroxy-7-isopropyl-10-oxo-4b,10-dihydro-9bH-indeno[1,2-b]benzofuran-9b-yl)]guanidine;

67) N,N'-di-tertbutoxycarbonyl[1-(4b-hydroxy-7,8-dimethyl-10-oxo-4b,10-dihydro-9bH-indeno[1,2-b]benzofuran-9b-yl-]1-methyl guanidine;

68) N-(4b-hydroxy-7-isopropyl-10-oxo-4b,10-dihydro-9bH-indeno[1,2-b]benzofuran-9b-yl)thiopene-2-sulfonamide;

69) N-(4b-hydroxy-7-isopropyl-4-nitro-10-oxo-4b,10-dihydro-9bH-indeno[1,2-b]benzofuran-9b-yl)benzene sulfonamide;

70) 4b-hydroxy-7,8-dimethyl-9b-(pyridin-2-yl amino)-4b,9b)dihydro-10H-indeno[1,2-b]benzofuran-10-one;

71) N-(4b-hydroxy-7-isopropyl-10-oxo-4b,10-dihydro-9bH-indeno[1,2-b]benzofuran-9b-yl)propane-1-sulfonamide;

72) 1-chloro-N-(4b-hydroxy-7-isopropyl-10-oxo-4b,10-dihydro-9bH-indeno[1,2-b]benzofuran-9b-yl)methane sulfonamide;

73) 9b-((4,5-dihydrothiazol-2-yl) amino)-4b-hydroxy-7-isopropyl-4b,9b-dihydro-10H-indeno-[1,2-b]benzofuran-10-one;

74) 4b-hydroxy-7-isopropyl-9b-(oxazol-2-yl amino)-4b,9b-dihydro-10H-indeno[1,2-b]benzofuran-10-one; and 75) 4b-hydroxy-7-isopropyl-9b-(pyridin-2-yl amino)-4b,9b-dihydro-10H-indeno[1,2-b]benzofuran-10-one.

The compounds expressed in Formula 1 or Formula 2 above of the present invention may be used in the form of pharmaceutically acceptable salts; acid addition salts formed by pharmaceutically acceptable free acids are useful. The expression "pharmaceutically acceptable salt" means any organic or inorganic salt of the basic compounds of Formula 1 or Formula 2 if the side effects caused by the salt at an efficacious concentration that is relatively non-toxic and non-harmful to the patient do not degrade the beneficial efficacy of the basic compounds of Formula 1 or Formula 2.

For the salts in organic acid and organic acids may be used as free acids, and the inorganic acids used may include hydrochloric acid, bromic acid, nitric acid, sulfuric acid, perchloric acid and phosphoric acid and the organic acids used may include citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluenesulfonic acid, salicylic acid, citric acid, benzoic acid, or malonic acid.

In addition, such salts include alkali metal salts (sodium salt, potassium salt, etc.) and alkaline earth metal salts (calcium salts, magnesium salt, etc.). For example, acid addition salts may include acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluoro phosphate, hibenzate, hydrochloride/chloride, hydrobromide/bromide, hydroiodide/iodide, isethionate, lactate, malate, maleate, malonate, mesylate, methyl sulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, alamine, potassium, sodium, tromethamine, and zinc salt, and hydrochloride and trifluoro acetate among them are preferred.

The acid addition salts according to the present invention may be prepared by typical methods. For example, they may be prepared by dissolving the compounds of Formula 1 or Formula 2 in an organic solvent, for example, methanol, ethanol, acetone, methylene chloride, acetonitrile, etc. and then the precipitate formed by adding an organic and or inorganic acid is filtered and dried, or by distilling a solvent and an excess acid under reduced pressure and then drying or recrystallizing it in an organic solvent.

In addition, the pharmaceutically acceptable metal salts may be prepared with bases. Alkali metal salts or alkaline earth metal salts are, for example, obtained by dissolving a compound in an excess alkaline metal hydroxide or an alkaline earth metal hydroxide solution, filtering an undissolved compound salt and then evaporating and drying its filtrate. At this time, it is appropriate pharmaceutically to prepare sodium, potassium or calcium salts as metal salts. In addition, corresponding silver salts may be obtained by reacting the alkali metal or alkaline earth metal salts with suitable silver salt (e.g., silver nitrate).

Furthermore, the present invention includes not only the compounds expressed in Formula 1 or Formula 2 and their pharmaceutically acceptable salts but also solvates, hydrates, isomers, etc. that can be prepared therefrom.

In addition, the present invention provides a method for preparation of the compounds expressed in Formula 1 or Formula 2 above, comprising the step (step 1) as shown in Reaction Equation 1 below in which the compound expressed in Formula 3 or Formula 4 and a compound expressed in Formula 5 are placed in a solvent with a reaction catalyst and then stirred.

[Reaction Equation 1]

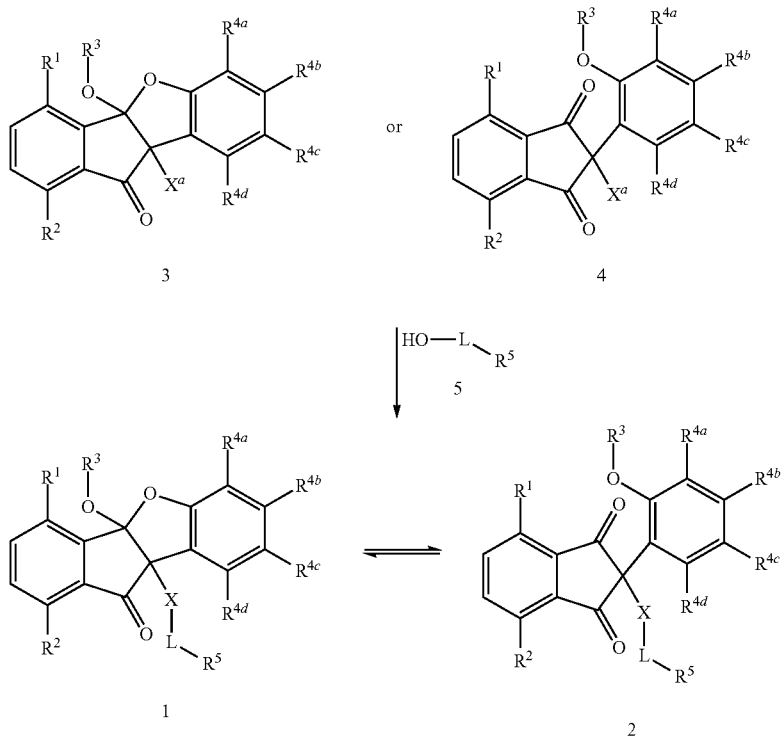

In Reaction Equation 1 above, $X^a$ is —OH or —$NH_2$, and $R^1$, $R^2$, $R^3$, $R^{4a}$, $R^{4b}$, $R^{4c}$, $R^{4d}$, $R^5$, X and L are as defined in Formulae 1 and 2 above.

In the following is described a preparation method of the present invention in detail.

In the preparation method according to the present invention, dimethyl formamide (DMF), methylene chloride (MC), ethanol, water, diisopropyl ether, diethyl ether, dioxane, tetrahydro furan (THF), dimethyl acetamide (DMA), dimethyl sulfoxide (DMSO), chlorobenzene, toluene, benzene and the like may be used independently or mixed and used for the solvent.

In the preparation method according to the present invention, 1-ethyl-3-(3-dimethyl amino propyl) carbodiimide) (EDCI), hydroxyl benzotriazole (HOBt), triethyl amine (TEA), 0-(7-azobenzotriazol-1-yl)-N,N,N',N'-tetramethyl uronium hexafluoro phosphate (HATU), pyridine, $POC_3$, Fe, HCl and the like may be used independently or mixed and used, as the reaction catalyst.

In the preparation method according to the present invention, the reaction temperature of the step 1 is preferably 0-30° C., and the reaction time is preferably 1 hour to 2 days but is not limited to this time.

Further, the present invention provides pharmaceutical compositions for prevention or treatment of viral diseases containing the compounds expressed in Formula 1 or Formula 2 above, pharmaceutically acceptable salts thereof, or optical isomers thereof as active ingredients.

At this time, the viral diseases are diseases caused by picornaviruses including coxsackievirus, enterovirus, poliovirus and rhinovirus. Herein, the viral diseases may include infantile paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina and food-and-mouth disease.

Since the compounds expressed in Formula 1 or Formula 2 that are in equilibrium states with each other according to the present invention have not only low cytotoxicity but also very excellent antiviral activities against picornaviruses including coxsackievirus, enterovirus, poliovirus and rhinovirus, they can be used effectively as pharmaceutical compositions for prevention or treatment of viral diseases including poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

The compounds expressed in Formula 1 or Formula 2 according to the present invention may be administered in the form of various formulations including oral and non-oral clinical administration, and are prepared for formulation using a typical diluent or excipient such as filler, thickening agent, binder, wetting agent, disintegrant, surfactant, and the like.

Solid preparations intended for oral administration include tablets, pills, powders, granules, capsules and troches and such solid preparations are prepared by mixing at least one compound of the present invention with at least one excipient, for example, starch, calcium carbonate, sucrose, lactose, or gelatin. In addition to a simple excipient, a lubricant such as magnesium stearate and talc is also used. While liquid preparations for oral administration include suspensions, internal use solutions, emulsions, syrups and the like, in addition to a simple diluent commonly used such as water, liquid paraffin and the like, various excipients may be included; for example, wetting agents, sweetening agents, aromatics, preservatives, and the like.

Preparations intended for non-oral administration include sterile aqueous solutions, non-aqueous solutions, suspensions, emulsions, lyophilization, suppositories and the like. Propylene glycol, polyethylene glycol, vegetable oils such as olive oil, and esters such as injectable ethyl oleate may be used for the non-aqueous solvents and suspensions. For suppository bases, witepsol, macrogol, tween 61, cacao butter, laurin butter, glycerol, and gelatin may be used.

The compound of the present invention is administered in a therapeutically effective amount. The effective dose of the compound of the present invention varies depending on various factors including a patient's age, weight, sex, dosing method and health condition, and the severity of disease. Typically, the compound of the present invention may be administered at a daily dose of from 0.001 to 100 mg/kg; and preferably at a daily dose of from 0.01 to 35 mg/kg. For an adult with a weight of 70 kg, the dose of the compound of the present invention may typically range from 0.07 to 7,000 mg/day, and preferably from 0.7 to 2,500 mg/day. The formulations of the compound may be administered in a single dose/day or may be divided into multiple doses at regular intervals of time according to the determination of a physician or pharmacist who is responsible for monitoring or observing the administration of the drug.

Mode for Implementation of the Invention

In the following is described the present invention in further detail based on the examples below. However, the examples below merely illustrate the present invention, and details of the present invention are not limited by the examples below.

EXAMPLE 1

Preparation of N-(4b-hydroxy-7-isopropyl-10-oxo-9b,10-dihydro-4bH-benzo[d]indeno[1,2-b]furan-9b-yl)-2-(1H-indol-3-yl)-2-oxo acetamide After 2-(1H-indol-3-yl)-2-oxo acetic acid (352 mg, 1.86 mmol), EDCI (1-ethyl-3-(3-dimethyl amino propyl)carbodiimide) (355 mg, 1.86 mmol), and HOBt (hydroxyl benzotriazole) (251 mg, 1.86 mmol) are dissolved in methylene chloride (MC) (10 ml), and 9b-amino-4b-hydroxy-7-isopropyl-4bH-benzo[d]indeno[1,2-b]furan-10(9bH)-one (500 mg, 1.69 mmol) is added and the mixture is stirred at normal temperature for one day. The reaction mixture is extracted with methylene chloride to collect an organic layer and the layer is dried under $MgSO_4$ and concentrated under reduced pressure. The concentrated compound is purified using silica gel column chromatography (ethyl acetate: n-hexane=1:1) to obtain N-(4b-hydroxy-7-isopropyl-10-oxo-9b,10-dihydro-4bH-benzo[d]indeno[1,2-b]furan-9b-yl)-2-(1H-indol-3-yl)-2-oxo acetamide (199 mg, 25%).

$^1$H-NMR (Acetone, 300 MHz) δ 1.18 (d, J=6.8 Hz, 6H, CH3), 2.87 (sep, J=6.8 Hz, 1H, CH), 6.72 (s, 1H, ArH), 6.93 (d, J=7.9 Hz, 1H, ArH), 7.26-7.29 (m, 2H, ArH), 7.44 (d, J=7.8 Hz, 1H, ArH), 7.54-7.57 (m, 1H, ArH), 7.66-7.75 (m, 1H, ArH), 7.81-7.94 (m, 2H, ArH), 7.99-8.03 (m, 1H, ArH), 8.32-8.35 (m, 1H, ArH), 8.80 (s, 1H, ArH), 11.30 (br, 1H, NH);

466.93 [M+H]+, 933.23 [2M+H]+ for LCMS.

EXAMPLE 2

Preparation of N-(4b-hydroxy-7-isopropyl-10-oxo-9b,10-dihydro-4bH-indeno[1,2-b]benzofuran-9b-yl)-2-oxo-2-(thiopen-2-yl) acetamide After 2-oxo-2-(thiopen-2-yl)acetic acid (107 mg, 1.07 mmol) is dissolved in DMF (3 ml), the temperature is lowered to 0° C. and the solution is stirred. After 10 minutes, triethyl amine (TEA) (213 mg, 1.07 mmol) and HATU (407 mg, 1.07 mmol) are added, and stirred for 10 min before the temperature is lowered to 0° C. and 9b-amino-4b-hydroxy-7-isopropyl-4bH-indeno[1,2-b]benzofuran-10(9bH)-one (300 mg, 1.02 mmol) is added. Next, the temperature is raised to normal temperature, and then the solution is stirred overnight. After washing with water, moisture is removed with $Na_2SO_4$. After filtering and concentration, purification is carried out with column chromatography (EA: Hex=3:7) to obtain the target compound (52 mg, 28%)

$^1$H-NMR (300 MHz, DMSO-d6) δ 1.12 (d, 6H, J=6.0 Hz), 4.13 (q, 1H, J=6.0 Hz), 4.72 (s, 1H), 6.88 (d, 1H, J=6.0 Hz), 7.32 (d, 2H, J=6.0 Hz), 7.63-7.67 (m, 1H), 7.76-7.78 (d–1H), 7.87-7.98 (m, 2H), 8.10 (s, 1H), 8.19 (d, 1H, J=6.0 Hz), 8.56 (s, 1H), 9.56 (s, 1H);

433.75 [M+H]+, 866.87 [2M+H]+ for LCMS.

EXAMPLE 3

Preparation of N-(4b-hydroxy-7-isopropyl-10-oxo-9b,10-dihydro-4bH-indeno[1,2-b]benzofuran-9b-yl)-3-(2-nitrophenyl)-2-oxo propanamide After 2-nitrophenyl pyruvic acid (390 mg, 1.86 mmol) is placed in DMF:DCM (1:2, 15 ml), EDCI (487 mg, 2.54 mmol) is added at 0° C. Next, after 1-hydroxy benzotriazole (343 mg, 2.54 mmol) is added, stirring is carried out at room temperature for 15-30 minutes. Next, after 9b-amino-4b-hydroxy-7-isopropyl-4bH-indeno[1,2-b]benzofuran-10(9bH)-one (500 mg, 1.69 mmol) is added, TEA (0.709 ml, 5.09 mmol) is added. After stirring at 60° C. for two days, water (100 ml) is added. After organic layers are separated with ethyl acetate (70ml×3) they are collected and washed with water (50 ml) and brine (50 ml), moisture is removed with sodium sulfate. After concentration, purification is carried out in a silica gel column chromatography (25% ethyl acetate:hexane) to obtain the target compound 100 mg (24%).

$^1$H-NMR (300 MHz, CDCl$_3$) δ 1.18 (dd, J=2.7 Hz, J=6.9 Hz, 6H, CH3), 2.84 (sept, J=6.9 Hz, 1H, CH), 4.54 (dd, J=19 Hz, J=42 Hz, 2H, CH2), 6.73 (s, 1H, ArH), 6.86 (d, J=7.5 Hz, 1H, ArH), 7.27-7.34 (m, 2H, ArH), 7.46-7.51 (m, 1H, ArH), 7.55-7.62 (m, 2H, ArH), 7.80-7.84 (m, 3H, ArH), 7.51 (d, J=7.8 Hz, 1H, ArH), 8.15 (d, J=8.1 Hz, 1H, ArH);

LCMS: 486.90 (M+H)+.

EXAMPLE 4

Preparation of N-(4b-hydroxy-7-isopropyl-10-oxo-9b,10-dihydro-4bH-indeno[1,2-b]benzofuran-9b-yl)-2-oxo propanamide After adding 9b-amino-4b-hydroxy-7-isopropyl-4bH-indeno[1,2-b]benzofuran-10(9bH)-one (500 mg, 1.69 mmol) in anhydrous DCM (15 ml) and lowering the temperature to 0° C., pyridine (0.276 ml, 3.39 mmol) is added. Then pyruvic acid (0.13 ml, 1.86 mmol) and POCl$_3$ (0.175 ml, 1.86 mmol) are added in that order at 0° C. After stirring at room temperature, organic layers separated using water (100 ml) and DCM (100 ml×2) are collected and washed with dil HCl (1N, 50 ml), water (50 ml) and brine (50 ml) in this order. After removing moisture with anhydrous sodium sulfate and then concentrating, purification is carried out in a flash silica gel column chromatography (25% ethyl acetate in hexane) to obtain the white target compound 130 mg (21%).

$^1$H-NMR (300 MHz, CDCl$_3$) δ 1.18 (dd, J=3.9 Hz, J=6.9 Hz, 6H, CH3), 2.42 (s, 3H, CH3), 2.83 (sept, J=6.9 Hz, 1H, CH), 4.93 (br, 1H, OH), 6.73 (s, 1H, ArH), 6.85 (d, J=7.5 Hz, 1H, ArH), 7.29 (d, J=7.5 Hz, 1H, ArH), 7.56-7.61 (m, 1H, ArH), 7.80-7.84 (m, 2H, ArH), 7.89 (br, 1H, NH), 7.99 (d, J=8.4 Hz, 1H, ArH);
LCMS: 365.92 (M+H)+.

EXAMPLE 5

Preparation of N-(4b-hydroxy-7-isopropyl-10-oxo-9b,10-dihydro-4bH-indeno[1,2-b]benzofuran-9b-yl)-2-oxo pentanamide After adding 9b-amino-4b-hydroxy-7-isopropyl-4bH-indeno[1,2-b]benzofuran-10(9bH)-one (500 mg, 1.69 mmol) in anhydrous DCM (15 ml) and lowering the temperature to 0° C., pyridine (0.276 ml, 3.39 mmol) is added. Then 2-oxa valeric acid (207 mg, 1.78 mmol) and POCl$_3$ (0.175 ml, 1.86 mmol) are added in that order at 0° C. After stirring at room temperature for 15 hours, organic layers separated using water (100 ml) and DCM (100 ml×2) are collected and washed with dil HCl (1N, 50 ml), water (50 ml) and brine (50 ml) in this order. After removing moisture with anhydrous sodium sulfate and them concentrating, purification is carried out in a flash silica gel column chromatography (25% ethyl acetate in hexane) to obtain the white target compound 240 mg (37%).

$^1$H-NMR (300 MHz, CDCl$_3$) δ 0.93 (t, J=7.5 Hz, 3H, CH3), 1.18 (dd, J=2.7 Hz, J=6.9 Hz, 6H, CH3), 1.59-1.69 (m, 2H, CH2), 2.75-2.88 (m, 3H, CH2+CH), 4.88 (br, 1H, OH), 6.73 (s, 1H, ArH), 6.85 (d, J=7.8 Hz, 1H, ArH), 7.28 (d, J=7.8 Hz, 1H, ArH), 7.56-7.61 (m, 1H, ArH), 7.81-7.85 (m, 2H, ArH), 7.93 (br, 1H, NH), 8.00 (d, J=8.1 Hz, 1H, ArH);
LCMS: 393.97 (M+H)+.

EXAMPLE 6

Preparation of N-(4b-hydroxy-7-isopropyl-10-oxo-9b,10-dihydro-4bH-indeno[1,2-b]benzofuran-9b-yl)-2-oxo octanamide After 9b-amino-4b-hydroxy-7-isopropyl-4bH-indeno[1,2-b]benzofuran-10(9bH)-one (500 mg, 1.69 mmol) is added in anhydrous DCM (15 ml), the temperature is lowered to 0° C. After pyridine (0.296 ml, 3.39 mmol) is added, 2-oxa octanoic acid (281 mg, 1.78 mmol) and POCl$_3$ (0.175 ml, 1.86 mmol) are added in that order at 0° C. After stirring at room temperature for 15 hours, organic layers separated using water (100 ml) and DCM (100 ml×2) are collected and washed with dil HCl (1N, 50 ml), water (50 ml) and brine (50 ml) in this order. After removing moisture with anhydrous sodium sulfate and them concentrating, purification is carried out in a flash silica gel column chromatography (15% ethyl acetate in hexane) to obtain the white target compound 140 mg (20%).

$^1$H-NMR (300 MHz, CDCl$_3$) δ 0.86 (t, J=7.2 Hz, 3H, CH3), 1.18 (dd, J=3.0 Hz, J=6.9 Hz, 6H, CH3), 1.26-1.31 (m, 6H, CH2), 1.53-1.60 (m, 2H, CH2), 2.77-2.88 (m, 3H, CH2+CH), 4.90 (br, 1H, OH), 6.73 (s, 1H, ArH), 6.85 (d, J=7.8 Hz, 1H, ArH), 7.28 (d, J=7.8 Hz, 1H, ArH), 7.56-7.61 (m, 1H, ArH), 7.80-7.85 (m, 2H, ArH), 7.98 (br, 1H, NH), 8.00 (d, J=8.4 Hz, 1H, ArH);
LCMS: 435.97 (M+H)+.

EXAMPLE 7

Preparation of 2-(furan-2-yl)-N-(4b-hydroxy-7-isopropyl-10-oxo-9b,10-dihydro-4bH-indeno[1,2-b]benzofuran-9b-yl)-2-oxo acetamide After 2-oxa-2-furyl acetic acid (237 mg, 1.69 mmol) is added in DMF:DCM (1:2, 15 ml), EDCI (487 mg, 2.54 mmol) is added at 0° C. After adding 1-hydroxy benzotriazole (343 mg, 2.54 mmol), stirring is carried out at room temperature for 15-30 min. After adding 9b-amino-4b-hydroxy-7-isopropyl-4bH-indeno[1,2-b]benzofuran-10(9bH)-one (500 mg, 1.69 mmol), stirring is carried out at room temperature for two days. Organic layers separated using water (100 ml) and ethyl acetate (70 ml×3) are collected and then washed with water (50 ml) and brine (50 ml) in that order. After removing moisture with anhydrous sodium sulfate and then concentrating, purification is carried out in a flash silica gel column chromatography (25% ethyl acetate:hexane) to obtain the target compound 40 mg (6%).

$^1$H-NMR (300 MHz, CDCl$_3$) δ 1.18 (d, J=6.9 Hz, 6H, CH3), 2.84 (sept, J=6.9 Hz, 1H, CH), 4.91 (br, 1H, OH), 6.57-6.59 (m, 1H, ArH), 6.75 (s, 1H, ArH), 6.86 (d, J=7.8 Hz, 1H, ArH), 7.33 (d, J=7.8 Hz, 1H, ArH), 7.57-7.62 (m, 1H, ArH), 7.76 (m, 1H, ArH), 7.81-7.87 (m, 2H, ArH), 8.00-8.06 (m, 2H, ArH), 8,23 (br, 1H, NH);
LCMS: 417.90 (M+H)+.

EXAMPLE 8

Preparation of N-(4b-hydroxy-7-isopropyl-4-nitro-10-oxo-9b,10-dihydro-4bH-indeno[1,2-b]benzofuran-9b-yl)-2-(1H-indol-3-yl)-2-oxo acetamide After 3-indol glyoxalic acid (195 mg, 1.03 mmol) is placed in DMF:DCM (1:2, 10 ml), EDCI (296 mg, 1.54 mmol) is added at 0° C.
After 1-hydroxy benzotriazole (205 mg, 1.54 mmol) is added, stirring is carried out at room temperature for 15-30 min. After 9b-amino-4b-hydroxy-7-isopropyl-4bH-indeno[1,2-b]benzofuran-10(9bH)-one (300 mg, 1.03 mmol) is added, stirring is carried out at room temperature overnight. Organic layers separated using water (100 ml) and ethyl acetate (70 ml×3) are collected and then washed with water (50 ml) and brine (50 ml) in that order. After removing moisture with anhydrous sodium sulfate and then concentrating, purification is carried out in a flash silica gel column chromatography (25%, ethyl acetate:hexane) to obtain the white target compound (100 mg, 20%).

$^1$H-NMR (300 MHz, CDCl$_3$) δ 1.19 (dd, J=4.5 Hz, J=6.9 Hz, 6H), 2.86 (sept, J=6.9 Hz, 1H), 6.71 (s, 1H), 6.94 (d, J=8.1 Hz, 1H, ArH), 7.26-7.49 (m, 5H), 8.00-8.17 (m, 4H, ArH), 8.68 (s, 1H), 9.16 (s, 1H);
LCMS: 511.86 (M+H)+.

EXAMPLE 9

Preparation of N-(4b-hydroxy-7-isopropyl-10-oxo-9b,10-dihydro-4bH-indeno[1,2-b]benzofuran-9b-yl)-3-(4-hydroxyphenyl)-2-oxo propanamide After 3-(4-hydroxyphenyl)-2-oxo propanoic acid (97 mg, 0.54 mmol) is dissolved in DMF (3 ml), the temperature is lowered to 0° C. and stirring is carried out. After 10 min, triethyl amine (TEA) (78 mg, 0.77 mmol) and HATU (205 mg, 0.54 mmol) are added. After stirring for 10 min, the temperature is lowered to 0° C., 9b-amino-4b-hydroxy-7-isopropyl-4bH-indeno[1,2-b]benzofuran-10(9bH)-one (150 mg, 0.51 mmol) is added. The temperature is raised to normal temperature, and stirring is carried out overnight. After rinsing with water, moisture is removed with $Na_2SO_4$, and filtering and concentration is carried out, purification is carried out in a column chromatography (EA:Hex=3:7) to obtain the target compound (14 mg, 6%).

$^1$H-NMR (300MHz, CDCls) δ 1.17 (d, 6H, J=6.0 Hz), 2.73-2.90 (m, 1H), 3.98-4.07 (m, 2H), 6.68-6.86 (m, 5H), 7.04 (d, 2H, J=6.0 Hz)7.52-7.59 (m, 2H), 7.80-7.86 (m, 2H), 7.97-8.00 (d, 1H, J=9.0 Hz);

457.83 [M+H]+, 915.14 [2M+H]+ for LCMS

EXAMPLE 10

Preparation of N-(1-amino-4b-hydroxy-7-isopropyl-10-oxo-9b,10-dihydro-4bH-indeno[1,2-b]benzofuran-9b-yl)-2-(1H-indol-3-yl)-2-oxo acetamide After b-hydroxy-7-isopropyl-4-nitro-10-oxo-7b,10-dihydro-4bH-indemo[1,2-b]benzofuran-9b-yl)-2-(1H-inolol-3-yl)-2-oxo acetamide (70 mg, 0.14 mmol) is placed in ethanol:water (10:1, 10 ml:1 ml), the mixture is heated to 60° C. After adding iron (23 mg, 0.41 mmol) and two drops of conc. HCl, heating and refluxing is carried out for 3 hours. After the derived compound is filtered in a celite bed at high temperature, the liquid is washed with ethyl acetate (15 ml×2) and then concentrated before ethyl acetate (100 ml) is added.

After washing with sat. $NaHCO_3$ (20 ml), water (20 ml) and brine (20 ml) in that order, moisture is removed with anhydrous sodium sulfate. After concentration and drying, a small amount of DCM is added and then ultrasonic waves are applied. The solid compound formed at this time is filtered to obtain the yellow target compound (50 mg, 75%).

$^1$H-NMR (300 MHz, $CD_3OD$) δ 1.19 (d, J=6.9 Hz, 6H, CH3), 2.85 (sept, J=6.9 Hz, 1H, CH), 6.67-6.73 (m, 2H, ArH), 6.90 (m, 1H, ArH), 7.03 (m, 1H, ArH), 7.25 (m, 2H, ArH), 7.45 (m, 3H, ArH), 8.29 (m, 1H, ArH), 8.64 (m, 1H, ArH);

LCMS: 481.90 (M+H)+.

EXAMPLE 11

Preparation of N-(1-amino-4b-hydroxy-7-isopropyl-10-oxo-9b,10-dihydro-4bH-indeno[1,2-b]benzofuran-9b-yl)-2-oxo-2-phenyl acetamide After N-(4b-hydroxy-7-isopropyl-4-nitro-10-oxo-9b,10-dihydro-4bH-indeno[1,2-b]benzofuran-9b-yl)-2-oxo-phenyl acetamide (100 mg, 0.21 mmol) is added in ethanol:water (10:1, 10 ml:1 ml), the mixture is heated to 60° C. After iron (36 mg, 0.64 mmol) and two drops of conc. HCl are added, refluxing is carried out by heating for 2 hours. After the derived compound is filtered on a celite bed at high temperature, the liquid is washed with ethyl acetate (15 ml×2) and then concentrated before ethyl acetate (100 ml) is added. After washing it with sat. $NaHCO_3$ (20 ml), water (20 ml) and brine (20 ml) in that order, moisture is removed with anhydrous sodium sulfate. After concentration and drying, a small amount of DCM is added and then ultrasonic waves are applied. The solid compound formed at this time is filtered to obtain the yellow target compound (90 mg, 90%).

$^1$H-NMR (300 MHz, $CD_3OD$) δ 1.17 (d, J-6.9 Hz, 6H, CH3), 2.83 (sept, J=6.9 Hz, 1H, CH), 6.67-6.71 (m, 2H, ArH), 6.87 (d, J=7.5 Hz, 1H, ArH), 7.03 (d, J=7.5 Hz, 1H, ArH), 7.31-7.55 (m, 4H, ArH), 7.64-7.69 (m, 1H, ArH), 8.08-8.16 (m, 2H, ArH);

LCMS: 442.92 (M+H)+.

EXAMPLE 12

Preparation of N-(4b-hydroxy-7,8-dimethyl-10-oxo-9b,10-dihydro-4bH-indeno[1,2-b]benzofuran-9b-yl)-2-oxo-2-phenyl acetamide After dissolving 2-oxo-2-phenyl acetate (281 mg, 1.0 mmol) in DCM (10.0 ml), the temperature is lowered to 0° C. After EDCI (230 mg, 1.2 mmol) is placed at 0° C., stirring is carried out for 10 min. After adding HOBt (162 mg, 1.2 mmol) at 0° C. and then stirring for 10 min, 9b-amino-4b-hydroxy-7,8-dimethyl-4bH-indeno[1,2-b]benzofuran-10 (9bH)-one (281 mg, 1.0 mol) is added at 0° C. and then stirring is carried out at room temperature for 12 hours. After washing with water, removing moisture with $Na_2SO_4$, concentrating under reduced pressure, and purifying in a column, the target compound (219 mg, 53%) is obtained.

$^1$H-NMR (300 MHz, $CDCl_3$) δ 2.17 (s, 3H), 2.19 (s, 3H), 4.87 (s, 1H), 6.68 (s, 1H), 7.18 (s, 1H), 7.42-7.47 (m, 2H), 7.55-7.64 (m, 2H), 7.80-7.85 (m, 2H), 8.01 (d, J=7.56 Hz, 1H), 8.11 (s, 1H) 8.26 (s, 1H), 8.29 (s, 1H); 413.86 [M+H]+, 826.98 [2M+H]+ for LCMS.

EXAMPLE 13

Preparation of N-(4b-hydroxy-7,8-dimethyl -10-oxo-9b,10-dihydro-9bH-indeno[1,2-b]benzofuran-9b-yl)-(1H-indol-3-yl)-2-oxo acetamide After dissolving 2-(1H-indol-3-yl)-2-oxo acetic acid (209 mg, 1.1 mmol) in DCM (10.0 ml), the temperature is lowered to 0° C. After EDCI (230 mg, 1.2 mmol) is placed at 0° C., stirring is carried out for 10 min. After adding HOBt (162 mg, 1.2 mmol) at 0° C. and then stirring for 10 min, 9b-amino-4b-hydroxy-7,8-dimethyl-4bH-indeno[1,2-b]benzofuran-10(9bH)-one (281 mg, 1.0 mol) is added at 0° C. and then stirring is carried out at room temperature for 12 hours. After washing with water, removing moisture with $Na_2SO_4$, concentrating under reduced pressure, and purifying in a column, the target compound (194 mg, 43%) is obtained.

$^1$H-NMR (300 MHz, $CDCl_3$) δ 2.14 (s, 3H), 2.17 (s, 3H), 5.23 (br s, 1H), 6.69 (s, 1H), 7.17 (s, 1H), 7.33 (s, 1H), 7.42 (s, 1H), 7.52-7.94 (m, 4H), 8.40 (s, 1H), 8.53 (s, 1H), 8.87 (s, 2H);

452.83 [M+H]+, 904.95 [2M+H]+ for LCMS.

EXAMPLE 14

Preparation of N-(4b-hydroxy-7,8-dimethyl-10-oxo-9b,10-dihydro-4bH-indeno[1,2-b]benzofuran-9b-yl)-2-oxo propanamide After adding 9b-amino-4b-hydroxy-7,8-dimethyl-4bH-indeno[1,2-b]benzofuran-10(9bH)-one (300 mg, 1.07 mmol) in DCM (20 ml), the temperature is lowered to 0° C. After adding pyridine (168 mg, 2.13 mmol) and stirring for 10 min, 2-oxo propanoic acid (94 mg, 1.07 mmol) is added. After adding $POCl_3$ (0.1 ml, 1.07 mmol) in a stirred state, stirring is carried out at room temperature for 15 hours. After an organic layer is separated using DCM (100 ml) and H$_2$O (100 ml), washing is carried out with 1N HCl and NaCl in that order, moisture is removed with Na$_2$SO$_4$ and concentration is carried out. Next, purification is carried out in a column to obtain the target compound (56 mg, 15%).

$^1$H-NMR (300 MHz-CDCl$_3$) δ 2.16 (s, 3H), 2.18 (s, 3H), 2.44 (s, 3H), 4.86 (br s, 1H), 6.66 (s, 1H), 7.12 (s, 1H), 7.57 (t, J=7.2 Hz, 1H), 7.79-7.82 (m, 2H), 7.92-8.00 (m, 2H);

351.83 [M+H]+, 702.84 [2M+H]+ for LCMS.

EXAMPLE 15

Preparation of N-(4b-hydroxy-7-isopropyl-10-oxo-9b,10-dihydro-4bH-indeno[1,2-b]benzofuran-9b-yl)-2-oxo-2-phenyl acetamide After dissolving phenyl glyoxylic acid (0.30 g, 2.03 mmol) in anhydrous methylene chloride (10 ml), EDCI (0.38 g, 2.03 mmol), HOBt (0.27 g, 2.03 mmol), 3-(2-aminoethyl)-9b-amino-4b-hydroxy-7-isopropyl-4bH-indeno[1,2-b]benzofuran-10(9bH)-one (0.50 g, 1.69 mmol) and triethyl amine (0.25 g, 2.53 mmol) are added and stirring is carried out at room temperature for 24 hours. After diluting with methylene chloride and washing with water several times, the organic layer is dried and filtered. After purifying in a column chromatography (ethyl acetate:hexane=1:2), the target compound (0.20 g, 27%) is obtained.

$^1$H-NMR (300 MHz, CDCl$_3$) δ 1.16-1.19(dd, J=6.9, 3.0 Hz, 2H, CH2) 2.77-2.89(m, 1H, CH) 4.93(s, 1H, OH) 6.75(s, 1H, NH) 6.87(d, J=7.8 Hz, 1H, ArH) 7.44(t, J=8.1 Hz, 2H, ArH) 7.57-7.64(m, 3H, ArH) 7.85(m, 1H, ArH) 8.02(d, J=7.5 Hz, 1H, ArH) 8.09(s, 1H, ArH). 8.26(d, J=7.2 Hz, 2H, ArH);

MS (EI) m/e (rel.intensity) 428(M+H)+, 855(2M+H)+ for LCMS.

EXAMPLE 16

Preparation of N-(4b-hydroxy-7-isopropyl-4-nitro-10-oxo-9b,10-dihydro-4bH-indeno[1,2-b]benzofuran-9b-yl)-2-oxo-2-phenyl acetamide After adding phenyl glyoxalic acid (155 mg, 1.03 mmol) in DMF:DCM (1:2 10 ml), EDCI (296 mg, 1.54 mmol) is added at 0° C. After adding 1-hydroxy benzotrinaole (205 mg, 1.54 mmol), stirring is carried out at room temperature for 15-30 min. After adding 9b-amino-4b-hydroxy-7-isopropyl-4-nitro-4bH-indeno[1,2-b]benzofuran-10(9bH)-one (300 mg, 1.03 mmol), stirring is carried out at room temperature overnight. The organic layers separated using water (100 ml) and ethyl acetate (70 ml×3) are collected and washed with water (50 ml) and brine (50 ml) in that order. After removing moisture with anhydrous sodium sulfate and then concentrating, purification is carried out in a flash silica gel column chromatography (25% ethyl acetate hexane) to obtain the target compound (125 mg, 30%).

$^1$H-NMR (300 MHz, CDCl$_3$) δ 1.19 (dd, J=3.3 Hz, J=6.9 Hz, 6H, CH3), 2.86 (sept, J=6.9 Hz, 1H, CH), 6.50 (s, 1H, OH), 6.73 (s, 1H, ArH), 6.94 (d, J=7.8 Hz, 1H, ArH), 7.41-7.49 (m, 3H, ArH), 7.58-7.63 (m, 2H, ArH+NH), 7.77-7.82 (m, 1H, ArH), 8.26-8.29 (m, 3H, ArH), 8.50 (dd, J=8.1 Hz, J=1 Hz, 1H, ArH);

LCMS: 472.80 (M+H)+.

EXAMPLE 17

Preparation of N-(4b-hydroxy-7-isopropyl-10-oxo-9b,10-dihydro-4bH-indeno[1,2-b]benzofuran-9b-yl)-4-(methylthio)-2-oxo butanamide 9b-amino-4b-hydroxy-7-isopropyl-4bH-indeno[1,2-b]benzofuran-10(9bH)-one (500 mg, 1.7 mmol) and pyridine (269 mg, 3.4 mmol) are dissolved in DCM. After adding POCl$_3$ (286 mg, 1.87 mmol) and then 4-(methylthio)-2-oxo butanoic acid sodium salt (318 mg, 1.87 mmol), stirring is carried out at normal temperature overnight. After washing with water, moisture is removed with Na$_2$SO$_4$, and filtration and concentration is carried out, purification is performed in a column chromatography (EA:Hex=3:7) to obtain the target compound (50 mg, 7%).

$^1$H-NMR (300 MHz, DMSO-d6) δ 1.12 (d, 6H, J=6.0 Hz), 2.53 (s, 3H), 2.78-2.85 (m, 2H), 3.00-3.15 (m, 3H), 6.70 (s, 1H), 6.87 (d, 1H, J=6.0 Hz), 7.28 (d, 1H, J=9.0 Hz), 7.61-7.65 (m, 1H), 7.73 (d, 1H, J=6.0 Hz), 7.87-7.91 (m, 2H).

EXAMPLE 18

Preparation of 4b-hydroxy-7-isopropyl-10-oxo-4b,10-dihydro-9bH-indeno[1,2-b]benzofuran-9b-yl propyl carbamate After dissolving 9b-hydroxy-7-isopropyl-4b-methoxy-4b,9b-dihydro-10H-indeno[1,2-b]benzofuran-10-one (300 mg, 1.0 mmol) in DCM (20 ml), stirring is carried out at 0° C. After dissolving Triphosgene (phosgene) (300 mg, 1.00 mmol) in TEA (0.14 mL, 1.10 mmol), it is added at 0° C. After dissolving the reaction for 10 min and concentrating under reduced pressure, any remaining phosgene is removed. After verifying that the starting material has disappeared using TLC, n-propyl amine (0.05 ml, 2 eq.) and TEA (2 eq.) are added in DCM (20 ml) and dissolved prior to addition. After reacting at normal temperature for 12 hours, the reactants are concentrated upon completion of the reaction and then purification is carried out in a silica gel chromatography (20% EA in Hex) to obtain the target compound (106 mg, 83%).

$^1$H-NMR (300 MHz, CDCl3) δ 0.71 (t, J=7.5 Hz, 3H), 1.18 (dd, J=6.9 Hz, J=3.0 Hz, 6H), 1.38-1.54 (m, 2H), 2.85 (septet J=6.9 Hz, 1H), 3.32-3.37 (m, 2H), 3.89 (s, 1H), 4.47 (s, 1H), 6.73 (s, 1H), 6.87 (d, J=7.8 Hz, 1H), 7.47-7.66 (m, 4H), 7.79 (d, J=7.8 Hz, 1H);

382.29 [M+H]+, 763.96 [2M+H]+ for LCMS.

EXAMPLE 19

Preparation of N-(4b-hydroxy-7-isopropyl-4-nitro-10-oxo-4b,10-dihydro-9bH-indeno[1,2-b]benzofuran-9b-yl)-2-oxo propanamide After dissolving 9b-amino-4b-hydroxy-7-isopropyl-4-nitro-4b,9b-dihydro-10H-indeno[1,2-b]benzofuran-10-one (464 mg, 1.136 mmol) in anhydrous THF (50 ml, 0.02 M), TEA (0.396 ml, 2.839 mmol) is added while stirring slowly. Next, pyruvic acid (100 mg, 1.136 mmol) is added at 10° C. Phosphorous oxy chloride (106 mL, 1,136) is added slowly drop by drop. After reacting at normal temperature for 5 hours, extraction is carried out with ethyl acetate (EA) upon completion of the reaction, washing is carried out with water, water is removed with Na$_2$SO$_4$, and the reactants are concentrated. Next, purification is performed in a silica gel chromatography (15% EA in Hex) to obtain the target compound (70 mg, 15%) and to recover 100 mg of the starting material.

$^1$H-NMR (300 MHz, CDCl3) δ 1.18 (dd, J=6.9 Hz, J=3.0 Hz 6H), 2.43 (s, 3H), 2.85 (sept, J=6.9 Hz, 1H), 6.46 (s, 1H), 6.71 (s, 1H), 6.93 (d, J=7.8 Hz, 1H), 7.43 (d, J=7.8 Hz, 1H), 7.76-7.81 (m, 1H), 8.24 (d, J=7.2 Hz, 1H), 8.50 (d, J=7.8 Hz, 1H);

410.82 [M+H]+, 820.82 [2M+H]+ for LCMS.

EXAMPLE 20

Preparation of N1-(2, 6-dimethylphenyl)-N2-(4b-hydroxy-7-isopropyl-10-oxo-4b,10-dihydro-9bH-indeno[1,2-b]benzofuran-9b-yl)oxal amide After dissolving 2-((2,6-dimethylphenyl)amino)-2-oxo acetic acid (240 mg, 1.24 mmol) is dissolved in DCM (20 ml), EDCI (357 mg, 1.86 mmol) is added at 0° C. while stirring and 1-hydroxy benzotriazole (252 mg, 1.86 mmol) is also added. While stirring, 9b-amino-4b-hydroxy-7-isopropyl-4b,9b-dihydro-10H-indeno[1,2-b]benzofuran-10-one (404 mg, 1.37 mmol) is added, and then the reaction is carried out at normal temperature for 24 hours by adding TEA (0.258 ml, 1.86 mmol) drop by drop. Upon completion of the reaction, water (100 ml) and ethyl acetate (70 ml×2) are used for extraction and then washing is carried out once more with brine (50 ml). After removing water with Na$_2$SO$_4$, the mixture obtained by concentration under pressure is purified in a silica gel column chromatography (15-20% EA in Hex) to obtain the target compound (360 mg, 62%).

$^1$H-NMR (300 MHz, CD3OD) δ 1.16 (d, J=6.9 Hz, 6H), 2.19 (s, 6H), 2.83 (sept, J=6.9 Hz, 1H), 6.68 (s, 1H), 6.90 (d, J=7.2 Hz, 1H), 7.09 (br, 3H), 7.42 (d, J=7.2 Hz, 1H), 7.65-7.90 (br, 4H);

471.29 [M+H]+ for LCMS.

EXAMPLE 21

Preparation of N1-(4b-hydroxy-7-isopropyl-10-oxo-4b,10-dihydro-9bH-indeno[1,2-b]benzofuran-9b-yl)-N2,N2-dimethyl oxal amide After dissolving 2-(dimethylamino)-2-oxo acetic acid (200 mg, 1.71 mmol) in DCM (20 ml), EDCI (654 mg, 3.41 mmol) is added at 0° C. while stirring, and 1-hydroxy benzotriazole (346 mg, 2.56 mmol) is added. While stirring, 9b-amino-4b-hydroxy-7-isopropyl-4b,9b-dihydro-10H-indeno[1,2-b]benzofuran-10-one (605 mg, 2.05 mmol) is added, and then the reaction is carried out at normal temperature for 48 hours by adding TEA (0.357 ml, 2.56 mmol) drop by drop. Upon completion of the reaction, water (100 ml) and ethyl acetate (70 ml×2) are used to extract and then washing is carried out once more with brine (50 ml). After removing water with Na$_2$SO$_4$, the mixture obtained by concentration under pressure is purified in a silica gel column chromatography (50% EA in Hex) to obtain the target compound (450 mg, 67%).

$^1$H-NMR (300 MHz, CD3OD) δ 1.16 (d, J=6.9 Hz, 6H), 2.82 (sept, J=6.9 Hz, 1H), 2.95 (s, 3H), 3.16 (s, 3H), 6.67 (s, 1H), 6.87 (d, J=7.8 Hz, 1H), 7.37 (d, J=7.8 Hz, 1H), 7.62-7.90 (br, 4H);

394.98 [M+H]+, 789.09 [2M+H]+ for LCMS.

EXAMPLE 22

Preparation of N-(1-amino-4b-hydroxy-7-isopropyl-10-oxo-4b,10-dihydro-9bH-indeno[1,2-b]benzofuran-9b-yl)-2-oxo propanamide After dissolving N-(4b-hydroxy-7-isopropyl-4-nitro-10-oxo-4b,10-dihydro-9bH-indeno[1,2-b]benzofuran-9b-yl)-2-oxo propanamide (200 mg, 0.49 mmol) in ethanol:water (10:1, 10 ml), iron (82 mg, 1.46 mmol) is added. After adding conc. HCl (2 drops) and reacting at 90° C. for 2 hours, filtration is carried out with celite under high temperature upon completion of the reaction and then washing is carried out with ethyl acetate. After extracting with DCM and washing with water, washing is carried out with brine (50 ml) again. Water is removed with Na$_2$SO$_4$ and the reactants are concentrated before purification is carried out in a silica gel column chromatography (33% EA in Hex) to obtain the target compound (70 mg, 38%).

$^1$H-NMR (300 MHz, CD3OD) δ 1.18 (d, J=6.9 Hz, 6H), 2.34 (s, 3H), 2.83 (sept, J=6.9 Hz, 1H), 6.66-6.70 (m, 2H), 6.87 (d, J=8.4 Hz, 1H), 6.98 (d, J=8.4 Hz, 1H), 7.34-7.45 (m, 2H);

380.96 [M+H]+ for LCMS.

EXAMPLE 23

Preparation of N-(4b-hydroxy-7-isopropyl-10-oxo-4b,10-dihydro-9bH-indeno[1,2-b]benzofuran-9b-yl)-2-oxo-2-(3,4,5-trimethoxyphenyl)acetamide After 2-oxo-2-(3,4,5-trimethoxyphenyl) acetic acid (25 mg, 0.10 mmol) is dissolved in DCM (1 ml), HATU (59.4 mg, 0.16 mmol) and DIPEA (0.028 ml, 0.16 mmol) are added in sequence while stirring at 0° C. After approximately 5 min, 9b-amino-4b-hydroxy-7-isopropyl-4b,9b-dihydro-10H-indeno[1,2-b]benzofuran-10-one (34 mg, 0.11 mmol) is added and reaction is carried out for 12 hours. Upon completion of the reaction, DCM (50 ml×2) and water are used for extraction and washing is carried out with brine. After removing water with Na$_2$SO$_4$ and then concentrating under reduced pressure, purification is carried out in a silica gel column chromatography (40% EA in Hex) to obtain the target compound (50 mg, 93%).

$^1$H-NMR (300 MHz, CD3OD) δ 1.15 (dd, J=6.9 Hz, J=1.8 Hz, 6H), 2.81 (sept, J=6.9 Hz, 1H), 3.85 (s, 3H), 3.91 (s, 6H), 6.68 (s, 1H), 6.87 (d, J=7.8 Hz, 1H), 7.40 (d, J=7.8 Hz, 1H), 7.50 (s, 2H), 7.57-7.62 (m, 1H), 7.79-7.90 (m, 3H), 7.99 (d, J=7.8 Hz, 1H);

517.85 [M+H]+ for LCMS.

EXAMPLE 24

Preparation of (E)-4-(3,4-dimethoxyphenyl)-N-(4b-hydroxy-7-isopropyl-10-oxo-4b,10-dihydro-9bH-indeno[1,2-b]benzofuran-9b-yl)-2-oxobut-3- enamide After dissolving (E)-4-(3,4-dimethoxy phenyl)-2-oxobut-3-enoic acid (25 mg, 0.11 mmol) in DCM (1 ml), HATU (61 mg, 0.16 mmol) and DIPEA (0.028 ml, 0.16 mmol) is added in that order while stirring at 0° C.

After approximately 5 min, 9b-amino-4b-hydroxy-7-isopropyl-4b,9b-dihydro-10H-indeno[1,2-b]benzofuran-10-one (35 mg, 0.12 mmol) is added and then reaction is carried out for 12 hours. Upon completion of the reaction, DCM (50 ml×2) and water are used for extraction and washing is carried out with brine. After removing water with $Na_2SO_4$ and then concentrating under reduced pressure, purification is carried out in a silica gel column chromatography (40% EA in Hex) to obtain the target compound (40 mg, 74%).

$^1$H-NMR (300 MHz, CD30D) δ 1.16 (d, J=6.9 Hz, 6H), 2.83 (sept, J=6.9 Hz, 1H), 3.84 (s, 3H), 3.86 (s, 3H), 6.68 (s, 1H), 6.90 (d, J=7.8 Hz, 1H), 6.98 (d, J=7.8 Hz, 1H), 7.25 (br, 3H) 7.31 (s, 1H), 7.41 (d, J=7.8 Hz, 1H), 7.59-7.64 (m, 1H), 7.79-7.98 (m, 4H);

513.87 [M+H]+ for LCMS.

EXAMPLE 25

Preparation of N-(4b-hydroxy-7-isopropyl-4-nitro-10-oxo-4b,10-dihydro-9bH-indeno[1,2-b]benzofuran-9b-yl)-3-(2-nitrophenyl)-2-oxo propanamide 3-(2-nitrophenyl)-2-oxo propionic acid (185 mg, 0.88 mmol) is dissolved in DCM (20 ml, 0.044 M). After stirring at 0° C. for 10 min, HATU (502.8 mg, 1.32 mmol) and DIPEA (171 mg, 1.32 mmol) are added. After stirring at 0° C. for 10 min, 9b-amino-4b-hydroxy-7-isopropyl-4-nitro-4b,9b-dihydro-10H-indeno[1,2-b]benzofuran-10-one (300 mg, 0.88 mmol) is added and then stirring is carried out at normal temperature for 18 hours. After extracting with ethyl acetate (EA) and washing with water, the reactant is concentrated and purification is carried out in a silica gel column chromatography (50% EA in Hex) to obtain the target compound (250 mg, 53%).

$^1$H-NMR (300 MHz, CDCl3): δ 1.16-1.19 (m, 6H), 2.80-2.89 (m, 1H), 4.48-4.70 (m, 2H), 6.49 (s, 1H), 6.72 (s, 1H), 6.93 (d, J=9.0 Hz, 1H), 7.30 (d, J=9.0 Hz, 1H), 7.39-7.53 (m, 3H), 7.62 (t, J=9.0 Hz, 1H), 7.80 (t, J=9.0 Hz, 1H), 8.18 (d, J=9.0 Hz, 1H), 8.27 (d, J=9.0 Hz, 1H), 8.52 (d, J=9.0 Hz, 1H);

531.88 [M+H]+ for LCMS.

EXAMPLE 26

Preparation of N1-(2,6-dimethylphenyl)-N2-(4b-hydroxy-7-isopropyl-4-nitro-10-oxo-4b,10-dihydro-9bH-indeno[1,2-b]benzofuran-9b-yl)oxal amide 2-((2,6-dimethylphenyl)amino)-2-oxo acetic acid (170 mg, 0.88 mmol) is dissolved in DCM (20 ml, 0.044 M). After stirring at 0° C. for 10 min, EDCI (253.5 mg, 1.32 mmol) and Hobt (133.8 mg, 1.32 mmol) are added. After stirring at 0° C. for 10 min, TEA (178.6 mg, 1.32 mmol) and 9b-amino-4b-hydroxy-7-isopropyl-4-nitro-4b,9b-dihydro-10H-indeno[1,2-b]benzofuran-10-one (300 mg, 0.88 mmol) is added prior to stirring at normal temperature for 18 hours. After extracting with ethyl acetate (EA) and washing with water, the reactants are concentrated and purified on silica gel column chromatography to obtain the target compound (90 mg, 20%).

$^1$H-NMR (300 MHz, CDCl3): δ 1.17-1.20 (m, 6H), 2.23 (s, 6H) 2.82-2.91 (m, 1H), 6.49 (s, 1H), 6.73 (S, 1H), 6.93-6.95 (m, 1H), 7.08-7.14 (m, 3H), 7.48-7.50 (d, J=6.0 Hz, 1H), 7.81 (t, J=9.0 Hz 1H), 7.95 (s, 1H), 8.27-8.29 (d, J=6.0 Hz, 1H), 8.51-8.53 (m, 2H);

515.97 [M+H]+ for LCMS.

EXAMPLE 27

Preparation of N1-(4b-hydroxy-7-isopropyl-10-oxo-4b,10-dihydro-9bH-indeno[1,2-b]benzofuran-9b-yl)-N2-methyl oxal amide Mono-(N-methyl)-amide oxalate (104.7 mg, 1.02 mmol) is dissolved in DCM (6 ml, 0.1 M). After stirring at 0° C. for 10 min, HATU (386.2 mg, 1.02 mmol) and DIPEA (131 mg, 1.02 mmol) are added. After stirring at 0° C. for 10 min, 9b-amino-4b-hydroxy-7-isopropyl-4b,9b-dihydro-10H-indeno[1,2-b]benzofuran-10-one (200 mg, 0.68 mmol) is added prior to stirring at normal temperature for 18 hours. After stirring further at 50° C. for 3 hours, DMF (6 ml) is added and stirring is carried out again for 1 hour. After extracting with ethyl acetate (EA) and washing with water, the reactants are concentrated and purified on silica gel column chromatography (50% EA in Hex) to obtain the target compound (37 mg, 24%).

$^1$H-NMR (500 MHz, DMSO-d6): δ 1.13 (d, J=7 Hz, 6H), 2.66 (d, J=500 Hz, 3H), 2.79-2.84 (m, 1H), 6.70 (s, 1H), 6.88 (d, J=8 Hz, 1H), 7.27-7.34 (m, 1H), 7.56-7.98 (m, 4H), 8.20-8.30 (m, 1H), 8.46-8.54 (m, 1H), 8.66-8.67 (m, 1H);

380.82 [M+H]+ for LCMS.

EXAMPLE 28

Preparation of N-(4b-hydroxy-7-isopropyl-4-nitro-10-oxo-4b,10-dihydro-9bH-indeno[1,2-b]benzofuran-9b-yl)-3methyl-2-oxo pentanamide After adding and dissolving sodium salt 3-methyl-2-oxo pentanoic acid (300 mgl) is 1N HCl, stirring is carried out for 5 min, extraction is carried out with ethyl acetate, and concentration is carried out under reduced pressure to obtain 3-methyl-2-oxo pentanoic acid (180 mg, 1.38 mmol) which is dissolved in THF (0.1 M, 14 ml). Next, 9b-amino-4b-hydroxy-7-isopropyl-1-nitro-4b,9b-dihydro-10H-indeno[1,2-b]benzofuran-10-one (517 mg, 1.52 mmol) is added, and while stirring is carried out at −10° C. for 15 min, $POCl_3$ (14.0 ml, (0.2 M in THF), 2.76 mmol) is slowly added with a syringe pump for 15 min and stirring is carried out. After adding $POCl_3$, the reaction is carried out at normal temperature for 2 hours, and upon completion of the reaction, concentration is carried out under reduced pressured. EA and water is used to carry out extraction, and the organic layer is washed with water and brine before removing water with $Na_2SO_4$ and concentrating under reduced pressure. Finally, a column filled with silica is used to carry out purification before the target compound (90 mg, 15%) is obtained.

$^1$H-NMR (300 MHz, CDC3): δ 0.84-0.94 (m, 3H), 1.07-1.13 (m, 3H), 1.17-1.21 (m, 6H), 1.30-1.46 (m, 1H), 1.65-1.79 (m, 1H), 2.81-2.90 (m, 1H), 3.31-3.41 (m, 1H), 6.71 (s, 1H), 6.93 (d, J=7.9 Hz, 1H), 7.43 (t, J=7.9 Hz, J=10.2 Hz, 2H), 7.75-7.81 (m, 1H), 8.25 (d, J=7.7 Hz, 1H), 8.49 (d, J=8.0 Hz, 1H);

453.46 [M+H]+ for LCMS.

EXAMPLE 29

Preparation of N-(4b-hydroxy-7-isopryl-10-oxo-4b,10-dihydro-9bH-indeno[1,2-b]benzofuran-9b-yl)-3-methyl-2-oxo pentanamide After adding and dissolving sodium salt 3-methyl-2-oxo pentanoic acid (300 mgl) is 1N HCl, stirring is carried out for 5 min, extraction is carried out with ethyl acetate, and concentration is carried out under reduced pressure to obtain 3-methyl-2-oxo pentanoic acid (180 mg, 1.38 mmol) which is dissolved in THF (0.1 M, 14 ml). Next, 9b-amino-4b-hydroxy-7-isopropyl-4b,9b-dihydro-10H-indeno[1,2-b]benzofuran-10-one (450 mg, 1.52 mmol) is added, and while stirring is carried out at −10° C. for 15 min, $POCl_3$ (14.0 ml, (0.2 M in THF), 2.76 mmol) is slowly added with a syringe pump for 15 min and stirring is carried out. After adding $POCl_3$, the reaction is carried out at normal temperature for 2 hours, and upon completion of the reaction, concentration is carried out under reduced pressured. EA and water is used to carry out extraction, and the organic layer is washed with water and brine before removing water with $Na_2SO_4$ and concentrating under reduced pressure. Finally, a column filled with silica is used to carry out purification before the target compound (190 mg, 30%) is obtained.

$^1$H-NMR (300 MHz, CDCl3): δ 0.82-0.92 (m, 3H), 1.04-1.11 (m 3H), 1.16-1.25 (m, 6H), 1.31-1.42 (m, 1H), 1.63-1.77 (m, 1H), 2.79-2.88 (m, 1H), 3.33-3.39 (m, 1H), 6.84-6.87 (m, 1H), 7.28-7.31 (m, 1H), 7.56-7.61 (m, 1H), 7.80-7.85 (m, 2H), 7.90-7.93 (m, 1H), 8.00 (d, J=7.8 Hz, 1H);

407.97 [M+H]+ for LCMS.

EXAMPLE 30

Preparation of N1-(4b-hydroxy-7-isopropyl-4-nitro-10-oxo-4b,10-dihydro-9bH-indeno[1,2-b]benzofuran-9b-yl)-N2-N2-dimethyl oxal amide While 2-(dimethylamino)-2-oxo acetic acid (180 mg, 1.54 mmol) is added in DCM (0.1 M, 15.0 ml) at 0° C. and stirred, HATU (878 mg, 2.31 mmol) is added and the DIPEA (0.4 ml, 2.31 mmol) is added before stirring is carried out. Finally, 9b-amino-4b-hydroxy-7-isopropyl-1-nitro-4b,9b-dihydro-10H-indeno[1,2-b]benzofuran-10-one (500 mg, 1.69 mmol) is added and then stirring is carried out at normal temperature for 12 hours. Upon completion of the reaction, water and DCM is used for extraction, washing is carried out with water again, and water is removed with $Na_2SO_4$ before concentration is carried out under reduced pressure. Finally, a column filled with silica is used to carry out purification before the target compound (550 mg, 81%) is obtained.

$^1$H-NMR (300 MHz, CDCl3): δ 1.17-1.19 (m, 6H), 1.30-1.46 (m, 1H), 2.81-2.87 (m, 1H), 3.02 (s, 3H), 3.34 (s, 3H), 6.70 (s, 1H), 6.91 (d, J=7.7 Hz, 1H), 7.43 (d, J=7.9 Hz, 1H), 7.75-7.81 (m, 1H), 8.24 (d, J=8.0 Hz, 1H), 8.49 (d, J=8.0 Hz, 1H);

439.88 [M+H]+ for LCMS.

EXAMPLE 31

Preparation of N1-(1-amino-4b-hydroxy-7-isopropyl-10-oxo-4b,10-dihydro-9bH-indeno[1,2-b]benzofuran-9b-yl)-N2,N2-dimethyl oxal amide After dissolving N1-(4b-hydroxy-7-isopropyl-4-nitro-10-oxo-4b,10-dihydro-9bH-indeno[1,2-b]benzofuran-9b-yl)-N2,N2-dimethyl oxal amide (200 mg, 0.46 mmol) is dissolved in EtOH:$H_2O$ (10:1) (0.02 M, 23.0 ml), iron powder (77 mg, 1.38 mmol) is added. While stirring, conc. HCl (3 drops) is slowly added and the reaction is allowed to take placed at 120° C. for 1.5 hours. Upon completion of the reaction, cooling is carried out to normal temperature, concentration under reduced pressure is carried out, water and ethyl acetate is used for extraction, and washing with water is carried out again before water is removed with $Na_2SO_4$ and then concentration is carried out under reduced pressure. Finally, a column filled with silica is used for purification to obtain the target compound (75 mg, 40%).

$^1$H-NMR (300 MHz, CD30D): δ 1.17 (d, J=6.3 Hz, 6H), 2.78-2.87 (m, 1H), 2.94. (s, 3H), 3.16 (s, 3H), 6.65-6.72 (m, 2H), 6.83-6.86 (m, 1H), 6.98-7.00 (m, 1H), 7.35-7.37 (m, 1H), 7.42-7.47 (m, 1H);

409.94 [M+H]+ for LCMS.

EXAMPLE 32

Preparation of Ethyl 2-((4b-hydroxy-7-isopropyl-10-oxo-4b,10-dihydro-9bH-indeno[1,2-b]benzofuran-9b-yl)amino)-2-oxo acetate 9b-amino-4b-hydroxy-7-isopropyl-4b,9b-dihydro-10H-indeno[1,2-b]benzofuran-10-one (0.5 g, 1.69 mmol) is dissolved in THF (17 ml, 0.10 mmol). TEA (0.36 ml, 2.54 mmol) and ethyl-2-chloro-2-oxo acetate (0.17 ml, 1.52 mmol) are slowly added at −10° C. After stirring for 12 hours, THF is concentrated. After adding DCM, washing is carried out with water and brine. After adding $Na_2SO_4$ and filtration, concentration is carried out. A column filled with silica is used for purification to obtain the target compound (400 mg, 60%).

$^1$H-NMR (300 MHz, CDCl3) δ 1.16-1.39 (m, 9H), 2.78-2.87 (m, 1H), 4.31-4.39 (m, 2H).4.91 (br, 1H), 6.73 (s, 1H), 6.84 (d, J=8.1 Hz, 1H), 7.29 (d, J=8.1 Hz, 1H), 7.58 (t, J=7.5 Hz, 1H), 7.80-7.93 (m, 2H), 7.80 (d, J=8.1 Hz, 1H), 8.11 (br, 1H);

396.24 [M+H]+ for LCMS.

EXAMPLE 33

Preparation of Ethyl 2-((4b-hydroxy-7-isopropyl-4-nitro-10-oxo-4b,10-dihydro-9bH-indeno[1,2-b]benzofuran-9b-yl)amino)-2-oxo acetate 9b-amino-4b-hydroxy-7-isopropyl-4b,9b-dihydro-10H-indeno[1,2-b]benzofuran-10-one (0.5 g, 1.47 mmol) is dissolved in THF (15 ml, 0.10 mmol). TEA (0.31 ml, 2.21 mmol) and ethyl-2-chloro-2-oxo acetate (0.15 ml, 1.32 mmol) are slowly added at −10° C. After stirring for 12 hours, THF is concentrated. After adding DCM, washing is carried out with water and brine. After adding $Na_2SO_4$ and filtration, concentration is carried out. A column filled with silica is used for purification to obtain the target compound (240 mg, 60%).

$^1$H-NMR (300 MHz, CDCl3) δ 1.17-1.22 (m, 6H), 1.36 (t, J=7.2 Hz, 3H), 2.79-2.90 (m, 1H), 4.30-4.37 (m, 2H), 6.44-6.53 (m, 1H), 0.71 (br, 1H), 6.93 (d, J=7.8 Hz, 1H), 7.46 (d, J=7.8 Hz, 1H), 7.54 (br, 1H), 7.77 (t, J=7.8 Hz, 1H), 8.21 (d, J=6.6 Hz, 1H), 8.48 (d, J=7.8 Hz, 1H);

441.21 [M+H]+ for LCMS.

Example 34

Preparation of N-(4b-hydroxy-7-isopropyl-4-nitro-10-oxo-4b,10-dihydro-9bH-indeno[1,2-b]benzofuran-9b-yl)-2-oxo pentanamide 2-oxo pentanoic acid (100 mg, 0.86 mmol) is dissolved in THF (17 ml, 0.05 M). Next, 9b-amino-4b-hydroxy-7-isopropyl-4b,9b-dihydro-10H-indeno[1,2-b]benzofuran-10-one (351.2 mg, 1.03 mmol) and TEA (0.30 ml, 2.25 mmol) are added and the temperature is lowered to −10° C. before $POCl_3$ (0.12 ml, 1.29 mmol) is slowly added in drops. While raising the temperature slowly to normal temperature, stirring is carried out for 4 hours and then THF is concentrated. After adding DCM, washing is carried out with water and brine. After adding Na$_2$SO$_4$ and filtration, concentration is carried out. A column filled with silica is used for purification to obtain the target compound (150 mg, 39%).

$^1$H-NMR (300 MHz, CDCl3) δ 0.93 (t, J=7.2 Hz, 3H), 1.16-1.20 (m, 6H), 1.6 (t, J=7.2 Hz, 3H), 1.60-1.67 (m, 2H), 2.81-2.90 (m, 3H), 6.45 (br, 1H), 6.71 (br, 1H), 6.93 (d, J=8.1 Hz, 1H), 7.43 (d, J=7.8 Hz, 2H), 7.78 (t, J=7.8 Hz, 1H), 8.24 (d, J=7.8 Hz, 1H), 8.50 (d, J=8.1 Hz, 1H);

439.25 [M+H]+ for LCMS.

EXAMPLE 35

Preparation of N-(4b-hydroxy-7-isopropyl-4-nitro-10-oxo-4b,10-dihydro-9bH-indeno[1,2-b]benzofuran-9b-yl)-2-oxo octanamide 2-oxo octanoic acid (100 mg, 0.63 mmol) is dissolved in THF (13 ml, 0.05 M). Next, 9b-amino-4b-hydroxy-7-isopropyl-4b,9b-dihydro-10H-indeno[1,2-b]benzofuran-10-one (257.3 mg, 0.76 mmol) and TEA (0.22 ml, 1.58 mmol) are added and the temperature is lowered to −10° C. before POCl$_3$ (0.09 ml, 1.26 mmol) is slowly added in drops. While raising the temperature slowly to normal temperature, stirring is carried out for 4 hours and then THF is concentrated. After adding DCM, washing is carried out with water and brine. After adding Na$_2$SO$_4$ and filtration, concentration is carried out. A column filled with silica is used for purification to obtain the target compound (70 mg, 23%).

$^1$H-NMR (300 MHz, CDCl3) δ 0.82-0.88 (m, 3H), 1.16-1.29 (m, 12H), 1.49-1.62 (m, 3H), 2.81-2.90 (m, 2H), 6.44 (br, 1H), 6.71 (br, 1H), 6.92 (d, J=7.5 Hz, 1H), 7.42 (d, J=8.1 Hz, 2H), 7.78 (t J=8.1 Hz, 1H), 8.24 (d, J=7.5 Hz, 1H), 8.49 (d, J=8.1 Hz, 1H);

481.20 [M+H]+ for LCMS

EXAMPLE 36

Preparation of Ethyl 2-((1-amino-4b-hydroxy-7-isopropyl-10-oxo-4b,10-dihydro-9bH-indeno[1,2-b]benzofuran-9b-yl)amino)-2-oxo acetate Ethyl 2-((4b-hydroxy-7-isopropyl-1-nitro-10-oxo-4b,10-dihydro-9bH-indeno[1,2-b]benzofuran-9b-yl)amino)-2-oxo acetate (100 mg, 0.23 mmol) is dissolved in EtOH:water=10:1 (5 ml, 0.05 M). Fe (38.5 mg, 0.69 mmol) and 1 drop HCl (Cat) is added. Refluxing is carried out for 2 hours. After diluting with ethyl acetate (EA) and then washing with water, its EA layer is extracted. Ethyl acetate is concentrated, and the reactants are dissolved in DCM. After washing with water and brine, Na$_2$SO$_4$ is added, and filtration and concentration is carried out. A column filled with silica is used for purification to obtain the target compound (47 mg, 50%).

$^1$H-NMR (300 MHz, CD3OD) δ 1.17 (d, J=6.9 Hz, 6H), 1.29-1.35 (m, 1H), 4.27-4.34 (m, 2H), 6.67 (s, 2H), 6.87 (d, J=7.8 Hz, 1H), 6.99 (d, J=6.9 Hz, 1H), 7.34-7.47 (m, 2H);

410.7 [M+H]+ for LCMS.

EXAMPLE 37

Preparation of N-(4b-hydroxy-7-isopropyl-10-oxo-4b,10-dihydro-9bH-indeno[1,2-b]benzofuran-9b-yl)-3,3-dimethyl-2-oxo butanamide 9b-amino-4b-hydroxy-7-isopropyl-4b,9b-dihydro-10H-indeno[1,2-b]benzofuran-10-one (500 mg, 1.26 mmol) is added to THF (25 ml, 0.05 M). After adding 3,3-dimethyl-2-oxo butyric acid (137 mg, 1.05 mmol) and then TEA (0.4 ml, 2.64 mmol), cooling is carried out to −10° C. While POCl$_3$ (0.149 mg, 1.56 mmol) is slowly added and the temperature is maintained, stirring is carried out for 3 hours. Concentration is carried out under reduced pressure, ethyl acetate is added in excess, water is removed with Na$_2$SO$_4$, and concentration is carried out under reduced pressure before separation is carried out in a silica gel column chromatography to obtain the target compound (247 mg, 36%).

$^1$H-NMR (300 MHz, CDCl3): δ 1.15 (d, J=6.6 Hz, 6H), 1.24 (s 9H), 2.82 (m, 1H), 5.48 (s, 1H), 6.65 (s, 1H), 6.87 (d, J=7.2 Hz, 1H), 7.34 (d, J=8.4 Hz, 1H), 7.59 (m, 1H), 7.81 (m, 2H), 7.92 (s, 1H);

407.92 [M+H]+ for LCMS.

EXAMPLE 38

Preparation of N-(4b hydroxyl-7-isopropyl-4-nitro-10-oxo-4b,10-dihydro-9bH-indeno[1,2-b]benzofuran-9b-yl)-4-methyl-2-oxo pentanamide 9b-amino-4b-hydroxy-7-isopropyl-1-nitro-4b,9b-dihydro-10H-indeno[1,2-b]benzofuran-10-one (300 mg, 0.88 mmol) is added in DCM (6 ml, 0.15 M). EDCI (340 mg, 1.76 mmol) and TEA (0.4 ml, 2.64 mmol) are added. After adding HOBT (240 mg, 1.76 mmol) and 4-methyl-2-oxo pentanoic acid (120 mg, 0.88 mmol), stirring is carried out at normal temperature for 12 hours. DCM is farther added for dilution and then washing is carried out with water. Water is removed with Na$_2$SO$_4$, concentration is carried out under reduced pressure, and then purification is carried out with silica gel column chromatography to obtain the target compound (68 mg, 16%).

$^1$H-NMR (300 MHz, CDCl3): δ 0.92 (t, J=5.3. Hz, 6H), 1.17 (t, J=3.9 Hz, 6H), 2.16 (m, 2H), 2.70 (m, 2H), 2.74 (m, 2H), 6.70 (s, 1H), 6.92 (d, J=7.9 Hz, 1H), 7.43 (d, J=7.9 Hz, 2H), 7.77 (t, J=7.8 Hz, 1H), 8.23 (d, 5=7.6 Hz, 1H), 8.48 (d, J=7.9 Hz, 1H);

452.90 [M+H]+ for LCMS.

EXAMPLE 39

Preparation of N-(4b-hydroxy-7-isopropyl-10-oxo-4b,10-dihydro-9bH-indeno[1,2-b]benzofuran-9b-yl)-2-oxo-4-phenyl butanamide While 2-oxo-4-phenyl butyric acid (50 mg, 0.28 mmol) is added in DCM (0.1 M, 3.0 ml) at 0° C. and stirred, HATU (160 mg, 0.42 mmol) and then DIPEA (0.07 ml, 0.42 mmol) are added prior to stirring. Finally, 9b-amino-4b-hydroxy-7-isopropyl-4b,9b-dihydro-10H-indeno[1,2-b]benzofuran-10-one (83 mg, 0.28 mmol) is added and stirring is carried out at normal temperature for 12 hours. Upon completion of the reaction, water and DCM are used for extraction and washing with water is carried out again before water is removed with Na2SO4 and then concentration under reduced pressure is carried out. Finally, a column filled with silica is used for purification to obtain the target compound (35 mg, 28%).

$^1$H-NMR (300 MHz, CD3OD): δ 1.15-1.18 (m, 6H), 1.91-.2.15 (m, 2H), 2.72-2.88 (m, 3H), 3.07-3.11 (m, 1H), 6.67 (s, 1H), 6.88-6.90 (m, 1H), 7.14-7.22 (m, 4H), 7.34-7.39 (m, 1H), 7.52-8.03 (m, 5H);
456.51 [M+H]+ for LCMS.

EXAMPLE 40

Preparation of N-(1-amino-4b-hydroxy-7-isopropyl-10-oxo-4b,10-dihydro-9bH-indeno[1,2-b]benzofuran-9b-yl)-3-methyl-2-oxo pentanamide After N-(4b-hydroxy-7-isopropyl-4-nitro-10-oxo-4b,10-dihydro-9bH-indeno[1,2-b]benzofuran-9b-yl)-3-methyl-2-oxo pentanamide (80 mg, 0.18 mmol) is dissolved in EtOH : $H_2O$ (10:1) (0.02 M, 9.0 ml), iron powder (30 mg, 0.54 mmol) is added and stirred before conc. HCl (2 drops) is finally added slowly and then the reaction is carried out at 120° C. for 3 hours.

Upon completion of the reaction, cooling is carried out to normal temperature, concentration under reduced pressure is carried out, water and ethyl acetate are used for extraction, and washing with water is carried out again before water is removed with $Na_2SO_4$ and then concentration is carried out under reduced pressure. Finally, a column filled with silica is used for purification to obtain the target compound (40 mg, 53%).

$^1$H-NMR (300 MHz, CD3OD): δ 0.85-0.94 (m, 3H), 1.04-1.09 (m 3H), 1.18 (d, J=6.7 Hz, 6H), 1.30-1.40 (m, 2H), 2.77-2.89 (m, 1H) 6.65-6.71 (m, 2H), 6.86-6.88 (m, 1H), 6.98-7.01 (m, 1H), 7.32-7.38 (m, 1H), 7.42-7.48 (m, 1H);
422.89 [M+H]+ for LCMS.

EXAMPLE 41

Preparation of 3-bromo-N-(4b-hydroxy-7-isopropyl-10-oxo-4b,10-dihydro-9bH-indeno[1,2-b]benzofuran-9b-yl)-2-oxo propanamide 9b-amino-4b-hydroxy-7-isopropyl-4-nitro-4b,9b-dihydro-10H-indeno[1,2-b]benzofuran-10-one (425 mg, 1.44 mmol) is added in THF (10 ml, 0.1 M). After slowly adding TEA (0.417 ml, 1.29 mmol), 3-bromo-2-oxopropionic acid (200 mg, 1.198 mmol) is added. After cooling to −10° C. and then slowly adding a 0.2 M phosphorous oxy chloride solution (12.0 ml, 2.40 mmol), stirring is carried out for 5-6 hours. Upon completion of the reaction, concentration under reduced pressure is carried out to remove THF and water and ethyl acetate are used for extraction. After washing with water is carried out again, water is removed with $Na_2SO_4$ and concentration under reduced pressure is carried out. Finally, a column filled with silica is used for purification to obtain the target compound (70 mg, 13%).

$^1$H-NMR (300 MHz, CDCl3) δ 1.19 (dd, J=6.9 Hz, J=2.4 Hz, 6H), 2.87 (sept, J=6.9 Hz, 1H), 4.28-4.51 (m, 2H), 6.79 (s, 1H) 6.97 (d, J=8.1 Hz, 1H), 7.64-7.71 (m, 2H), 7.88-7.93 (m, 2H), 8.07 (d, J=7.8 Hz, 1H).

EXAMPLE 42

Preparation of N-(4b-hydroxy-7-isopropyl-10-oxo-4b,10-dihydro-9bH-indeno[1,2-b]benzofuran-9b-yl)-2,4-dioxo-4-(pyridyn-4-yl)butanamide 2,4-dioxo-4-(pyridine-4-yl)butyric acid (25 mg, 0.13 mmol) is added to DCM (1.5 ml) and cooled to 0° C. HATU (74 mg, 0.19 mmol) and DIPEA (0.034 ml, 0.19 mmol) are added. After 5 minutes, 9b-amino-4b-hydroxy-7-isopropyl-4b,9b-dihydro-10H-indeno[1,2-b]benzofuran-10-one (42 mg, 0.14 mmol) is added and then stirring is carried out for 24 hours. Upon quenching with water, DCM (50 ml×2) is added. After water and ethyl acetate is used for extraction and then washing with water is carried out again, water is removed with $Na_2SO_4$ and concentration under reduced pressure is carried out. Finally, a column filled with silica is used (10% MeOH in DCM) for purification to obtain the target compound (45 mg, 74%).

$^1$H-NMR (300 MHz, CD3OD) δ 1.19 (d, J=6.9 Hz, 6H), 2.83 (sept, J=6.9 Hz, 1H), 6.70 (s, 1H), 6.91 (s, 1H), 7.38 (s, 1H) 7.64 (s, 1H), 7.83-7.85 (m, 4H), 7.97 (s, 1H), 8.67-8.76 (m, 2H);
470.77 [M+H]+ for LCMS.

EXAMPLE 43

Preparation of 4-((4b-hydroxy-7-isopropyl-10-oxo-4b,10-dihydro-9bH-indeno[1,2-b]benzofuran-9b-ylamino)-4-oxo butanoic acid 4-((4b-hydroxy-7-isopropyl-10-oxo-4b,10-dihydro-9bH-indeno[1,2-b]benzofuran-9b-yl)amino)-4-oxo butyric acid triethyl amine salt (300 mg, 0.60 mmol) is added in EtOAc (10 ml, 0.06 M). After adding HCl (1 N, 10 ml) at normal temperature, stirring is carried out for 5 min. After water and ethyl acetate are used for extraction and then washing with water is carried out again, water is removed with $Na_2SO_4$ and concentration under reduced pressure is carried out. Finally, a column filled with silica is used for purification to obtain the target compound (240 mg, Quant.).

$^1$H-NMR (300 MHz, CD3OD) δ 1.16 (d, J=6.9 Hz, 6H), 2.53-2.60 (m, 4H), 2.83 (sept, J=6.9 Hz, 1H), 6.87 (d, J=7.8 Hz, 1H), 7.37 (d, J=7.8 Hz, 1H), 7.57-7.60 (m, 1H), 7.74-7.83 (m, 2H), 7.90 (s, 1H);
395.92 [M+H]+ for LCMS.

EXAMPLE 44

Preparation of N1-(4b-hydroxy-7-isopropyl-10-oxo-4b,10-dihydro-9bH-indeno[1,2-b]benzofuran-9b-yl)-N4,N4-dimethyl succinamide 4-((4b-hydroxy-7-isopropyl-10-oxo-4b,10-dihydro-9bH-indeno[1,2-b]benzofuran-9b-yl)amino)-4-oxo butyric acid (100 mg, 0.25 mmol) is added in DCM (2.5 ml) and cooled to 0° C. After HATU (144 mg, 0.38 mmol) and DIPEA (0.110 ml, 0.63 mmol) are added, stirring is carried out for 5 min. After dimethyl amine chloride (25 mg, 0.30 mmol), stirring is carried out for 24 hours. Upon quenching with water, DCM (50 ml×2) is added. After water and ethyl acetate are used for extraction and then washing with water is carried out again, water is removed with $Na_2SO_4$ and concentration under reduced pressure is carried out. Finally, a column filled with silica is used (2:1=EtOAc:Hx) for purification to obtain the target compound (60 mg, 56%).

$^1$H-NMR (300 MHz, CD3OD) δ 1.16 (d, J=6.9 Hz, 6H), 2.59 (m, 4H), 2.81 (sept, J=6.9 Hz, 1H), 2.90 (s, 3H), 3.01 (s, 3H), 6.86 (d, J=7.8 Hz, 1H), 7.36 (d, J=7.8 Hz, 1H), 7.56-7.59 (m, 1H), 7.73-7.82 (m, 2H), 7.90-7.92 (m, 1H);
422.96 [M+H]+, 844.92 [2M+H]+ for LCMS.

EXAMPLE 45

Preparation of N1-(4b-hydroxy-7-isopropyl-10-oxo-4b,10-dihydro-9bH-indeno[1,2-b]benzofuran-9b-yl)-N4-isopropyl succinamide 4-((4b-hydroxy-7-isopropyl-10-oxo-4b,10-dihydro-9bH-indeno[1,2-b]benzofuran-9b-yl)amino)-4-oxo butyric acid (100 mg, 0.25 mmol) is added in DCM (2.5 ml) and cooled to 0° C. After adding HATU (144 mg, 0.38 mmol) and DIPEA (0.066 ml, 0.38 mmol), stirring is carried out for 5 min. After adding isopropyl amine (0.025 ml, 0.30 mmol), stirring is carried out for 24 hours. Upon quenching with water, DCM (50 ml×2) is added. After water and ethyl acetate are used for extraction and then washing with water is carried out again, water is removed with $Na_2SO_4$ and concentration under reduced pressure is carried out. Finally, a column filled with silica is used (DCM:EtOAc=1:1) for purification to obtain the target compound (30 mg, 27%).

$^1$H-NMR (300 MHz, CD30D) δ 1.10 (d, J=6.6 Hz, 6H), 1.16 (d, J=6.9 Hz, 6H), 2.38 (t, J=7.8 Hz, 2H), 2.55 (t, J=7.8 Hz, 2H), 2.82 (sept, J=6.9 Hz, 1H), 3.92 (sept, J=6.6 Hz, 1H) 6.64 (s, 1H), 6.86 (d, J=7.8 Hz, 1H), 7.35 (d, J=7.8 Hz, 1H), 7.53-7.83 (m, 4H);

436.91 [M+H]+, 873.01 [2M+H]+ for LCMS.

EXAMPLE 46

Preparation of N-(4b-hydroxy-7-isopropyl-10-oxo-4b,10-dihydro-9bH-indeno[1,2-b]benzofuran-9b-yl) cyanamide 9b-amino-4b-hydroxy-7-isopropyl-4b,9b-dihydro-10H-indeno[1,2-b]benzofuran-10-one (295 mg, 1.0 mmol) is added in THF (5 ml, 0.1 M) and cooled to 0° C. TEA (0.14 ml, 1.0 mmol) is slowly added. A cyanogen bromide (95.2 mg, 0.9 mmol) solution 5 ml is slowly added for 15 min and stirred. Stirring is carried out at 0° C. for 3 hours. Solid is filtered and separated and the solid is washed with THF. The liquid separated by filtration is concentrated under reduced pressure (DCM/Hx) and recrystallized to obtain the target compound (150 mg, 47%).

$^1$H-NMR (300 MHz, CD30D) ∂ 1.14-1.20 (s, 6H), 2.86 (sept, J=6.9 Hz, 1H), 6.80 (s, 1H), 6.95 (d, J=7.8 Hz, 1H), 7.51 (d, J=7.8 Hz, 1H), 7.67-7.72 (m, 1H), 7.84-8.10 (m, 3H);

320.77 [M+H]+, 640.86 [2M+H]+ for LCMS.

EXAMPLE 47

Preparation of N1-(4-amino-4b-hydroxy-7-isopropyl-10-oxo-4b,10-dihydro-9bH-indeno[1,2-b]benzofuran-9b-yl)-N2-(2,6-dimethylphenyl)oxal amide After adding N1-(2,6-dimmethylphenyl)-N2-(4b-hydroxy-7-isopropyl-4-nitro-10-oxo-4b,10-dihydro-9bH-indeno[1,2-b]benzofuran-9b-yl)oxal amide (70 mg, 0.136 mmol), Fe (23 mg, 0.407 mmol) and HCl (2 drops) are added in the 10:1 10 mL mixture of EtOH and $H_2O$, stirring is carried out at 90° C. for 2 hours. After filtration with celite, concentration is carried out. After diluting with ethyl acetate (EA) and washing with water, the EA layer is extracted. The reactants are concentrated and purification is carried out in a silica gel column chromatography (50% EA in Hex) to obtain the target compound (43 mg, 65%).

$^1$H-NMR (500 MHz, DMSO-d6): δ 1.14 (s, 6H), 2.12 (s-6H), 2.75-2.91 (m, 1H), 6.66-6.70 (m, 3H), 6.85-6.92 (m, 2H), 7.05-7.10 (m, 3H), 8.09 (s, 1H), 8.39 (s, 1H), 10.12 (s, 1H);

485.74 [M+H]+971.09 [2M+H]+ for LCMS.

EXAMPLE 48

Preparation of N-(4b-hydroxy-7-isopropyl-10-oxo-4b,10-dihydro-9bH-indeno[1,2-b]benzofuran-9b-yl)-2-(4-methylpiperazin-1-yl)-2-oxo acetamide After 2-(4-methyl piperazin-1-yl)-2-oxo acetic acid (80 mg, 0.46 mmol) is added in DCM (0.1 M, 5.0 ml) at 0° C. and stirred, HATU (262 mg, 0.69 mmol) and DIPEA (0.12 ml, 0.69 mmol) are added and then stirred. Finally, 9b-amino-4b-hydroxy-7-isopropyl-4b,9b-dihydro-10H-indeno[1,2-b]benzofuran-10-one (150 mg, 0.51 mmol) is added and stirring is carried out at normal temperature for 12 hours. Upon completion of the reaction, the solid formed is filtered and then dissolved in EA again. Water and ethyl acetate are used for extraction and washing is carried out with water before water is removed with $Na_2SO_4$ and concentration under reduced is carried out to obtain the target compound (70 mg, 33%).

$^1$H-NMR (300 MHz, CD30D): δ 1.15 (d, J=6.9 Hz, 6H), 2.54 (s, 3H), 2.79-2.81 (m, 4H), 3.70 (s, 2H), 3.82 (s, 2H), 6.66 (s, 1H), 6.87 (d, J=7.9 Hz, 1H), 7.36 (d, J=7.9 Hz, 1H), 7.71 (s, 2H), 7.84 (s, 2H):

449.86 [M+H]+ for LCMS.

EXAMPLE 49

Preparation of N-(1-amino-4b-hydroxy-7-isopropyl-10-oxo-4b,10-dihydro-9bH-indeno[1,2-b]benzofuran-9b-yl)-4-methyl-2-oxo pentanamide N-(4b-hydroxy-7-isopropyl-1-nitro-10-oxo-4b,10-dihydro-9bH-indeno[1,2-b]benzofuran-9b-yl)-4-methl-2-oxo pentanamide (50 mg, 0.11 mmol) is added in EtOH:$H_2O$ (10:1, 5.5 ml, 0.02 M) and Fe (19 mg, 0.33 mmol) and acetic acid (2 drops) are added before heating and stirring is carried out at 90° C. for 3 hours. A separation tube filled with celite is used to remove Fe and then concentration under reduced pressured is carried out. After ethyl acetate is added in excess, washing with water is carried out, water is removed with $Na_2SO_4$, and concentration under reduced pressure is carried out, separation is carried out in a silica gel column chromatography to obtain target compound (36 mg, 78%).

$^1$H-NMR (300 MHz, CDCl3): δ 0.93 (d, J=4.5 Hz, 6H), 1.16 (d, J=6.8 Hz, 6H), 2.13 (m, 1H), 2.65 (d, J=6.7 Hz, 2H), 2.84 (t, J=3.5 Hz, 1H), 6.67 (d, J=11.0 Hz, 2H), 6.86 (d, J=7.5 Hz, 1H), 6.97 (d, J=7.5 Hz, 1H), 7.34 (d, J=8.0 Hz, 1H), 7.44 (t, 8.1 Hz, 1H);

423.48 [M+H]+ for LCMS.

EXAMPLE 50

Preparation of N-(1-amino-4b-hydroxy-7-isopropyl-10-oxo-4b,10-dihydro-9bH-indeno[1,2-b]benzofuran-9b-yl)-2-oxo hexanamide N-(4b-hydroxy-7-isopropyl-1-nitro-10-oxo-4b,10-dihydro-9bH-indeno[1,2-b]benzofuran-9b-yl)-2-oxo hexanamide (50 mg, 0.11 mmol) is added in EtOH:$H_2O$ (10:1, 5.5 ml, 0.02 M) and Fe (19 mg, 0.33 mmol) and acetic acid (2 drops) are added before heating and stirring is carried out at 90° C. for 3 hours. A separation tube filled with celite is used to remove Fe and then concentration under reduced pressured is carried out. After ethyl acetate is added in excess, washing with water was carried, water is removed with Na$_2$SO$_4$, and concentration under reduced pressure is carried out, separation is carried out in a silica gel column chromatography to obtain target compound (21 mg. 42%).

$^1$H-NMR (300 MHz, CD30D): δ 0.89 (s, 4H), 1.16 (d, J=6.8 Hz 6H), 1.53 (m, 2H), 2.79 (m, 3H), 2.98 (s, 1H), 3.63 (s, 1H), 6.65 (m, 2H, 6.86 (d, J-6.3 Hz, 1H), 6.98 (d, J=6.2 Hz, 1H), 7.33 (m, 1H), 7.44 (m, 1H);

450.01 [M+H]+ for LCMS.

EXAMPLE 51

Preparation of N-(4b-hydroxy-7-isopropyl-1-nitro-10-oxo-4b,10-dihydro-9bH-indeno[1,2-b]benzofuran-9b-yl)-2mesityl-2-oxo acetamide After dissolving mesityl glyoxalic acid (100 mg, 0.52 mmol) is dissolved in DCM (5.2 ml, 0.1 M), HATU (296.6 mg, 0.78 mmol) and DIPEA (0.136 ml, 0.78 mmol) are added. Finally, an amine compound (193.9 mg, 0.57 mmol) is added before stirring is carried out for 12 hours. Upon completion of the reaction, washing is carried out with dichloromethane, NaHCO$_3$ aqueous solution and water and then water is removed with Na$_2$SO$_4$ before concentration under reduced pressure is carried out. Separation is carried out in a silica gel column chromatography to obtain the target compound (91 mg, 34%).

$^1$H-NMR (300 MHz, CD30D) δ 1.17 (d, J=6.6 Hz, 6H), 2.22 (d, J=9.6 Hz, 9H), 6.74 (s, 1H), 6.82 (s, 1H), 6.95 (d, J=7.8 Hz, 2H) 7.44 (d, J=7.8 Hz, 1H), 7.79 (s, 1H), 8.11 (d, J=6.9 Hz, 1H), 8.46 (s, 1H);

515.0 [M+H]+ for LCMS.

EXAMPLE 52

Preparation of N-(1-amino-4b-hydroxy-7-isopropyl-10-oxo-4b,10-dihydro-9bH-indeno[1,2-b]benzofuran-9b-yl)-2-oxo pentanamide N-(4b-hydroxy-7-isopropyl-1-nitro-10-oxo-4b,10-dihydro-9bH-indeno[1,2-b]benzofuran-9b-yl)-2-oxo pentanamide (50 mg, 0.114 mmol) is dissolved in EtOH:water=10:1 (5 ml, 0.02 M) before Fe (19.1 mg, 0.34 mmol) and one drop of HCl (Cat) is added and then stirring is carried out at 90° C. for 4 hours. Upon completion of the reaction, washing is carried out with dichloromethane and water and water is removed with Na$_2$SO$_4$ to obtain the target compound (19.7 mg, 42%) with prep TLC.

$^1$H-NMR (300 MHz, CD30D) δ 0.93 (t, 7.5 Hz, 3H), 1.17 (d6.6 Hz, 6H), 1.28 (br, 1H), 1.57-1.64 (m, 2H), 2.74-2.85 (m, 2H), 6.66-6.70 (m, 2H), 6.86 (d, J=7.5 Hz, 1H), 6.99 (d, J=7.5 Hz, 1H) 7.35 (d, J=7.5 Hz, 1H), 7.43-4.47 (m, 1H);

409.8 [M+H]+ for LCMS.

EXAMPLE 53

Preparation of N-(4b-hydroxy-7-isopropyl-4-nitro-10-oxo-4b,10-dihydro-9bH-indeno[1,2-b]benzofuran-9b-yl)-2-oxo-4-phenyl butanamide After dissolving 2-oxo-4-phenyl butyric acid (50 mg, 0.28 mmol) in DCM (2.81 ml, 0.1 M), HATU (160 mg, 0.42 mmol) and DIPEA (0.073 ml, 0.42 mmol) are added, and a nitro compound (105.1 mg, 0.31 mmol) is added, and then stirring is carried out at room temperature for 12 hours. Upon completion of the reaction, dichloromethane, an NaHCO$_3$ aqueous solution, and water are used for washing before water is removed with Na$_2$SO$_4$ and separation is carried out in a silica gel column chromatography to obtain the target compound (35 mg, 25%).

$^1$H-NMR (300 MHz, CD30D) δ 1.18 (d, J=6.3 Hz, 6H), 2.82- 2.93 (m, 4H), 3.10-3.11 (m, 1H), 6.73 (s, 1H), 6.94 (d, 1=7.2 Hz, 1H), 7.14-7.26 (m, 5H), 7.39 (t, 7.2 Hz, 1H), 7.86-7.89 (m, 1H), 8.51-8.55 (m, 1H);

501.51 [M+H]+ for LCMS.

EXAMPLE 54

Preparation of N-(1-amino-4b-hydroxy-7-isopropyl-10-oxo-4b,10-dihydro-9bH-indeno[1,2-b]benzofuran-9b-yl)-2-mesityl-2-oxo acetamide N-(4b-hydroxy-7-isopropyl-1-nitro-10-oxo-4b,10-dihydro-9bH-indeno[1,2-b]benzofuran-9b-yl)-2-oxo pentanamide (50 mg, 0.114 mmol) is dissolved in EtOH:water=10:1 (5 ml, 0.02 M) before Fe (19.1 mg, 0.34 mmol) and one drop of HCl (Cat) are added and then stirring is carried out at 90° C. for 4 hours. Upon completion of the reaction, washing is carried out with dichloromethane and water and prep TLC is used to obtain the target compound (19.7 mg, 42%).

$^1$H-NMR (300 MHz, CD30D) δ 1.88 (d, J=6.6 Hz, 6H), 2.23 (d, J=9.6 Hz, 9H), 2.79-2.86 (m, 1H), 6.65 (d, 7.5 Hz, 2H), 6.83 (s, 2H), 6.89 (d, J=7.5 Hz, 1H), 6.98 (d, J=7.5 Hz, 1H), 7.41 (t, J=8.1 Hz, 2H);

485.8 [M+H]+ for LCMS.

EXAMPLE 55

Preparation of N,N'-di-tert-butoxycarbonyl[1]-(4b-hydroxy-7-isopropyl-10-oxo-4b,10-dihydro-9bH-indeno[1,2-b]benzofuran-9b-yl)]guanidine In 9b-amino-4b-hydroxy-7-isopropyl-4b,9b-dihydro-10H-indeno[1,2-b]benzofuran-10-one (295 mg, 1.00 mmol) is added DMF (5 ml, 0.2 M) and 1,3-bis(tert-butoxy carbonyl)-2-methyl-2-thiopseudo urea (305 mg, 1.05 mmol). After adding HgCl$_2$ (298 mg, 1.10 mmol) and then adding triethyl amine (0.31 ml, 2.20 mmol) at 0° C., stirring is carried out for 90 min.

Upon completion of the reaction, ethyl acetate (50 ml) is added and then filtration is carried out on celite. After washing the filtrate with water and brine, water is removed with Na$_2$SO$_4$ and then separation is carried out in a silica gel column chromatography (10% ethyl acetate in hexanes) to obtain the target compound (94 mg, 18%).

$^1$H-NMR (300 MHz, CD30D) δ 1.18 (d, J=6.9 Hz, 6H), 1.20 (s, 9H), 1.51 (s, 9H), 2.82 (sept, J=6.9 Hz, 1H), 6.66 (s, 1H), 6.87 (br, 1H), 7.34 (br, 1H), 7.72-7.84 (m, 4H);

537.89 [M+H]+ for LCMS.

EXAMPLE 56

Preparation of Tert-butyl(4b-hydroxy-7-isopropyl-10-oxo-4b,10-dihydro-9bH-indeno[1,2-b]benzofuran-9b-yl)ethan-1,2-diyl dicarbamate In 7-isopropyl-10H-4b,9b-(epoxymetanooxy)indeno[1,2-b]benzofuran-10,12-dione (170 mg, 0.5 mmol) is added THF:DMF (8:1) and tert-butyl (2-aminoethyl)carbamate (80 mg, 0.50 mmol). Afterward DMAP (2-3 mg) and TEA (0.14 ml, 1.11 mmol) are added before stirring is carried out at room temperature for 6 hours. Upon completion of the reaction, concentration under reduced pressure is carried out and then separation is carried out in a silica gel column chromatography (20% EtAc in hexane) to obtain the target compound (200 mg, 83%).

$^1$H-NMR (300 MHz, CDCl3) δ 1.15 (dd, J=6.9 Hz, J=2.4 Hz, 6H), 1.41 (s, 9H), 2.80 (septet, J=6.9 Hz, 1H), 3.12-3.22 (m, 4H), 5.03 (s, 1H), 6.65 (s, 1H), 6.77 (d, J=7.8 Hz, 1H), 7.34 (d, J=7.8 Hz, 1H), 7.48-7.53 (m, 1H), 7.70-7.79 (m, 2H), 7.87 (d, J=7.5 Hz, 1H);

483.23 [M+H]+, 966.40 [2M+H]+ for LCMS.

EXAMPLE 57

Preparation of 4-((4b-hydroxy-7-isopropyl-10-oxo-4b,10-dihydro-9bH-indeno[1,2-b]benzofuran-9b-yl) amino)-4-oxo butanoic acid In 9b-amino-4b-hydroxy-7-isopropyl-4b,9b-dihydro-10H-indeno[1,2-b]benzofuran-10-one (295 mg, 1.0 mmol) and anhydrous succinic acid are added dry THF (10 ml, 0.1 M) and TEA (0.167 ml, 1.20 mmol). After adding DMAP (10 mg), stirring is carried out in a refluxing apparatus for 8 hours. Upon completion of the reaction, cooling to room temperature is carried out and then solid is filtered. The filtrate is washed with THF to obtain the target compound (360 mg, 73%).

$^1$H-NMR (300 MHz, DMSO-d6) δ 0.97 (t, J=7.2 Hz, 9H), 1.11 (d, J=6.9 Hz, 6H), 2.28-2.30 (m, 2H), 2.38-2.40 (m, 2H), 2.51-2.55 (m, 6H), 2.79 (sept, J=6.9 Hz, 1H), 6.64 (s, 1H), 6.85 (d, J=7.8 Hz, 1H), 7.73-7.77 (ra, 4H), 8.72 (br, 1H);

395.85 [M+H]+ for LCMS.

EXAMPLE 58

Preparation of N-(4b-hydroxy-7-isopropyl-4-nitro-10-oxo-4b,10-dihydro-9bH-indeno[1,2-b]benzo-furan-9b-yl)2-oxo-2-(3,4,5- trimethoxyphenyl)acet-amide After 9b-amino-4b-hydroxy-7-isopropyl-4-nitro-4b,9b-dihydro-10H-indeno[1,2-b]benzofuran-10-one (72 mg, 0.21 mmol) is added in DMF (3 ml, 0. 1 mmol), HATU (118 mg, 0.31 mmol) and DIPEA (0.6 ml, 0.31 mmol) are added. After adding 2-oxo-2-(3,4,5-trimethoxyphenyl)acetic acid (50 mg, 0.21 mg), stirring is carried out at normal temperature for 5 hours. After adding DCM in excess and washing with water, water is removed with $Na_2SO_4$ and then concentration under reduced pressure is carried out. Separation is carried out in a silica gel column chromatography to obtain the target compound (55 mg, 46%).

$^1$H-NMR (300 MHz, CDCl3): δ 1.19 (d, J=10.0 Hz, 6H), 2.16 (s, 9H), 2.84 (m, 1H), 6.49 (s, 1H), 6.72 (s, 1H), 6.94 (d, J=7.9 Hz, 1H), 7.46 (d, J=7.9 Hz, 1H), 7.60 (s, 1H), 7.65 (s, 2H), 7.79 (t, J=7.8 Hz, 1H), 8.27 (d, J=7.6 Hz, 1H), 8.49 (d, J=8.0 Hz, 1H);

562.79 [M+H]+ for LCMS.

EXAMPLE 59

Preparation of N-(4b-hydroxy-7-isopropyl-4-nitro-10-oxo-4b,10-dihydro-9bH-indeno[1,2-b]benzo-furan-9b-yl)-2-oxo-4-phenyl butanamide After dissolving N-(4b-hydroxy-7-isopropyl-4-nitro-10-oxo-4b,10-dihydro-9bH-indeno[1,2-b]benzofuran-9b-yl)-2-oxo-4-phenyl butanamide (50 mg, 0.10 mmol) in ECOH: water=10:1 (2 ml, 0.05 M), Fe (16.7 mg, 0.30 mmol) is added and then stirred. Lastly, one drop of HCl is added and then stirring is carried out at 90° C. for 12 hours. Upon completion of the reaction, cooling to normal temperature is carried out and then concentration under reduced pressure is carried out. Water and ethyl acetate are used for extraction before washing with water, removing water with $Na_2SO_4$, and concentration under reduced pressure. Finally, a column filled with silica is used for purification to obtain the target compound (20 mg 43%).

$^1$H-NMR (300 MHz, CD30D) δ 1.17 (d, J=6.3 Hz, 6H), 2.74- 2.97 (m, 4H), 3.06-3.13 (m, 1H), 6.66-6.69 (m, 2H), 6.87 (d, J=7.2 Hz, 1H), 6.99 (t, J=7.2 Hz, 1H), 7.14-7.23 (m, 5H), 7.35 (d, J=7.8 Hz, 1H), 7.44 (t, J=7.8 Hz, 1H);

471.9 [M+H]+ for LCMS.

EXAMPLE 60

Preparation of N-(4b-hydroxy-7-isopropyl-10-oxo-4b,10-dihydro-9bH-indeno[1,2-b]benzofuran-9b-yl) acetimide amide After dissolving 9b-amino-4b-hydroxy-7-isopropyl-4b, 9b-dihydro-10H-indeno[1,2-b]benzofuran-10-one (150 mg, 0.5 mmol) in acetonitrile (ACN) (5 ml, 0.1 M), stirring is carried out while adding ethyl acetamidate (189 mg, 1.5 mmol).

After adding DIPEA (0.02 ml, 1.27 mmol), refluxing is carried out for 12 hours. Upon completion of the reaction, cooling to normal temperature is carried out and then concentration under reduced pressure is carried out. Water and ethyl acetate are used for extraction before washing with water, removing water with $Na_2SO_4$, and concentration under reduced pressure. Finally, DCM/Hx is added to the mixture for recrystallization to obtain the target compound (38 mg, 23%).

$^1$H-NMR (300 MHz, CD30D) δ 1.19 (d, J=6.9 Hz, 6H), 1.96 (s, 3H), 2.81 (sept, J=6.9 Hz, 1H), 6.60 (s, 1H), 6.79 (d, J=8.1 Hz, 1H), 7.30 (d, J=8.1 Hz, 1H), 7.52-7.54 (m, 1H), 7.73-7.80 (m, 3H);

336.88 [M+H]+ for LCMS.

EXAMPLE 61

Preparation of 1-(4b-hydroxy-7-isopropyl-10-oxo-4b,10-dihydro-9bH-indeno[1,2-b]benzofuran-9b-yl) thiourea After dissolving 9b-amino-4b-hydroxy-7-isopropyl-4b, 9b-dihydro-10H-indeno[1,2-b]benzofuran-10-one (2.95 g, 10.0 mmol) in acetone:water (2:1, 100 ml), potassium thiocyanate (4.86 g, 49.99 mmol) are added. After adding conc. HCl (5 ml), stirring is carried out at normal temperature for 12 hours. Upon completion of the reaction, water and ethyl acetate are used for extraction and then washing with brine is carried out again. After removing water with $Na_2SO_4$ and then concentrating under reduced pressure, the mixture obtained is purified in a silica gel column chromatography (33% EA in Hex) to obtain the target compound (2.64 g, 75%).

$^1$H-NMR (300 MHz, CD30D) δ 1.50-1.22 (m, 6H), 2.83 (sept, J=6.9 Hz, 1H), 6.61 (s, 1H), 6.86 (d, J=8.1 Hz, 1H), 7.35-7.89 (m, 5H);

354.87 [M+H]+, 708.97 [2M+H]+ for LCMS.

EXAMPLE 62

Preparation of 7-isopropyl-4b-methoxy-10-oxo-4b, 10-dihydro-9bH-indeno[1,2-b]benzofuran-9b-ylethyl carbamate 9b-hydroxy-7-isopropyl-4b-methoxy-4b,9b-dihydro-10H-indeno[1,2-b]benzofuran-10-one (950 mg, 3.07 mmol) is added in DCM (12 ml) at 0° C. and stirred before triphosgene (909 mg, 3.07 mmol) is dissolved in TEA (0.43 ml, 3.07 mmol) and then slowly added. After approximately 10 min, concentration under reduced pressure is carried out to remove any excess phosgene and then DCM (12 ml) is again dissolved before a solution (0.77 ml, 1.53 mmol) prepared by mixing ethyl amine with methanol (2.0 M) is added and then TEA (0.43 ml, 3.07 mmol) is added. After reacting at normal temperature for 2 hours, water and DCM are used for extraction and washing with brine is carried out again. After removing water with $Na_2SO_4$ and then concentrating under reduced pressure, the mixture obtained is purified in a silica gel column chromatography (10% EA in Hex) to obtain the target compound (350 mg, 60%).

$^1$H-NMR (300 MHz, CDCl3) δ 1.09 (t, J=7.2 Hz, 3H), 1.20 (dd, J=6.9 Hz, J=4.8 Hz, 6H) 2.87 (septet, J=6.9 Hz, 1H), 3.44-3.55 (m, 2H), 3.65 (s, 1H), 3.71 (s, 3H), 6.77 (s, 1H), 6.88-6.91 (d, J=9 Hz, 1H), 7.46-7.55 (m, 3H), 7.61 (d, J=7.8 Hz, 1H), 7.72 (d, J=7.2 Hz, 1H);

382.29 [M+H]+ for LCMS.

EXAMPLE 63

Preparation of tert-butyl(2-((4b-hydroxy-7-isopropyl-10-oxo-4b,10-dihydro-9bH-indeno[1,2-b]benzofuran-9b-yl)amino)-2-oxoethyl)carbamate While glycine (650 mg, 3.72 mmol) is dissolved in DCM (20 ml, 0.2 M) at 0° C. and then stirred, HATU (1.54 g, 4.06 mmol) and DIPEA (0.734 ml, 4.06 mmol) are added to carry out the reaction. After approximately 5 min, 9b-amino-4b-hydroxy-7-isopropyl-4b,9b-dihydro-10H-indeno[1,2-b]benzofuran-10-one (0.025 ml, 0.30 mmol) is added to carry out the reaction for 6 hours. Upon completion of the reaction, water and DCM (50 ml×2) are used for extraction and washing is carried out again with brine. After removing water with $Na_2SO_4$ and then concentrating under reduced pressure, the mixture obtained is purified in a silica gel column chromatography (10% EA in Hex) to obtain the target compound (1.30 g, 85%).

$^1$H-NMR (300 MHz, CD3OD) δ 1.15 (d, J=6.9 Hz, 6H), 1.41 (s, 9H), 2.81 (sept, J=6.9 Hz, 1H), 3.82 (s, 2H), 6.65 (s, 1H), 6.86 (d, J=7.8 Hz, 1H), 7.34 (d, J=7.8 Hz, 1H), 7.57 (br, 1H) 7.77-7.90 (br, 3H);

452.83 [M+H]+, 904.94 [2M+H]+ for LCMS.

EXAMPLE 64

Preparation of 2-amino-N-(4b-hydroxy-7-isopropyl-10-oxo-4b,10-dihydro-9bH-indeno[1,2-b]benzofuran-9b-yl)acetamide While tert-butyl(2-((4b-hydroxy-7-isopropyl-10-oxo-4b,10-dihydro-9bH-indeno[1,2-b]benzofuran-9b-yl) amino)-2-oxoethyl)carbamate (900 mg, 2.00 mmol) is added in DCM (10 ml, 0.2 M) and stirred, trifluoroacetic acid (1.52 ml, 20.0 mmol) is added. After reacting at normal temperature for 12 hours, DCM (150 ml) and over-saturated $NaHCO_3$ (50 ml×2) is used for extraction upon completion of the reaction and then brine (50 ml) washing is carried out again. Water was removed with Na2SO4 and concentration under reduced pressure is carried out to obtain the target compound (670 mg, 96%).

$^1$H-NMR (300 MHz, CD3OD) δ 1.16 (d, J=6.9 Hz, 6H), 2.82 (sept, J=6.9 Hz, 1H), 3.34 (s, 2H), 6.65 (s, 1H), 6.86 (d, J=7.8 Hz, 1H), 7.35 (d, J=7.8 Hz, 1H), 7.69-7.72 (m, 2H); 352.51 [M+H]+, 704.85 [2M+H]+ for LCMS.

EXAMPLE 65

Preparation of 4b-hydroxy-7,8-dimethyl-9b-(methylamino)-4b,9b-dihydro-10H-indeno[1,2-b]benzofuran-10-one After dissolving 9b-chloro-4b-hydroxy-7,8-dimethyl-4b, 9b-dihydro-10H-indeno[1,2-b]benzofuran-10-one (2 g, 6.65 mmol) in THF (66 ml, 0.1 M), the reaction temperature is kept at −200° C. After adding methyl amine (6.65 ml, 13.30 mmol) in that order, the reaction is carried out for 5 hours. Upon completion of the reaction, THF is concentrated under reduced pressure and removed and then DCM and water are used for extraction before brine washing is carried out again. After removing water with $Na_2SO_4$, silica gel chromatography is used for purification to obtain the target compound (710 mg, 36%).

$^1$H-NMR (300 MHz, CDCl3) δ 2.17 (s, 6H), 2.31 (s, 6H), 6.64 (s, 1H), 7.13 (s, 1H), 7.49 (t, J=7.5 Hz, 1H), 7.76 (t, J=7.5 Hz, 2H), 7.98 (d, J=7.5 Hz, 1H);

295.44 [M+H]+ for LCMS.

EXAMPLE 66

Preparation of N-tertbutoxycarbonyl[N3-(4b-hydroxy-7-isopropyl-10-oxo-4b,10-dihydro-9bH-indeno[1,2-b]benzofuran-9b-yl)]guanidine After dissolving N',N'-di-tert-butoxycarbonyl[11-(4b-hydroxy-7-isopropyl-10-oxo-4b,10-dihydro-9bH-indeno[1,2-b]benzofuran-9b-yl)]guanidine (200 mg, 0.37 mmol) in MeOH (2 ml, 0.2 M), stirring is carried out while adding 2 N HCl (1.0 ml, 5 eq. approx.). After reacting at normal temperature for 12 hours, concentration under reduced pressure is carried out upon completion of the reaction before a silica gel column chromatography (3% MeOH in DCM) is used for purification immediately. Concentration under reduced pressure and drying is carried out to obtain the target compound (115 mg, 71%).

$^1$H-NMR (300 MHz, CD3OD) δ 1.19 (d, J=6.9 Hz, 6H), 1.50 (s, 9H), 2.85 (sept, J=6.9 Hz, 1H), 6.68 (s, 1H), 6.88 (d, J=7.8 Hz, 1H), 7.38 (d, J=7.8 Hz, 1H), 7.54-7.62 (m, 2H), 7.73-7.78 (m, 2H);

437.86 [M+H]+, 875.03 [2M+H]+ for LCMS.

EXAMPLE 67

Preparation of N,N'-di-tertbutoxycarbonyl[1-(4b-hydroxy-7,8-dimethyl-10-oxo-4b,10-dihydro-9bH-indeno[1,2-b]benzofuran-9b-yl)]-1-methyl guanidine After dissolving 4b-hydroxy-7,8-dimethyl-9b-(methylamino)-4b,9b-dihydro-10H-indeno[1,2-b]benzofuran-10-one (295.3 mg, 1.0 mmol) in DMF (0.2 M, 5 ml), 1,1,2,3,3-pentamethyl isothiouronium iodide (287.7 mg, 1.05 mmol) is added. While stirring at 0° C., TEA and $HgCl_2$ (298.7 mg, 1.1 mmol) are added to carry out the reaction for 2 hours. Upon completion of the reaction, water and ethyl acetate are used for extraction and brine washing is carried out again. After removing water with $Na_2SO_4$, a silica gel chromatography is used for purification to obtain the target compound (120 mg, 22%).

$^1$H-NMR (300 MHz, CD3OD) δ 1.46 (s, 9H), 1.49 (s, 9H), 2.21 (s, 6H), 2.26 (s, 3H), 6.62 (s, 1H), 7.20 (s, 1H), 7.74-7.50 (m, 2H), 7.62 (d, J=6.9 Hz, 1H), 7.81 (d, J=6.9 Hz, 1H);

538.3 [M+H]+ for LCMS.

EXAMPLE 68

Preparation of N-(4b-hydroxy-7-isopropyl-10-oxo-4b,10-dihydro-9bH-indeno[1,2-b]benzofuran-9b-yl) thiopene-2-sulfonamide After adding and dissolving 9b-amino-4b-hydroxy-7-isopropyl-4b,9b-dihydro-10H-indeno[1,2-b]benzofuran-10-one (500 mg, 1.69 mmol) in acetonitrile (ACN) (17 ml, 0.1 M), benzene sulfonyl chloride (0.24 ml, 1.86 mmol) is added. After adding pyridine (0.27, 3.38 mmol), the reaction is carried out at normal temperature for 12 hours. Upon completion of the reaction, water and DCM are used for extraction and then brine washing is carried out. After removing water with $Na_2SO_4$, purification is carried out on silica gel column chromatography to obtain the target compound (460 mg, 62%).

$^1$H-NMR (300 MHz, CDCl3) δ 1.15 (d, J=6.9 Hz, 6H), 2.71-2.80 (m, 1H), 6.00 (br, 1H), 6.09 (br, 1H), 6.30 (d, J=7.8 Hz, 1H), 6.52 (d, J=7.8 Hz, 1H), 6.70 (s, 1H), 6.77 (t, J=4.5 Hz, 1H), 6.93-6.94 (m, 1H), 7.45 (d, J=4.5 Hz, 1H), 7.55 (t, J=7.8 Hz, 1H), 7.75-7.84 (m, 2H), 8.03 (d, J=7.8 Hz, 1H);

440.0 [M+H]+ for LCMS.

EXAMPLE 69

Preparation of N-(4b-hydroxy-7-isopropyl-10-oxo-4b,10-dihydro-9bH-indeno[1,2-b]benzofuran-9b-yl) benzene sulfonamide After dissolving 9b-amino-4b-hydroxy-7-isopropyl-4b,9b-dihydro-10H-indeno[1,2-b]benzofuran-10-one (500 mg, 1.7 mmol) in DCM (17 ml, 0.1 M) and adding benzene sulfonyl chloride (0.24 ml, 1.86 mmol), $K_2CO_3$ (467 mg, 3.38 mmol) and 18-crown-6 (89 mg, 0.34 mmol) are added and then stirring is carried out at room temperature for 12 hours. After diluting the reaction mixture with DCM and washing with water and brine, $Na_2SO_4$ is used to remove water and then concentration under reduced pressure is carried out. Purification is carried out in a silica gel column chromatography to obtain the target compound (190 mg, 26%).

$^1$H-NMR (300 MHz, CDCl3) δ 1.22 (d, J=7.8 Hz, 6H) 2 89-2.93 (m, 1H), 6.81 (s, 1H), 7.05 (d, J=8.1 Hz 1H), 7 49 (t, J=7.5 Hz, 2H), 7.59-7.69 (m, 2H), 7.83-7.95 (m 3H), 8 11 (d, J=7.8 Hz, 3H);

434.0 [M+H]+ for LCMS.

EXAMPLE 70

Preparation of 4b-hydroxy-7,8-dimethyl-9b-(pyridin-2-yl amino)-4b,9b-dihydro-10H-indeno[1,2-b]benzofuran-10-one After dissolving 9b-chloro-4b-hydroxy-7,8-dimethyl-4b, 9b-dihydro-10H-indeno[1,2-b]benzofuran-10-one (300 mg, 1.0 mmol) in THF (10 ml, 0.1 M) and cooling to −30° C., 2-amino pyridine (98.5 mg, 1.05 mmol) is added. After adding TEA (0.153 ml, 1.10 mmol) at the same temperature, the reaction mixture is allowed to stand for 2 hours until it reaches room temperature. Upon completion of the reaction, concentration under reduced pressure is carried out.

After the concentrated reaction mixture is diluted with ethyl acetate (100 ml), and then washed with water and brine; water is removed with $Na_2SO_4$ and then concentration under reduced pressure is carried out. Purification is carried out in a silica gel column chromatography (20-25%. EtAc in hexane) to obtain the target compound (150 mg, 42%).

$^1$H-NMR (300 MHz, CDCl3) δ 2.07 (s, 3H), 2.11 (s, 3H), 5.50 (s, 1H), 6.57 (s, 1H), 6.64-6.68 (m, 1H), 6.74 (d, J=8.4 Hz, 1H), 7.01 (s, 1H), 7.43-7.55 (m, 2H), 7.78-7.84 (m, 2H), 7.92 (d, J=4.8 Hz, 1H), 8.06 (d, J=7.8 Hz, 1H), 9.06 (s, 1H);

359.1 [M+H]+ for LCMS.

EXAMPLE 71

Preparation of N-(4b-hydroxy-7-isopropyl -10-oxo-4b,10-dihydro-9bH-indeno[1,2-b]benzofuran-9b-yl) propane-1-sulfonamide After dissolving 9b-chloro-4b-hydroxy-7,8-dimethyl-4b, 9b-dihydro-10H-indeno[1,2-b]benzofuran-10-one (300 mg, 1.0 mmol) in acetonitrile (ACN) (10 ml, 0.1 M), 1-propane sulfonyl chloride (0.125 ml, 1.10 mmol) is added. After pyridine (0.164 ml, 2.03 mmol) is added at room temperature, stirring is carried out for 10 hours. Upon completion of the reaction, concentration under reduced pressure is carried out. After the concentrated reaction mixture is diluted with ethyl acetate (100 ml), it is then washed with water and brine. Water is removed with $Na_2SO_4$ and then concentration under reduced pressure is carried out. Purification is carried at in a silica gel column chromatography (20%. EA in hexanes) to obtain the target compound (195 mg, 48%, yellow solid).

$^1$H-NMR (300 MHz, CDCl3) δ 0.96 (t, J=7.5 Hz, 3H), 1.18 (dd, J=6.9 Hz, J=4.2 Hz, 6H),1.78-1.91 (m, 2H), 2.42-2.52 (m, 1H), 2.63-2.77 (m, 1H), 2.84 (sept, J=6.9 Hz, 1H), 5.50 (s, 1H), 6.22 (s, 1H), 6.77 (s, 1H), 6.85 (d, J=7.8 Hz, 1H), 7.30 (d, J=7.8 Hz, 1H), 7.54-7.61 (m, 1H), 7.77-7.94 (m, 2H), 8.02 (d, J=7.8 Hz, 1H);

402.1 [M+H]+ for LCMS.

EXAMPLE 72

Preparation of 1-chloro-N-(4b-hydroxy-7-isopropyl-10-oxo-4b,10-dihydro-9bH-indeno[1,2-b]benzofuran-9b-yl)methane sulfonamide After dissolving 9b-chloro-4b-hydroxy-7,8-dimethyl-4b, 9b-dihydro-10H-indeno[1,2-b]benzofuran-10-one (300 mg, 1.0 mmol) in acetonitrile (ACN) (10 ml, 0.1 M) at room temperature and then adding chloromethane sulfonyl chloride (0.102 ml, 1.10 mmol), pyridine (0.164 ml, 2.03 mmol) is added before stirring is carried out for 10 hours. Upon completion of the reaction, concentration under reduced pressure is carried out. After the concentrated reaction mixture is diluted with ethyl acetate (100 ml), it is then washed with water and brine. Water is removed with $Na_2SO_4$ and then concentration under reduced pressure is carried out. Purification is carried at in a silica gel column chromatography (20%. EA in hexanes) to obtain the target compound (150 mg, 38%, yellow solid).

¹H-NMR (300 MHz, CDCl3) δ 1.18 (dd, J=6.9 Hz, J=4.2 Hz, 6H), 2.84 (sept, J=6.9 Hz, 1H), 3.74 (d, J=12.0 Hz, 1H), 4.47 (d, J=12.0 Hz, 1H), 6.75 (s, 1H), 6.87 (d, J=7.8 Hz, 1H), 7.44 (d, J=7.8 Hz, 1H), 7.55-7.60 (m, 1H), 7.76-7.86 (m, 2H), 8.02 (d, J=7.8 Hz, 1H);

408.1 [M+H]+ for LCMS.

EXAMPLE 73

Preparation of 9b-((4,5-dihydrothiazol-2-yl) amino)-4b-hydroxy-7-isopropyl-4b,9b-dihydro-10H-indeno-[1,2-b]benzofuran-10-one After dissolving 9b-chloro-4b-hydroxy-7,8-dimethyl-4b,9b-dihydro-10H-indeno[1,2-b]benzofuran-10-one (315 mg, 1.0 mmol) in THF (10 ml, 0.1 M) and cooling to −78° C., 2-amino thiazoline chloride (146 mg, 1.05 mmol) is added. TEA (0.307 mL, 2.20 mmol) is added at same temperature. Stirring is carried out at room temperature for 3 hours. Upon completion of the reaction, concentration under reduced pressure is carried out. After the concentrated reaction mixture is diluted with ethyl acetate (100 ml), it is then washed with water and brine. Water is removed with Na₂SO₄ and then concentration under reduced pressure is carried out. Purification is carried at in a silica gel column chromatography (2:1=EA:hexanes) to obtain the target compound (210 mg, 55%).

¹H-NMR (300 MHz, CD3OD) δ 1.20 (d, J=6.9 Hz, 6H), 2.83 (sept, J=6.9 Hz, 1H), 3.49-3.72 (br, 4H), 6.65 (s, 1H), 6.83 (d, J=7.8 Hz, 1H), 7.17 (d, J=7.8 Hz, 1H), 7.53-7.80 (m, 4H);

381.1 [M+H]+ for LCMS.

EXAMPLE 74

Preparation of 4b-hydroxy-7-isopropyl-9b-(oxazol-2-yl amino)-4b,9b-dihydro-10H-indeno[1,2-b]benzofuran-10-one 9b-chloro-4b-hydroxy-7-isopropyl-4b,9b-dihydro-10H-indeno[1,2-b]benzofuran-10-one (316 mg, 1.00 mmol) is dissolved in THF (10 ml, 0.1 M). After adding 3-amino isooxazole (89 mg, 1.05 mmol) and TEA (0.15 ml, 1.1 mmol) at −30° C., stirring is carried out at room temperature for 8 hours. After concentrating THF and dissolving in DCM, washing is carried out with water and brine. After extracting organic layers, water is removed with Na₂SO₄ and then concentration under reduced pressure is carried out. Purification is carried out in a silica gel column chromatography to obtain the target compound (50 mg, 14%).

¹H-NMR (300 MHz, CDCl3) δ 1.13-1.16 (m, 6H), 2.75-2.85 (m, 1H), 5.37 (br, 1H), 5.92 (br, 1H), 6.10 (s, 1H), 6.71 (s, 1H), 6.77 (d, J=7.8 Hz, 1H), 7.22 (d, J=7.8 Hz, 1H), 7.55 (t, J=7.2 Hz, 1H), 7.79-7.84 (m, 2H); 7.98 (s, 1H), 8.04 (d, J=7.8 Hz, 1H);

363.1 [M+H]+ for LCMS.

EXAMPLE 75

Preparation of 4b-hydroxy-7-isopropyl-9b-(pyridin-2-yl amino)-4b,9b-dihydro-10H-indeno[1,2-b]benzofuran-10-one 9b-chloro-4b-hydroxy-7,8-dimethyl-4b,9b-dihydro-10H-indeno[1,2-b]benzofuran-10-one (315 mg, 1.0 mmol) is dissolved in THF (10 ml, 0.1 M). After adding 2-amino pyridine (98.5 mg, 1.05 mmol) at −30° C., TEA (0.153 ml, 1.10 mmol) is added. The temperature is raised to normal temperature and then stirring is carried out for 4 hours. After the reactants are concentrated and diluted with ethyl acetate (100 ml), washing is carried out with water (50 ml×2) and brine (50 ml). After extracting organic layers, water is removed with Na₂SO₄ and then concentration under reduced pressure is carried out. Purification is carried out in a silica gel column chromatography (20% EA in hexanes) to obtain the target compound (174 mg, 47%).

¹H-NMR (300 MHz, CDCl3) δ 1.12 (dd, J=6.9 Hz, J=3.0 Hz 6H), 2.76 (sept, J=6.9 Hz, 1H), 5.48 (s, 1H), 6.64-6.75 (m, 4H) 7.16 (d, J=7.8 Hz, 1H), 7.43-7.57 (m, 2H), 7.79-7.85 (m, 2H), 7.91 (d, J=4.5 Hz, 1H), 8.07 (d, J=7.8 Hz, 1H), 9.05 (s, 1H);

373.1 [M+H]+ for LCMS

In Table 1 below are listed chemical structural formulae of the compounds prepared in Examples 1-75 above.

TABLE 1

| Example | Chemical Structural Formula |
|---|---|
| 1 | 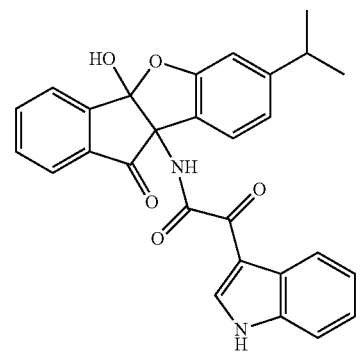 [SMILES: CC(C)c1ccc2c(c1)OC1(O)c3ccccc3C(=O)C21NC(=O)C(=O)c1c[nH]c2ccccc12] |
| 2 | 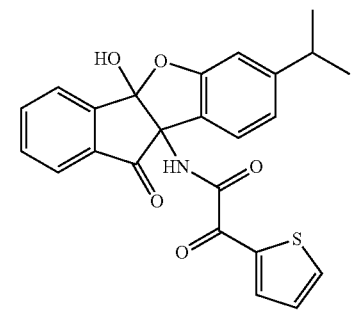 [SMILES: CC(C)c1ccc2c(c1)OC1(O)c3ccccc3C(=O)C21NC(=O)C(=O)c1cccs1] |
| 3 | 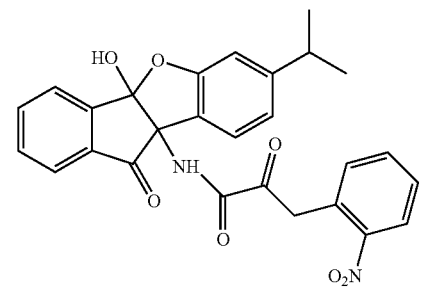 [SMILES: CC(C)c1ccc2c(c1)OC1(O)c3ccccc3C(=O)C21NC(=O)C(=O)Cc1ccccc1[N+](=O)[O-]] |

TABLE 1-continued
| Example | Chemical Structural Formula |
|---|---|
| 4 | 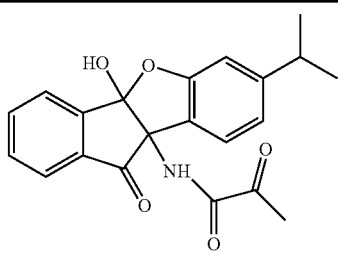 |
| 5 | 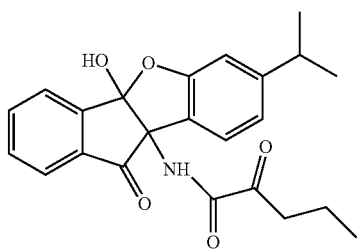 [SMILES: CCCC(=O)C(=O)NC12C(=O)c3ccccc3C1(O)Oc1cc(C(C)C)ccc12] |
| 6 | 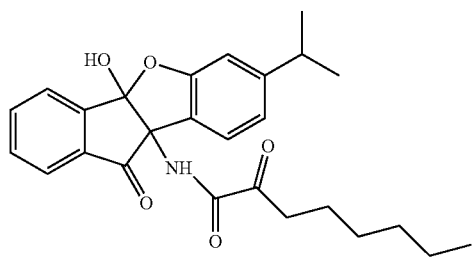 [SMILES: CCCCCCC(=O)C(=O)NC12C(=O)c3ccccc3C1(O)Oc1cc(C(C)C)ccc12] |
| 7 | 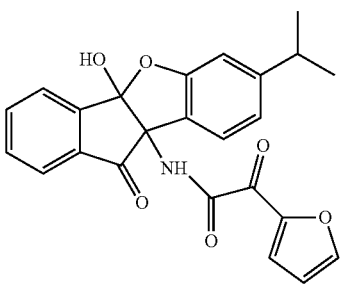 [SMILES: CC(C)c1ccc2c(c1)OC1(O)c3ccccc3C(=O)C21NC(=O)C(=O)c1ccco1] |
| 8 | 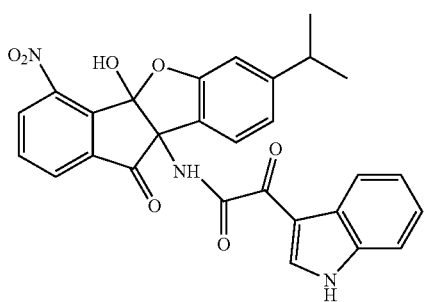 [SMILES: CC(C)c1ccc2c(c1)OC1(O)c3c(cccc3[N+](=O)[O-])C(=O)C21NC(=O)C(=O)c1c[nH]c2ccccc12] |
| 9 | 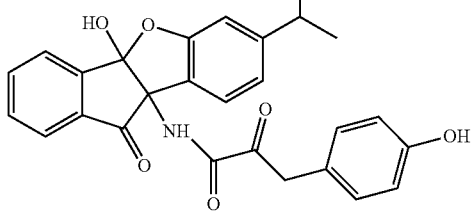 |
| 10 | 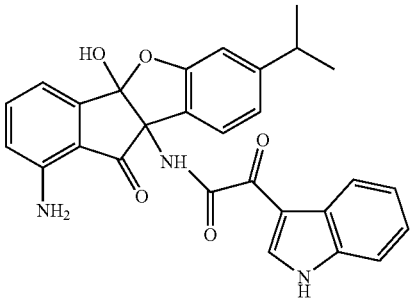 [SMILES: CC(C)c1ccc2c(c1)OC1(O)c3cccc(N)c3C(=O)C21NC(=O)C(=O)c1c[nH]c2ccccc12] |
| 11 | 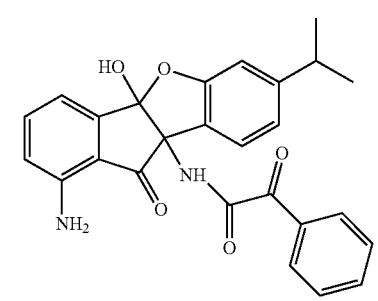 [SMILES: CC(C)c1ccc2c(c1)OC1(O)c3cccc(N)c3C(=O)C21NC(=O)C(=O)c1ccccc1] |
| 12 | 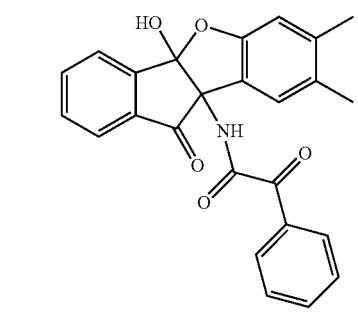 [SMILES: Cc1cc2c(cc1C)C1(NC(=O)C(=O)c3ccccc3)C(=O)c3ccccc3C1(O)O2] |
| 13 | 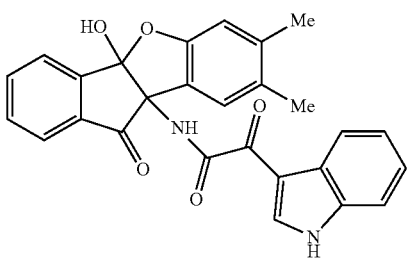 [SMILES: Cc1cc2c(cc1C)C1(NC(=O)C(=O)c3c[nH]c4ccccc34)C(=O)c3ccccc3C1(O)O2] |

TABLE 1-continued

| Example | Chemical Structural Formula |
|---------|---|
| 14 | |
| 15 | |
| 16 | |
| 17 | |
| 18 | |
| 19 | |
| 20 | |
| 21 | |
| 22 | |
| 23 | |

TABLE 1-continued
| Example | Chemical Structural Formula |
|---|---|
| 24 | 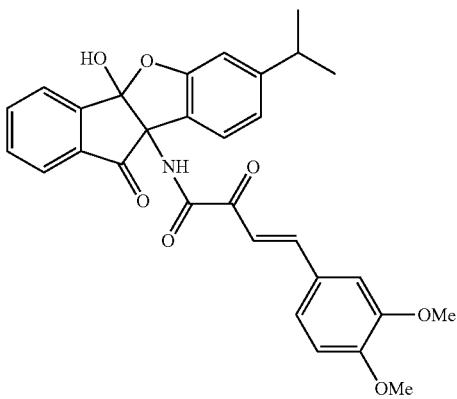 [SMILES: COc1ccc(/C=C/C(=O)C(=O)NC23C(=O)c4ccccc4C2(O)Oc2cc(C(C)C)ccc23)cc1OC] |
| 25 | 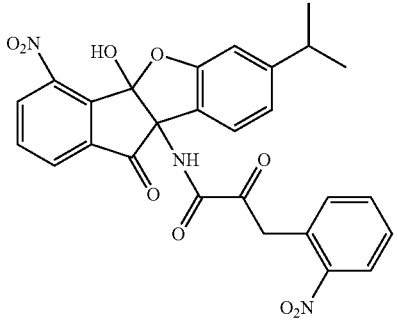 [SMILES: CC(C)c1ccc2c(c1)OC1(O)c3c(cccc3[N+](=O)[O-])C(=O)C21NC(=O)C(=O)Cc1ccccc1[N+](=O)[O-]] |
| 26 | 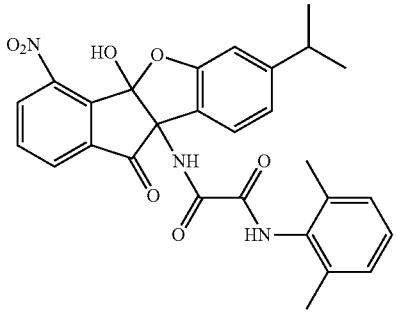 [SMILES: Cc1cccc(C)c1NC(=O)C(=O)NC12C(=O)c3cccc([N+](=O)[O-])c3C1(O)Oc1cc(C(C)C)ccc12] |
| 27 | 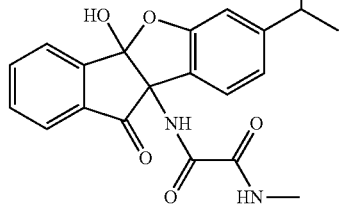 |
| 28 | 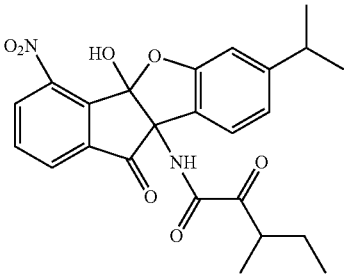 [SMILES: CCC(C)C(=O)C(=O)NC12C(=O)c3cccc([N+](=O)[O-])c3C1(O)Oc1cc(C(C)C)ccc12] |
| 29 | 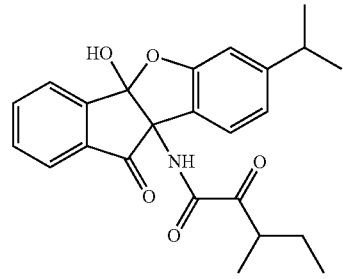 [SMILES: CCC(C)C(=O)C(=O)NC12C(=O)c3ccccc3C1(O)Oc1cc(C(C)C)ccc12] |
| 30 | 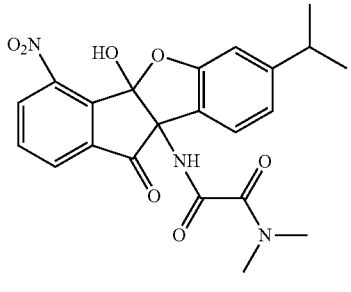 [SMILES: CC(C)c1ccc2c(c1)OC1(O)c3c(cccc3[N+](=O)[O-])C(=O)C21NC(=O)C(=O)N(C)C] |
| 31 | 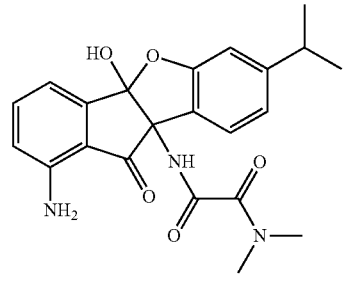 [SMILES: CC(C)c1ccc2c(c1)OC1(O)c3cccc(N)c3C(=O)C21NC(=O)C(=O)N(C)C] |
| 32 | 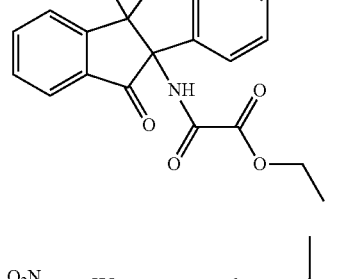 |
| 33 | 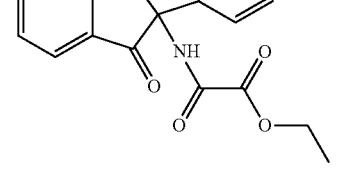 |

TABLE 1-continued

| Example | Chemical Structural Formula |
|---|---|
| 34 | |
| 35 | |
| 36 | |
| 37 | |
| 38 | |
| 39 | |
| 40 | |
| 41 | |
| 42 | |
| 43 | |

TABLE 1-continued
| Example | Chemical Structural Formula |
|---|---|
| 44 | 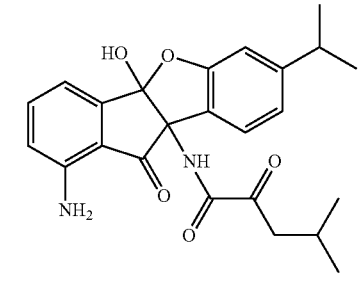 [SMILES: CC(C)CC(=O)C(=O)NC12C(=O)c3c(N)cccc3C1(O)Oc1cc(C(C)C)ccc12] |
| 45 | |
| 46 | |
| 47 | |
| 48 | |
| 49 | |
| 50 | |
| 51 | |
| 52 | |
| 53 | |

TABLE 1-continued

| Example | Chemical Structural Formula |
|---|---|
| 54 | |
| 55 | |
| 56 | |
| 57 | |
| 58 | |
| 59 | |
| 60 | |
| 61 | |
| 62 | |

TABLE 1-continued

| Example | Chemical Structural Formula |
|---|---|
| 63 | |
| 64 | |
| 65 | |
| 66 | |
| 67 | |ора

TABLE 1-continued

| Example | Chemical Structural Formula |
|---|---|
| 68 | |
| 69 | |
| 70 | |
| 71 | |
| 72 | |

TABLE 1-continued

| Example | Chemical Structural Formula |
|---------|------------------------------|
| 73 | (structure) |
| 74 | (structure) |
| 75 | (structure) |
| — | |
| — | |
| — | |

EXPERIMENTAL EXAMPLE 1

Determination of Drug Efficacy Against Picornaviruses Using Cytopathic Effect (CPE) Inhibition Assay In the assay, HeLa (human cervical cancer cells), MRC-5 (human fetal lung fibroblast cells), and RD cells (derived from human rhabdomyosarcoma) were employed. For comparison, ribavirin (Riv), Pleconaril (pleco), and BTA-798 (BTA) were used as controls. Reagents were dissolved at a concentration of 10-40 mg/ml in 100% dimethyl sulfoxide (DMSO). Water-soluble reagents were dissolved in PBS (−) solution and stored at −20° C. On the day of the experiment, they were used in 3 fold to 5 fold concentrations in such a manner that the concentration of dimethyl sulfoxide in each well was between 0.5% and 1%

Pharmaceutical efficacy was determined using a virus-induced cytopathic effect (CPE) inhibition assay. In this regard, after cells suitable for viruses were grown in 96-well plates, dilutions of viruses in DME supplemented with 2% FBS (DME/2% FBS) or MEM supplemented with 2% FBS (MEM/2% FBS) were inoculated in an amount of 100 ul with a concentration corresponding to 100 CCID50 (50% cell culture infective dose) into each well of the plates, and incubated for 30 min-1 hr at 33° C. or 37° C. to allow the viruses to adsorb onto the cells. The culture medium was removed before aliquots of drug dilutions with various concentrations were added in an amount of 100 ul to each well. While HRV (human rhinovirus) was grown at 33° C., the other viruses were incubated in a 37° C. $CO_2$ incubator for 2-3 days. Alternatively, the cells were cultured for 2-3 days without removal of the medium after they were added with 50 ul of each drug dilution having a 2-fold higher concentration and then with 50 ul of the virus dilution Test conditions for each virus are summarized in Table 2 below:

TABLE 2

| Virus | Reference | Host Cell | Incubation Temp. | Incubation Term | Medium |
|-------|-----------|-----------|------------------|-----------------|--------|
| Coxsackie B1 | — | HeLa | 37° C. | 2 days | DME/2% FBS |
| Coxsackie B3 | — | HeLa | 37° C. | 2 days | DME/2% FBS |
| Poliovirus 3 | — | HeLa | 37° C. | 2 days | DME/2% FBS |
| Rhinovirus | — | HeLa | 37° C. | 3 days | MEM/2% FBS |

For HeLa cells, the drugs were measured for $EC_{50}$ (50% maximal effective concentration), which is the concentration of a drug inducing a response halfway between the baseline and maximum, using an MTT assay. With regard to RD and MRC-5 cells, CPE was determined using FDA (Fluorescein diacetate). In order to determine the effect of drug toxicity on efficacy results, at the time of inoculation with the virus, a virus-free medium was added to a cell culture, which was then subjected to the same treatment as the mock-infected cells inoculated with the virus. That is, the medium was removed after one hour of incubation, and dilutions of drugs in the medium were added once more. Following incubation for 2-3 days, the cells were observed under a microscope and the drugs were determined for $CC_{50}$ (50% cytotoxic concentration) at which 50% of the cells were killed, using an MTT assay in which counts of viable cells in mock-infected wells containing drugs were compared to those of viable cells in control wells containing no drugs. In an FDA hydrolysis assay, FDA was added to each well after removal of the medium, and incubated for 20-30 min before fluorescence intensity was measured using a spectrofluorometer to determine CPE in the same manner as in MTT.

That is, the survival rate (% survival) of mock-infected cells for cytotoxicity measurement was calculated using the Mathematical Formula 1 below:

[Mathematical Formula 1]
$$\text{Cell Survival by Drug} = \frac{A(\text{Drug}) - A(\text{Background Solution})}{A(\text{Cell control}) - A(\text{Background Solution})} \times 100\%$$

While 100% cell survival means no cytotoxicity of the drug, the highest cytotoxicity is reflected by 0% cell survival. The 50% cytotoxic concentration was defined as the concentration required to reduce the cell number by 50%. This concentration of the drug is represented as $CC_{50}$. Higher values mean lower cytotoxicity.

In addition, antiviral effects can be calculated using Mathematical Formula 2 below:

$$\text{Antiviral Effect} = \frac{A(\text{Drug/Virus}) - A(\text{Virus Control})}{A(\text{Cell control}) - A(\text{Virus Control})} \times 100\% \quad [\text{Mathematial Formula 2}]$$

If the survival rate is 100%, its antiviral effect is 100% whereas if the survival rate is 0%, its antiviral effect is none. While the concentration of a drug at which the cell in a well infected with a virus can exhibit 50% survival rate is calculated as $EC_{50}$, the lower this value is, the more superior the antiviral effect is.

In Table 3 below are listed $LC_{50}$ concentrations that exhibit cytotoxicity against the compounds in some examples and $EC_{50}$ concentrations that exhibit activities against a number of rhinoviruses belonging to the picornaviruses.

TABLE 3

| Example | $CC_{50}$ (μg/ml) Cytotoxicity | $EC_{50}$ (μg/ml) HRV 14 | HRV 21 | HRV 71 |
|---|---|---|---|---|
| 1 | 7.91 | <1.0 | >7.91 | >7.91 |
| 2 | 8.57 | <0.1 | >8.57 | >8.57 |
| 3 | 1.76 | >1.76 | >1.76 | >1.76 |
| 4 | 9.02 | <0.1 | >9.02 | >9.02 |
| 5 | 8.49 | <0.1 | >8.49 | >8.49 |
| 6 | 8.57 | <1.0 | >8.57 | >8.57 |
| 7 | >10.0 | <0.1 | >10.0 | >10.0 |
| 8 | >10.0 | 2.31 | >10.0 | >10.0 |
| 9 | 3.76 | >3.76 | >3.76 | >3.76 |
| 10 | 4.89 | <0.1 | >4.89 | >4.89 |
| 11 | 7.82 | <0.1 | 3.13 | >7.82 |
| 12 | >10.0 | 2.08 | >10.0 | >10.0 |
| 13 | 8.41 | 1.85 | >8.41 | >8.41 |
| 14 | 8.87 | 1.82 | >8.87 | >8.87 |
| 15 | 8.72 | <1.0 | >8.72 | >8.72 |
| 16 | >10.0 | 1.77 | >10.0 | >10.0 |
| 17 | >10.0 | 6.99 | >10.0 | >10.0 |
| 18 | >10.0 | >10.0 | >10.0 | >10.0 |
| 19 | >10.0 | <10.0 | >10.0 | >10.0 |
| 20 | >10.0 | <10.0 | >10.0 | >10.0 |
| 21 | >10.0 | <1.0 | >10.0 | >10.0 |
| 22 | >10.0 | <0.01 | <10.0 | 8.5 |
| 23 | >10.0 | <10.0 | >10.0 | >10.0 |
| 24 | >10.0 | <10.0 | >10.0 | >10.0 |
| 25 | 2.6 | >2.6 | >2.6 | >2.6 |
| 26 | >10.0 | <10.0 | >10.0 | >10.0 |
| 27 | >10.0 | <1.0 | >10.0 | >10.0 |
| 28 | >10.0 | <10.0 | >10.0 | >10.0 |
| 29 | >10.0 | <1.0 | >10.0 | >10.0 |
| 30 | >10.0 | >10.0 | >10.0 | >10.0 |
| 31 | >10.0 | 0.012 | <10.0 | 73 |
| 32 | >10.0 | <1.0 | >10.0 | >10.0 |
| 33 | >10.0 | >10.0 | >10.0 | >10.0 |
| 34 | >10.0 | <10.0 | >10.0 | >10.0 |
| 35 | >10.0 | <10.0 | >10.0 | >10.0 |
| 36 | >10.0 | <1.0 | >10.0 | >10.0 |
| 37 | >10.0 | <0.1 | >10.0 | >10.0 |
| 38 | >10.0 | <10.0 | >10.0 | >10.0 |
| 39 | 9.5 | <10.0 | >9.5 | >9.5 |
| 40 | >10.0 | <0.1 | >10.0 | >10.0 |
| 41 | >10.0 | <10.0 | >10.0 | >10.0 |
| 42 | >10.0 | <10.0 | >10.0 | >10.0 |
| 43 | >10.0 | >10.0 | >10.0 | >10.0 |
| 44 | n.d | n.d | n.d | n.d |
| 45 | >10.0 | n.d | n.d | n.d |
| 46 | >10.0 | >10.0 | >10.0 | >10.0 |
| 47 | >10.0 | <0.1 | >10.0 | >10.0 |
| 48 | >10.0 | <1.0 | >10.0 | >10.0 |
| 49 | >10.0 | <0.1 | >10.0 | >10.0 |
| 50 | >10.0 | <0.1 | >10.0 | >10.0 |
| 51 | >10.0 | >10.0 | >10.0 | >10.0 |
| 52 | >10.0 | <0.01 | >10.0 | >10.0 |
| 53 | 4.8 | >4.8 | >4.8 | >4.8 |
| 54 | 8.6 | <1.0 | >8.6 | >8.6 |
| 55 | >10.0 | <10.0 | >10.0 | >10.0 |
| 56 | >10.0 | >10.0 | >10.0 | >10.0 |
| 57 | >10.0 | <10.0 | >10.0 | >10.0 |
| 58 | >10.0 | <10.0 | >10.0 | >10.0 |
| 59 | 8.6 | <0.1 | >8.6 | >8.6 |
| 60 | >10.0 | <10.0 | >10.0 | >10.0 |
| 61 | >10.0 | <10.0 | >10.0 | >10.0 |
| 62 | >10.0 | >10.0 | >10.0 | >10.0 |
| 63 | >10.0 | <1.0 | >10.0 | >10.0 |
| 64 | >10.0 | <10.0 | >10.0 | >10.0 |
| 65 | n.d | n.d | n.d | n.d |
| 66 | n.d | n.d | n.d | n.d |
| 67 | n.d | n.d | n.d | n.d |
| 68 | n.d | n.d | n.d | n.d |
| 69 | n.d | n.d | n.d | n.d |
| 70 | n.d | n.d | n.d | n.d |
| 71 | n.d | n.d | n.d | n.d |
| 72 | n.d | n.d | n.d | n.d |
| 73 | n.d | n.d | n.d | n.d |
| 74 | n.d | n.d | n.d | n.d |
| 75 | n.d | n.d | n.d | n.d |

As is indicated in Table 3 above, most of the novel compounds according to the present invention exhibit high $CC_{50}$ concentrations so are found to have low cytotoxicity. In addition, the novel compounds according to the present invention were mostly found to have very high antiviral activities against a number of rhinoviruses (HRV).

Therefore, since the compounds in the example according to the present invention exhibit low cytotoxicity and high antiviral activities against various rhinoviruses, they may be usefully used for a pharmacological composition for preventing or treating diseases caused by the picornaviruses to which they belong.

EXPERIMENTAL EXAMPLE 2

Determination of Drug Effect Against Picornaviruses Using Multicycle Cytopathic Effect (CPE) Reduction Assay The multicycle CPE reduction assay was used to conduct determination of drug efficacy against picornaviruses. The antiviral activity of a compound was initially determined by the CPE reduction assay based on MIS [3-(4,5-dimethylthiazol-2-yl)-5-(3-carboxymethoxyphenyl)-2-(4-sulfophenyl)-2H-tetrazolium.

Specifically, cells grown to confluence in 96-well plates were infected with 100 50% cell culture infected doses ($CCID_{50}$) of virus. After an adsorption period of 2 hrs at 37° C., the virus was removed and serial dilutions of the compounds were added. The cultures were further incubated at 37° C. for 3 days until complete CPE was observed in the infected and untreated virus control (VC). After removal of the medium, 90 ul of a culture medium and 10 ul of MTS-phenazine methosulfate (Promega, Leiden, The Netherlands) were added to each well. After an incubation period of 2 hrs at 37° C., the optical density (OD) of each well was read at 498 nm in a microplate reader.

The % CPE values for evaluating antiviral activity were calculated using Mathematical Formula 3 below:

$$\% \ CPE = 100 \times \frac{OC(CC) - OD(\text{Virus} + \text{Compound})}{OD(CC) - OD(VC)} \quad \text{[Mathematical Formula 3]}$$

The % CPE value for measuring cytotoxicity of a drug was calculated by Mathematical Formula 4 below:

$$\% \ CPE = 100 \times \frac{OD(CC) - OD(\text{Virus} + \text{Compound})}{OD(CC) - OD(\text{Blank})} \quad \text{[Mathematical Formula 4]}$$

In Mathematical Formulae 3 and 4 above,

OD (CC) represents the OD of the background cell culture that is neither induced by a virus nor treated by chemical, OD (VC) represents the OD of the control cell culture that is induced by a virus but not treated by chemical, OD (Virus+Compound) represents the OD of the cell culture infected by a virus that has been treated with a concentrated compound, OD (Compound) represents the OD of the cell culture that has been treated with a concentrated compound only, and OD (Blank) represents the OD of the well to which only the cell culture has been added.

The effective concentration ($EC_{50}$) represents the concentration of a drug at which 50% of cells are allowed to survive by CPE of an induced virus, and the cytotoxicity concentration (CC50) represents the concentration of a drug at which a compound has killed 50% of cells, and they were calculated by the logarithmic interpolation.

In Table 4 below are listed the toxicity concentrations ($CC_{50}$) and effective concentrations ($EC_{50}$) against various viruses for some compounds of the examples.

TABLE 4

| Example | $CC_{50}$ (μg/ml) Cytotoxicity | $EC_{50}$ (μg/ml) CoxB1 | CoxB3 | PV3 |
|---|---|---|---|---|
| 1 | 8.57 | 0.017 | 0.061 | 1.1 |
| 2 | 9.02 | <0.01 | <0.01 | <1.0 |
| 3 | 2.38 | 0.013 | 0.015 | <1.0 |
| 4 | >10.0 | <0.01 | <0.01 | <1.0 |
| 5 | >10.0 | <0.01 | <0.01 | <0.1 |
| 6 | 8.57 | 0.013 | 0.015 | 1.23 |
| 7 | >10.0 | <0.01 | <0.01 | <1.0 |
| 8 | >10.0 | 0.56 | 1.82 | 9.8 |
| 9 | 9.21 | 0.013 | 0.015 | <1.0 |
| 10 | 8.33 | <0.01 | 0.014 | <0.1 |
| 11 | 8.72 | <0.01 | <0.01 | <0.1 |
| 12 | >10.0 | 0.015 | 0.064 | 9.8 |
| 13 | 8.31 | 0.061 | 0.13 | 1.98 |
| 14 | 8.57 | 0.015 | 0.067 | >8.57 |
| 15 | 8.8 | <0.01 | <0.01 | <1.0 |
| 16 | >10.0 | 0.078 | 0.33 | 2.13 |
| 17 | >10.0 | 0.033 | 0.067 | 2.61 |
| 18 | >10.0 | <10.0 | <10.0 | >10.0 |
| 19 | >10.0 | <1.0 | <1.0 | <10.0 |
| 20 | >10.0 | <0.1 | <0.1 | <10.0 |
| 21 | >10.0 | <0.1 | <0.1 | <10.0 |

TABLE 4-continued

| Example | $CC_{50}$ (μg/ml) Cytotoxicity | $EC_{50}$ (μg/ml) CoxB1 | CoxB3 | PV3 |
|---|---|---|---|---|
| 22 | >10.0 | <0.01 | <0.01 | <0.1 |
| 23 | >10.0 | <0.1 | <0.1 | <10.0 |
| 24 | >10.0 | <0.1 | <0.1 | <10.0 |
| 25 | 9.5 | <1.0 | <1.0 | >9.5 |
| 26 | >10.0 | <10.0 | <10.0 | >10.0 |
| 27 | >10.0 | <0.1 | <0.1 | <10.0 |
| 28 | >10.0 | <1.0 | <10.0 | >10.0 |
| 29 | >10.0 | <0.1 | <0.1 | <1.0 |
| 30 | >10.0 | <10.0 | <10.0 | >10.0 |
| 31 | >10.0 | <0.01 | <0.01 | <0.1 |
| 32 | >10.0 | <0.1 | <1.0 | <10.0 |
| 33 | >10.0 | <10.0 | <10.0 | >10.0 |
| 34 | >10.0 | <1.0 | <10.0 | <10.0 |
| 35 | >10.0 | <1.0 | <1.0 | <10.0 |
| 36 | >10.0 | <0.1 | <0.1 | <10.0 |
| 37 | >10.0 | <0.1 | <0.1 | <10.0 |
| 38 | >10.0 | <1.0 | <1.0 | <10.0 |
| 39 | >10.0 | <0.1 | <0.1 | <10.0 |
| 40 | >10.0 | <0.01 | <0.01 | <0.1 |
| 41 | >10.0 | <0.1 | <0.1 | >10.0 |
| 42 | >10.0 | <0.1 | <0.1 | >10.0 |
| 43 | >10.0 | <1.0 | <1.0 | >10.0 |
| 44 | >10.0 | <0.1 | <0.1 | <10.0 |
| 45 | >10.0 | <0.1 | <0.1 | <10.0 |
| 46 | >10.0 | <10.0 | <10.0 | >10.0 |
| 47 | >10.0 | <0.01 | <0.1 | <0.1 |
| 48 | >10.0 | <0.1 | <0.1 | <10.0 |
| 49 | >10.0 | <0.01 | <0.01 | <0.1 |
| 50 | >10.0 | <0.1 | <0.1 | <1.0 |
| 51 | >10.0 | <10.0 | <10.0 | >10.0 |
| 52 | >10.0 | <0.01 | <0.01 | <0.1 |
| 53 | >10.0 | <10.0 | <10.0 | >10.0 |
| 54 | >10.0 | <0.1 | <0.1 | <10.0 |
| 55 | >10.0 | <1.0 | <1.0 | >10.0 |
| 56 | >10.0 | <10.0 | <10.0 | >10.0 |
| 57 | >10.0 | <1.0 | <1.0 | >10.0 |
| 58 | >10.0 | <10.0 | <10.0 | >10.0 |
| 59 | >10.0 | <0.1 | <0.1 | <0.1 |
| 60 | >10.0 | <1.0 | <10.0 | >10.0 |
| 61 | >10.0 | <0.1 | <1.0 | >10.0 |
| 62 | >10.0 | <10.0 | <10.0 | >10.0 |
| 63 | >10.0 | <0.1 | <0.1 | <10.0 |
| 64 | >10.0 | <0.1 | <0.1 | >10.0 |
| 65 | n.d | n.d | n.d | n.d |
| 66 | n.d | n.d | n.d | n.d |
| 67 | n.d | n.d | n.d | n.d |
| 68 | n.d | n.d | n.d | n.d |
| 69 | n.d | n.d | n.d | n.d |
| 70 | n.d | n.d | n.d | n.d |
| 71 | n.d | n.d | n.d | n.d |
| 72 | n.d | n.d | n.d | n.d |
| 73 | n.d | n.d | n.d | n.d |
| 74 | n.d | n.d | n.d | n.d |
| 75 | n.d | n.d | n.d | n.d |

As indicated in Table 4 above, the novel compounds according to the present invention mostly exhibit high $CC_{50}$ concentrations and are found to have low cytotoxicity. In addition, it was found that the novel compounds according to the present invention mostly had high antiviral activities against coxsackievirus B1 (Cox B1), coxsackievirus B3 (Cox B3) and poliovirus 3 (PV3).

Therefore, since the compounds in the examples according to the present invention have low cytotoxicity and exhibit superior antiviral activities against picornaviruses to which coxsackieviruses, polioviruses and rhinoviruses belong, they can be used effectively for prevention or treatment of the diseases caused by such viruses, for example, respiratory, cardiocirculatory, and nervous system diseases, including poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis and otitis media.

FORMULATION EXAMPLE 1

Preparation of Pharmaceutical Formulations

<1-1> Preparation of Powder Agent

| | |
|---|---|
| Compound expressed in Formula 1 or Formula 2 | 2 g |
| Lactose | 1 g |

The above ingredients are mixed and filled in an airtight sac to prepare as a powder agent.

<1-2> Preparation of Tablet

| | |
|---|---|
| Compound expressed in Formula 1 or Formula 2 | 100 mg |
| Corn starch | 100 mg |
| Lactose | 100 mg |
| Magnesium stearate | 2 mg |

The above ingredients are mixed and prepared into tablets according to the typical method for preparing tablets.

<1-3> Preparation of Capsule

| | |
|---|---|
| Compound expressed in Formula 1 or Formula 2 | 100 mg |
| Corn starch | 100 mg |
| Lactose | 100 mg |
| Magnesium stearate | 2 mg |

The above ingredients are mixed and put into gelatin capsules according to the typical method for preparing capsules.

<1-4> Preparation of Injection

| | |
|---|---|
| Compound expressed in Formula 1 or Formula 2 | 10 µg/ml |
| Diluted hydrochloric acid BP | Till pH 3.5 is reached |
| Sodium chloride BP for injection | Max 1 ml. |

With the sodium chloride BP for injection, an appropriate volume of the compound is dissolved according to the present invention, dilute hydrochloric acid BP is used to adjust the pH of the solution to a pH 3.5, and sodium chloride BP for injection is used to control a volume prior to sufficient mixing. After the solution is put in a 5-ml type I ampule made of transparent glass, the air is sealed in the upper lattice by melting the glass. Autoclaving and sterilization is carried out at 120° C. for at least 15 min to prepare an injection.

INDUSTRIAL APPLICABILITY

As the compounds expressed in Formula 1 or Formula 2 according to the present invention that are in equilibria with each other have not only low cytotoxicity but also very superior antiviral activities against picornaviruses including coxsackieviruses, enteroviruses, echoviruses, polioviruses and rhinoviruses, they can be used effectively as pharmaceutical compositions for prevention or treatment of viral disease such as poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, herpangina, foot-and-mouth disease, asthma, chronic obstructive pulmonary disease, pneumonia, sinusitis or otitis media.

The invention claimed is:

1. A compound expressed in Formula 1 or Formula 2 below, a pharmaceutically acceptable salt thereof or an optical isomer thereof:

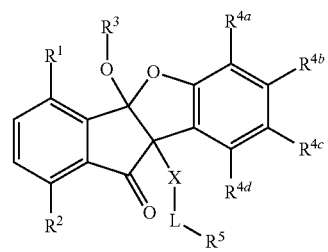

[Formula 1]

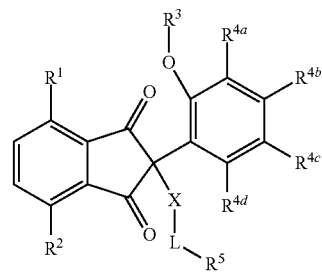

[Formula 2]

(In Formula 1 and 2 above, $R^1$ is —H, linear or branched $C_{1-6}$ alkyl or —$NO_2$;

$R^2$ is —H, linear or branched $C_{1-6}$ alkyl or —$NH_2$;

$R^3$ is —H;

$R^{4a}$, $R^{4b}$, $R^{4c}$ and $R^{4d}$ are independently —H or linear or branched $C_{1-6}$ alkyl;

X-L-$R^5$ is selected from the group consisting of:

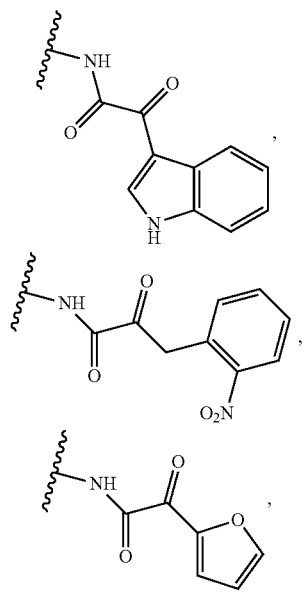

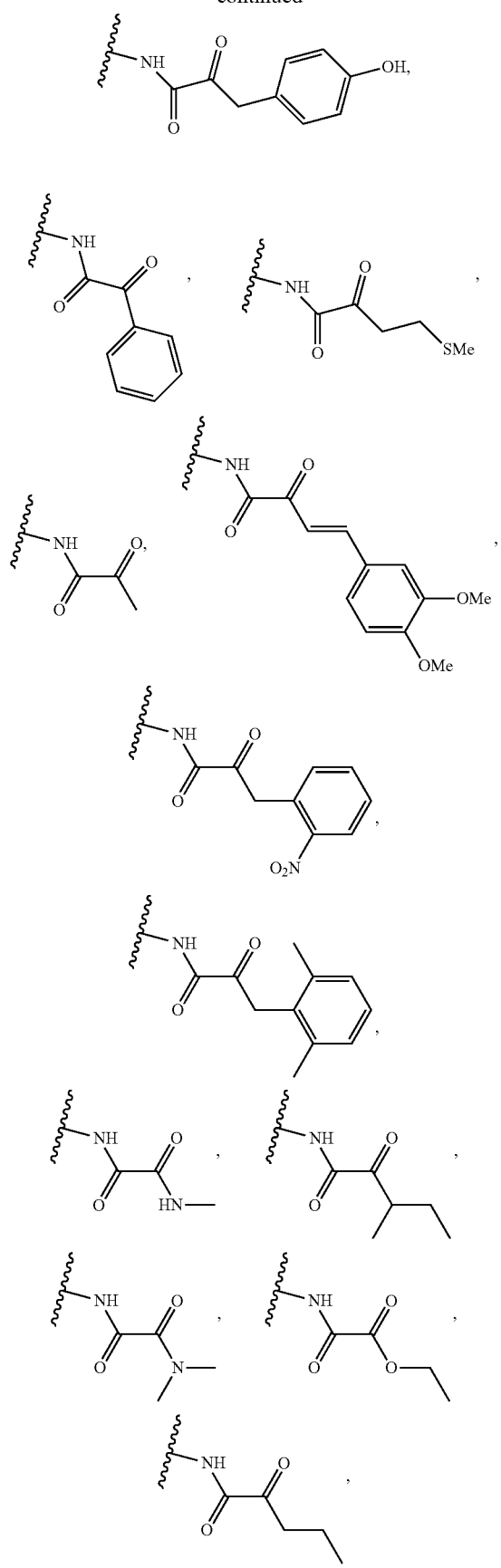
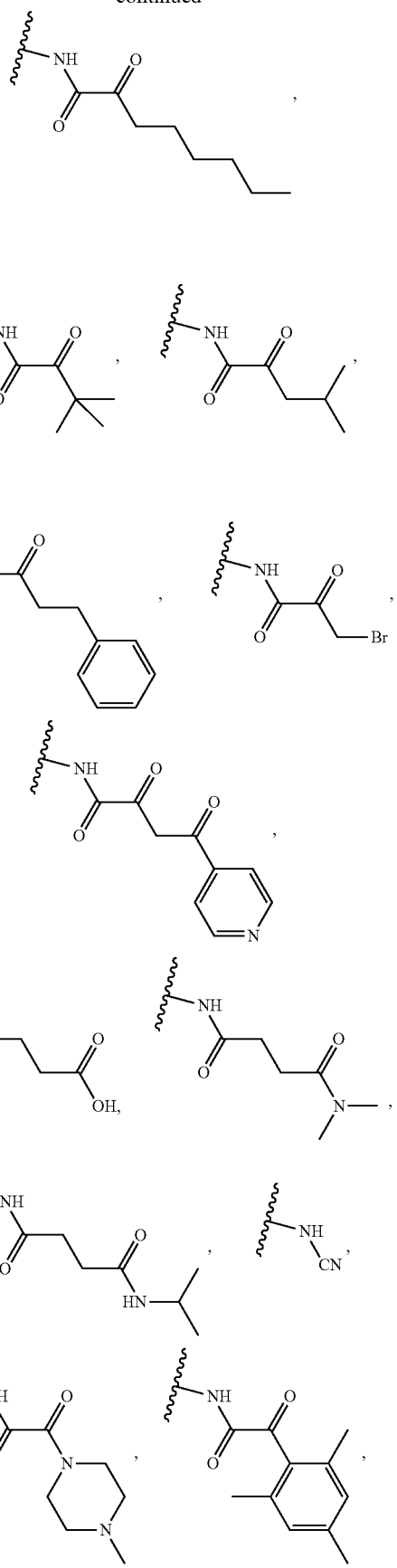

-continued

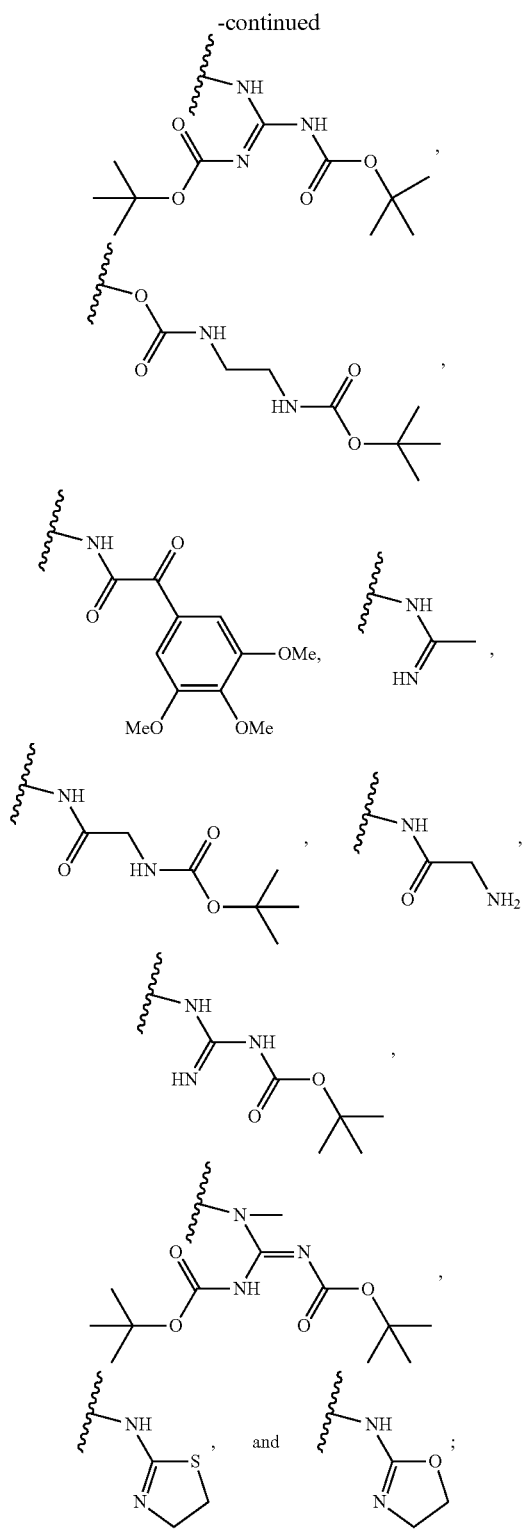

and wherein the compound expressed in Formula 1 and the compound expressed in Formula 2 above exist in a state of equilibrium to each other.

2. The compound, pharmaceutically acceptable salt thereof or optical isomer thereof recited in claim 1, wherein the compound expressed in Formula 1 or Formula 2 is any one selected from a group consisting of:

1) N-(4b-hydroxy-7-isopropyl-10-oxo-9b,10-dihydro-4bH-benzo[d]indeno[1,2-b]furan-9b-yl)-2-(1H-indol-3-yl)-2-oxo acetamide;
3) N-(4b-hydroxy-7-isopropyl-10-oxo-9b,10-dihydro-4bH-indeno[1,2-b]benzofuran-9b-yl)-3-(2-nitro phenyl)-2-oxo propanamide;
4) N-(4b-hydroxy-7-isopropyl-10-oxo-9b,10-dihydro-4bH-indeno[1,2-b]benzofuran-9b-yl)-2-oxo propanamide;
5) N-(4b-hydroxy-7-isopropyl-10-oxo-9b,10-dihydro-4bH-indeno[1,2-b]benzofuran-9b-yl)-2-oxo pentanamide;
6) N-(4b-hydroxy-7-isopropyl-10-oxo-9b,10-dihydro-4bH-indeno[1,2-b]benzofuran-9b-yl)-2-oxo octanamide
7) 2-(furan-2-yl)-6)N-(4b-hydroxy-7-isopropyl-10-oxo-9b,10-dihydro-4bH-indeno[1,2-b]benzofuran-9b-yl)-2-oxo acetamide;
8) N-(4b-hydroxy-7-isopropyl-4-nitro-10-oxo-9b,10-dihydro-4bH-indeno[1,2-b]benzofuran-9b-yl)-2-(1H-indol-3-yl)-2-oxo acetamide;
9) N-(4b-hydroxy-7-isopropyl-10-oxo-9b,10-dihydro-4bH-indeno[1,2-b]benzofuran-9b-yl)-3-(4-hydroxy phenyl)-2-oxo propanamide;
10) N-(1-amino-4b-hydroxy-7-isopropyl-10-oxo-9b,10-dihydro-4bH-indeno[1,2-b]benzofuran-9b-yl)-2-(1H-indol-3-yl)-2-oxo acetamide;
11) N-(1-amino-4b-hydroxy-7-isopropyl-10-oxo-9b,10-dihydro-4bH-indeno[1,2-b]benzofuran-9b-yl)-2-oxo-2-phenyl acetamide;
12) N-(4b-hydroxy-7,8-dimethyl-10-oxo-9b,10-dihydro-4bH-indeno[1,2-b]benzofuran-9b-yl)-2-oxo-2-phenyl acetamide;
13) N-(4b-hydroxy-7,8-dimethyl-10-oxo-9b,10-dihydro-4bH-indeno[1,2-b]benzofuran-9b-yl)-(1H-indol-3-yl)-2-oxo acetamide;
14) N-(4b-hydroxy-7,8-dimethyl-10-oxo-9b,10-dihydro-4bH-indeno[1,2-b]benzofuran-9b-yl)-2-(1H-indol-3-yl)-2-oxo propanamide;
15) N-(4b-hydroxy-7-isopropyl-10-oxo-9b,10-dihydro-4bH-indeno[1,2-b]benzofuran-9b-yl)-2-oxo-2-phenyl acetamide;
16) N-(4b-hydroxy-7-isopropyl-4-nitro-10-oxo-9b,10-dihydro-4bH-indeno[1,2-b]benzofuran-9b-yl)-2-oxo-2-phenyl acetamide;
17) N-(4b-hydroxy-7-isopropyl-10-oxo-9b,10-dihydro-4bH-indeno[1,2-b]benzofuran-9b-yl)-4-(methyl thio)-2-oxo butanamide;
19) N-(4b-hydroxy-7-isopropyl-4-nitro-10-oxo-4b,10-dihydro-9bH-indeno[1,2-b]benzofuran-9b-yl)-2-oxo propanamide;
20) N1-(2,6-dimethylphenyl)-N2-(4b-hydroxy-7-isopropyl-10-oxo-4b,10-dihydro-9bH-indeno[1,2-b]benzofuran-9b-yl)oxal amide;
21) N1-(4b-hydroxy-7-isopropyl-10-oxo-4b,10-dihydro-9bH-indeno[1,2-b]benzofuran-9b-yl)-N2,N2-dimethyl oxal amide;
22) N-(1-amino-4b-hydroxy-7-isopropyl-10-oxo-4b,10-dihydro-9bH-indeno[1,2-b]benzofuran-9b-yl)-2-oxo propanamide;
23) N-(4b-hydroxy-7-isopropyl-10-oxo-4b,10-dihydro-9bH-indeno[1,2-b]benzofuran-9b-yl)-2-oxo-2-(3,4,5-trimethoxyphenyl)acetamide;
24) (E)-4-(3,4-dimethoxyphenyl)-N-(4b-hydroxy-7-isopropyl-10-oxo-4b,10-dihydro-9bH-indeno[1,2-b]benzofuran-9b-yl)-2-oxobut-3-enamide;

25) N-(4b-hydroxy-7-isopropyl-4-nitro-10-oxo-4b,10-dihydro-9bH-indeno[1,2-b]benzofuran-9b-yl)-3-(2-nitrophenyl)-2-oxo propanamide;
26) N1-(2,6-dimethylphenyl)-N2-(4b-hydroxy-7-isopropyl-4-nitro-10-oxo-4b,10-dihydro-9bH-indeno[1,2-b]benzofuran-9b-yl) oxal amide;
27) N1-(4b-hydroxy-7-isopropyl-10-oxo-4b,10-dihydro-9bH-indeno[1,2-b]benzofuran-9b-yl)-N2-methyl oxal amide;
28) N-(4b-hydroxy-7-isopropyl-4-nitro-10-oxo-4b,10-dihydro-9bH-indeno[1,2-b]benzofuran-9b-yl)-3 methyl-2-oxo pentanamide;
29) N-(4b-hydroxy-7-isopryl-10-oxo-4b,10-dihydro-9bH-indeno[1,2-b]benzofuran-9b-yl)-3-methyl-2-oxo pentanamide;
30) N1-(4b-hydroxy-7-isopropyl-4-nitro-10-oxo-4b,10-dihydro-9bH-indeno[1,2-b]benzofuran-9b-yl)-N2-N2-dimethyl oxal amide;
31) N1-(1-amino-4b-hydroxy-7-isopropyl-10-oxo-4b,10-dihydro-9bH-indeno[1,2-b]benzofuran-9b-yl)-N2,N2-dimethyl oxal amide;
32) Ethyl 2-((4b-hydroxy-7-isopropyl-10-oxo-4b,10-dihydro-9bH-indeno[1,2-b]benzofuran-9b-yl) amino)-2-oxo acetate;
33) Ethyl 2-((4b-hydroxy-7-isopropyl-4-nitro-10-oxo-4b,10-dihydro-9bH-indeno[1,2-b]benzofuran-9b-yl) amino)-2-oxo acetate;
34) N-(4b-hydroxy-7-isopropyl-4-nitro-10-oxo-4b,10-dihydro-9bH-indeno[1,2-b]benzofuran-9b-yl)-2-oxo pentanamide;
35) N-(4b-hydroxy-7-isopropyl-4-nitro-10-oxo-4b,10-dihydro-9bH-indeno[1,2-b]benzofuran-9b-yl)-2-oxo octanamide;
36) Ethyl 2-((1-amino-4b-hydroxy-7-isopropyl-10-oxo-4b,10-dihydro-9bH-indeno[1,2-b]benzofuran-9b-yl) amino)-2-oxo acetate;
37) N-(4b-hydroxy-7-isopropyl-10-oxo-4b,10-dihydro-9bH-indeno[1,2-b]benzofuran-9b-yl)-3,3-dimethyl-2-oxo butanamide;
38) N-(4b hydroxyl-7-isopropyl-4-nitro-10-oxo-4b,10-dihydro-9bH-indeno[1,2-b]benzofuran-9b-yl)-4-methyl-2-oxo pentanamide;
39) N-(4b-hydroxy-7-isopropyl-10-oxo-4b,10-dihydro-9bH-indeno[1,2-b]benzofuran-9b-yl)-2-oxo-4-phenyl butanamide;
40) N-(1-amino-4b-hydroxy-7-isopropyl-10-oxo-4b,10-dihydro-9bH-indeno[1,2-b]benzofuran-9b-yl)-3-methyl-2-oxo pentanamide;
41) 3-bromo-N-(4b-hydroxy-7-isopropyl-10-oxo-4b,10-dihydro-9bH-indeno[1,2-b]benzofuran-9b-yl)-2-oxo propanamide;
42) N-(4b-hydroxy-7-isopropyl-10-oxo-4b,10-dihydro-9bH-indeno[1,2-b]benzofuran-9b-yl)-2,4-dioxo-4-(pyridyn-4-yl)butanamide;
43) 4-((4b-hydroxy-7-isopropyl-10-oxo-4b,10-dihydro-9bH-indeno[1,2-b]benzofuran-9b-yl)amino)-4-oxo butanoic acid;
44) N1-(4b-hydroxy-7-isopropyl-10-oxo-4b,10-dihydro-9bH-indeno[1,2-b]benzofuran-9b-yl)-N4,N4-dimethyl succinamide;
45) N1-(4b-hydroxy-7-isopropyl-10-oxo-4b,10-dihydro-9bH-indeno[1,2-b]benzofuran-9b-yl)-N4-isopropyl succinamide;
46) N-(4b-hydroxy-7-isopropyl-10-oxo-4b,10-dihydro-9bH-indeno[1,2-b]benzofuran-9b-yl)cyanamide;
47) N1-(4-amino-(4b-hydroxy-7-isopropyl-10-oxo-4b,10-dihydro-9bH-indeno[1,2-b]benzofuran-9b-yl)-N2-(2,6-dimethylphenyl)oxal amide;
48) N-(4b-hydroxy-7-isopropyl-10-oxo-4b,10-dihydro-9bH-indeno[1,2-b]benzofuran-9b-yl)-2-(4-methylpiperazin-1-yl)-2-oxo acetamide;
49) N-(1-amino-(4b-hydroxy-7-isopropyl-10-oxo-4b,10-dihydro-9bH-indeno[1,2-b]benzofuran-9b-yl)-4-methyl-2-oxo pentanamide;
50) N-(1-amino-4b-hydroxy-7-isopropyl-10-oxo-4b,10-dihydro-9bH-indeno[1,2-b]benzofuran-9b-yl)-2-oxo hexanamide;
51) N-(4b-hydroxy-7-isopropyl-1-nitro-10-oxo-4b,10-dihydro-9bH-indeno[1,2-b]benzofuran-9b-yl)-2mesityl-2-oxo acetamide;
52) N-(1-amino-(4b-hydroxy-7-isopropyl-10-oxo-4b,10-dihydro-9bH-indeno[1,2-b]benzofuran-9b-yl)-2-oxo pentanamide;
53) N-(4b-hydroxy-7-isopropyl-4-nitro-10-oxo-4b,10-dihydro-9bH-indeno[1,2-b]benzofuran-9b-yl)-2-oxo-4-phenyl butanamide;
54) N-(1-amino-4b-hydroxy-7-isopropyl-10-oxo-4b,10-dihydro-9bH-indeno[1,2-b]benzofuran-9b-yl)-2-mesityl-2-oxo acetamide;
55) N,N'-di-tert-butoxycarbonyl[1]-(4b-hydroxy-7-isopropyl-10-oxo-4b,10-dihydro-9bH-indeno[1,2-b]benzofuran-9b-yl)]guanidine;
56) Tert-butyl(4b-hydroxy-7-isopropyl-10-oxo-4b,10-dihydro-9bH-indeno[1,2-b]benzofuran-9b-yl)ethan-1,2-diyl dicarbamate;
57) 4-((4b-hydroxy-7-isopropyl-10-oxo-4b,10-dihydro-9bH-indeno[1,2-b]benzofuran-9b-yl)amino)-4-oxo butanoic acid;
58) N-(4b-hydroxy-7-isopropyl-4-nitro-10-oxo-4b,10-dihydro-9bH-indeno[1,2-b]benzofuran-9b-yl)2-oxo-2-(3,4,5-trimethoxyphenyl)acetamide;
59) N-(4b-hydroxy-7-isopropyl-4-nitro-10-oxo-4b,10-dihydro-9bH-indeno[1,2-b]benzofuran-9b-yl)-2-oxo-4-phenyl butanamide;
60) N-(4b-hydroxy-7-isopropyl-10-oxo-4b,10-dihydro-9bH-indeno[1,2-b]benzofuran-9b-yl)acetimide amide;
63) tert-butyl(2-((4b-hydroxy-7-isopropyl-10-oxo-4b,10-dihydro-9bH-indeno[1,2-b]benzofuran-9b-yl)amino)-2-oxoethyl)carbamate;
64) 2-amino-N-(4b-hydroxy-7-isopropyl-10-oxo-4b,10-dihydro-9bH-indeno[1,2-b]benzofuran-9b-yl)acetamide;
66) N-tert butoxy carbonyl[N3-(4b-hydroxy-7-isopropyl-10-oxo-4b,10-dihydro-9bH-indeno[1,2-b]benzofuran-9b-yl)]guanidine;
67) N,N'-di-tertbutoxycarbonyl[1-(4b-hydroxy-7,8-dimethyl-10-oxo-4b,10-dihydro-9bH-indeno[1,2-b]benzofuran-9b-yl]-1-methyl guanidine;
73) 9b-((4,5-dihydrothiazol-2-yl) amino)-4b-hydroxy-7-isopropyl-4b,9b-dihydro-10H-indeno-[1,2-b]benzofuran-10-one; and
74) 4b-hydroxy-7-isopropyl-9b-(oxazol-2-yl amino)-4b,9b-dihydro-10H-indeno[1,2-b]benzofuran-10-one.

3. A pharmaceutical composition comprising a therapeutically effective amount of the compound of claim 1, a pharmaceutically acceptable salt thereof, or an optical isomer thereof, and a diluent or excipient.

4. A pharmaceutical composition comprising a therapeutically effective amount of the compound of claim 2, a pharmaceutically acceptable salt thereof, or an optical isomer thereof, and a diluent or excipient.

* * * * *